(12) United States Patent
Tuschl et al.

(10) Patent No.: US 9,359,636 B2
(45) Date of Patent: *Jun. 7, 2016

(54) METHODS FOR FIXING AND DETECTING RNA

(75) Inventors: Thomas Tuschl, Brooklyn, NY (US);
Pavol Cekan, Gaithersburg, MD (US);
Neil Renwick, New York, NY (US)

(73) Assignee: The Rockefeller University, New York, NY (US)

( * ) Notice: Subject to any disclaimer, the term of this patent is extended or adjusted under 35 U.S.C. 154(b) by 34 days.

This patent is subject to a terminal disclaimer.

(21) Appl. No.: 14/235,147

(22) PCT Filed: Jul. 27, 2012

(86) PCT No.: PCT/US2012/048727
§ 371 (c)(1),
(2), (4) Date: Mar. 28, 2014

(87) PCT Pub. No.: WO2013/016712
PCT Pub. Date: Jan. 31, 2013

(65) Prior Publication Data
US 2014/0220574 A1    Aug. 7, 2014

Related U.S. Application Data

(60) Provisional application No. 61/512,228, filed on Jul. 27, 2011.

(51) Int. Cl.
*C12Q 1/68* (2006.01)
*G01N 1/30* (2006.01)
*C12N 15/11* (2006.01)

(52) U.S. Cl.
CPC ............ *C12Q 1/6806* (2013.01); *C12N 15/111* (2013.01); *G01N 1/30* (2013.01); *C12N 2310/141* (2013.01); *C12N 2320/10* (2013.01); *C12Q 2600/178* (2013.01)

(58) Field of Classification Search
CPC ................................ C12Q 1/6806; G01N 1/30
USPC ........................................................ 435/6.1
See application file for complete search history.

(56) References Cited

U.S. PATENT DOCUMENTS

| 4,888,278 | A | 12/1989 | Singer et al. |
| 7,642,348 | B2 | 1/2010 | Bentwich et al. |
| 7,825,229 | B2 | 11/2010 | Itzhak et al. |
| 9,005,893 | B2 * | 4/2015 | Tuschl et al. .................. 435/6.11 |
| 2004/0180368 | A1 | 9/2004 | McGall |
| 2007/0269799 | A9 | 11/2007 | Zhang |
| 2010/0233706 | A1 | 9/2010 | Tuchl et al. |

OTHER PUBLICATIONS

David P. Bartel, "MicroRNAs: Genomics, Biogenesis, Mechanism, and Function", Cell, vol. 116, pp. 281-297 (2004).

Farazi et al., "The Growing Catalog of Small RNAs and Their Association with Distinct Argonaute/Piwi Family Members", Development 135 (7), 1201 (2008).
K.S. Kosik, "The Neuronal MicroRNA System", Nat. Rev. Neurosci, 7 (12), 911 (2006).
Landgraf et al., "A Mammalian MicroRNA Expression Atlas based on Small RNA Library Sequencing", Cell, 129 (7), 1401 (2007).
Kloosterman et al., "In Situ Detection of MiRNAs in Animal Embryos Using LNA-Modified Oligonucleotide Probes", Nat. Methods, 3 (1), 27 (2006).
Sokol et al., "Mesodermally Expressed *Drosophila* MicroNRA-1 is regulated by Twist and is Required in Muscles During Larval Growth", Genes Dev 19 (19) 2343 (2005).
Nelson et al., "RAKE and LNA-ISH Reveal MicroRNA Expression and Localization in Archival Human Brain", RNA, 12 (2), 187 (2006).
Silahtaroglu et al., "Detection of MicroRNAs in Frozen Tissue Sections by Fluorescence in Situ Hybridization Using Locked Nucleic Acid Probes and Tyramide Signal Amplification", Nat. Protoc, 2 (10), 2520 (2007).
Thompson et al., "Analysis of MicroRNA Expression by In Situ Hybridization with RNA Oligonucleotides Probes", Methods, 43 (2), 153 (2007).
G.J. Nuovo, "In Situ Detection of Precursor and Mature MicroRNAs in Paraffin Embedded, Formalin Fixed Tissues and Cell Preparations", Methods 44 (1), 39 (2008).
Bak et al., "MicroRNA Expression in the Adult Mouse Central NervSous System", RNA 14 (3), 432 (2008).
Sempere et al., "Altered MicroRNA Expression Confined to Specific Epithelial Cell Subpopulations in Breast Cancer", Cancer Res., 67 (24) 11612 (2007).
Wang, et al., "The Expression of MicroRNA miR-107 Decreases Early in Alzheimer's Disease and May Accelerate Disease Progression Through Regulation of Beta-Site Amyloid Precursor Protein-Cleaving Enzyme 1", J. Neurosci., 28 (5), 1213 (2008).
Schaefer et al., "Cerebellar Neurodegenertion in the Absence of MicroRNAs", J. Exp. Med, 204 (7), 1553 (2007).
Ryan et al., "MicroRNAs of the Mammalian Eye Display Distinct and Overlapping Tissue Specificity", Mol. Vis, 12, 1175 (2006).
Mansfield, et al., "MicroRNA-Responsive 'Sensor' Transgenes Uncover Hox-Like and other Developmentally regulated Patterns of Vertebrate MicroRNA Expression", Nat. Genet. 36 (10), 1079 (2004).
M.Y. Feldman, "Reactions of Nucleic Acids and Nucleoproteins with Formaldehyde", Prog. Nuclei Acid Res. Mol. Biol., 13, 1 (1973).
Masuda et al., "Analysis of Chemical Modification of RNA from Formalin-Fixed Samples and Optimization of Molecular Biology Applications for Such Samples", Nucleic Acids, Res., 27 (22) 4436, (1999).

(Continued)

*Primary Examiner* — Jezia Riley
(74) *Attorney, Agent, or Firm* — Hoffmann & Baron, LLP

(57) ABSTRACT

The invention provides a method for fixing an RNA molecule in a biological sample. The method comprises contacting the biological sample with an aldehyde-containing fixative, and subsequently contacting the sample with a solution comprising a carbodiimide and a heterocyclic derivative selected from the group consisting of an imidazole, pyrazole, triazole or tetrazole or a combination thereof. A method for differentiating cells in a biological sample is also provided. A method for quantification of RNA retention in a biological sample is also provided. A kit for fixing RNA in a sample is provided as well.

22 Claims, 59 Drawing Sheets

(56) References Cited

OTHER PUBLICATIONS

Tymianski et al., "A Novel Use for a Carbodiimide Compound for the Fixation of Fluorescent and Non-Fluorescent Calcium Indicators in Situ Following Physiological Experiments", Cell Calcium, 21 (3), 175 (1997).

Pall et al., "Carbodiimide-Mediated Cross-Linking of RNA to Nylon Membranes Improves the Detection of siRNA, miRNA and piRNA by Northern Blot", Nucleic Acids Res., 35 (8), e60 (2007).

Kaur et al., "Thermodynamics of DNA-RNA Heteroduplex Formation: Effects of Locked Nucleic Acid Nucleotides Incorporated into the DNA Strand", Nucleic Acids Symp. Ser., 52, 425 (2008).

Kye et al., "Somatodendritic MicroRNAs Identified by Laser Capture and Multiplex RT-PCR", RNA 13 (8), 1224 (2007).

M. Zuker, "Mfold Web Server for Nucleic Acid Folding and Hybridization Prediction", Nucleic Acids Res., 31 (13), 3406 (2003).

Danziger et al., "Tables of Distribution-Free Tolerance Limits", Annals of Mathematical Statistics, 35 (3), 1361 (1964).

Lein et al., "Genome-Wide Atlas of Gene Expression in the Adult Mouse Brain", Nature, 445 (7124) 168 (2007).

Abramoff et al., "Image Processing with ImageJ", Biophotonics International, 11 (7), 36 (2004).

Hafner et al., "Identification of MicroRNAs and other Small Regulatory RNAs Using cDNA Library Sequencing", Methods, 44 (1) 3, (2008).

Chu, et al., "Derivatization of Unprotected Polynucleotides", Nucleic Acids Research, 11 (6), 6513 (1983).

Tech Tip #30, "Modify and Label Oligonucleotide 5' Phosphate Groups", Pierce Biotechnology, Inc. pp. 1-2 (2006).

Tuschl et al., "Keystone Seminar" pp. 1-35, Mar. 28, 2008.

Pena et al., Nature Methods 6 (2), 139 (2009).

Ahern, The Scientist 9 (15), 20, (1995).

* cited by examiner

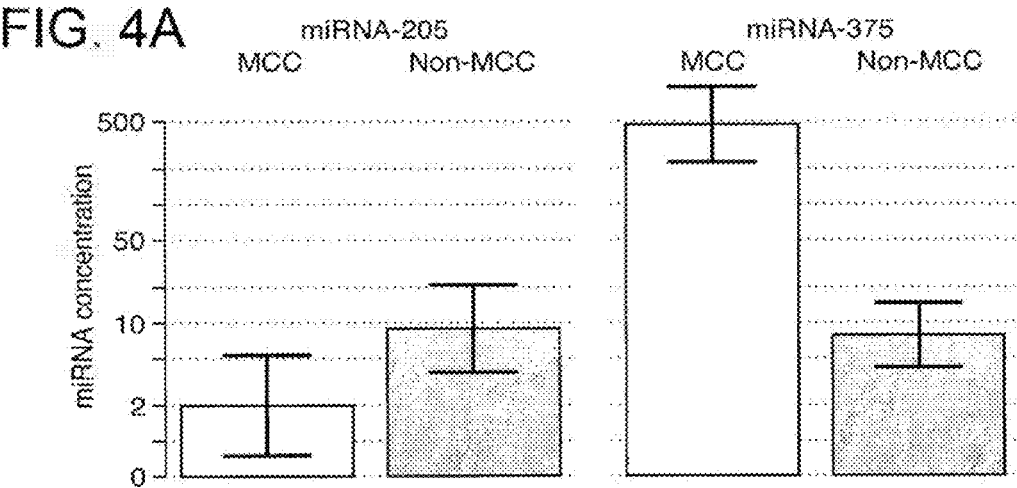
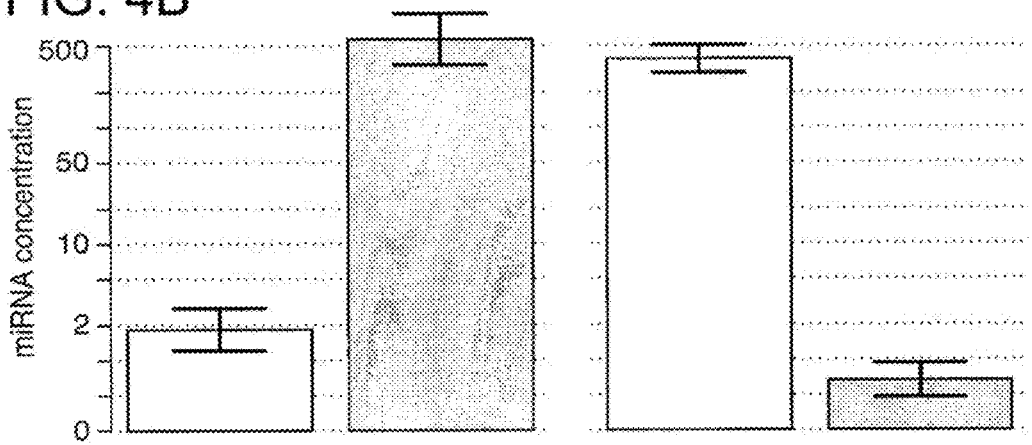
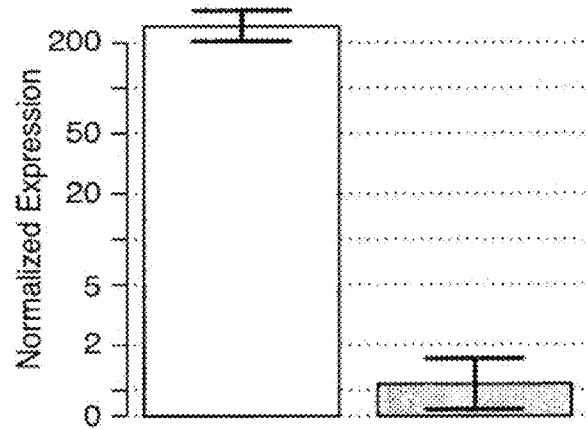

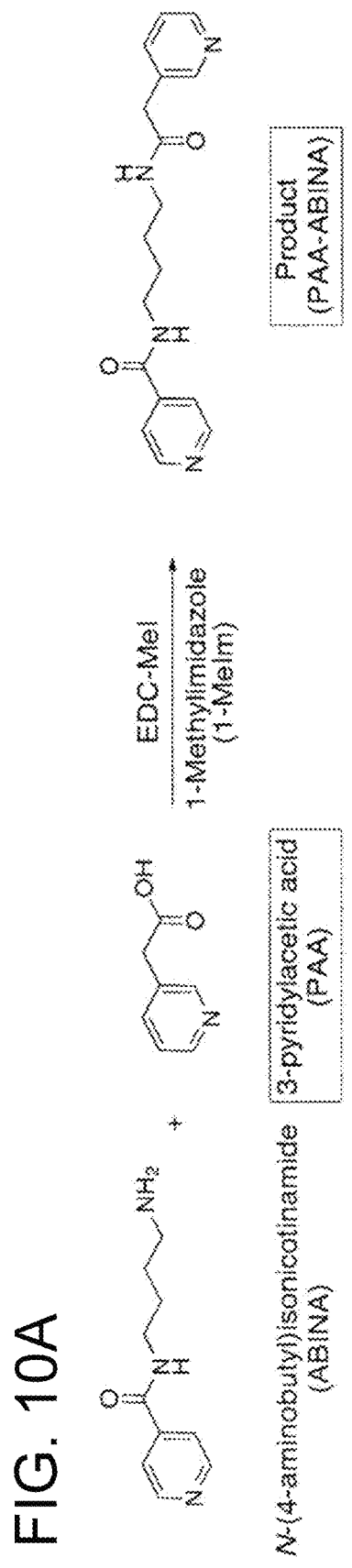

FIG. 12A

| Linker sequence | Length (nm) |
|---|---|
| LNA-[p-O-(CH$_2$)$_6$-NH]-biotin | 1.2 |
| LNA-X-biotin | 3 |
| LNA-(A)$_{10}$-X-biotin<br>LNA-(T)$_{10}$-X-biotin<br>LNA-(Abasic)$_{10}$-X-biotin<br>LNA-Y-X-biotin<br>LNA-Z$_4$-X-biotin | 6 |
| LNA-Y$_2$-X-biotin<br>LNA-Z$_3$-X-biotin | 9 |
| LNA-Z$_5$-X-biotin | 10.5 |
| LNA-Y$_3$-X-biotin<br>LNA-Z$_6$-X-biotin | 12 |
| LNA-Y$_5$-X-biotin<br>LNA-Z$_{10}$-X-biotin | 18 |
| LNA-Y$_7$-X-biotin | 24 |
| LNA-Y$_{10}$-X-biotin | 33 |

FIG. 12B

Linker abbreviations

X = NH-CH$_2$-[(CH$_2$)$_2$-O]$_3$-(CH$_2$)$_3$-NHCO-CH$_2$-O-CH$_2$-NHCO-(CH$_2$)$_2$-O-p
Y = O-(CH$_2$)$_2$-O-[(CH$_2$)$_2$-O]$_4$-(CH$_2$)$_2$-O-p
Z = O-(CH$_2$)$_2$-O-(CH$_2$)$_2$-O-(CH$_2$)$_2$-O-p
p = phosphodiester linkage

| Sample name | Sample type | Year of fixation | RNA extraction method | Spectrophotometer | Total RNA concentration (ng/μl) | A260/A280 ratio | RNA integrity | Immunostaining | MCV status | Percent tumor |
|---|---|---|---|---|---|---|---|---|---|---|
| MCC1 | FFPE tissue punch | 2008 | Ambion Recoverall | Nanodrop | 1.60 | 1.92 | Partially degraded | CK20+, CHR+, SYN+ | Negative | 75 |
| MCC2 | FFPE tissue punch | 2008 | Ambion Recoverall | Nanodrop | 0.88 | 2.00 | Partially degraded | CK20+ | Positive | 25 |
| MCC3 | FFPE tissue punch | 2007 | Ambion Recoverall | Nanodrop | 1.12 | 2.00 | Partially degraded | CK20+, S100- | Negative | 75 |
| MCC4 | FFPE tissue punch | 2006 | Ambion Recoverall | Nanodrop | 1.24 | 1.94 | Partially degraded | CK20+, CK7+, S100- | Positive | 50 |
| MCC5 | FFPE tissue punch | 2006 | Ambion Recoverall | Nanodrop | 0.96 | 2.00 | Partially degraded | CK20+, EMA+ | Negative | 75 |
| MCC6 | FFPE tissue punch | 2006 | Ambion Recoverall | Nanodrop | 0.64 | 2.00 | Partially degraded | CK20+, LCA- | Positive | 90 |
| MCC7 | FFPE tissue punch | 2006 | Ambion Recoverall | Nanodrop | 0.88 | 2.00 | Partially degraded | CK20+, CK7-, SYN+ | Positive | 75 |
| MCC8 | FFPE tissue punch | 2005 | Ambion Recoverall | Nanodrop | 0.44 | 1.83 | Partially degraded | CK20-, LMWK+, SYN+ | Negative | 50 |
| MCC9 | FFPE tissue punch | 2005 | Ambion Recoverall | Nanodrop | 2.44 | 1.91 | Partially degraded | CK20+, CK7-, CHR+, LMWK+, SYN+, TTF1- | Positive | 75 |
| MCC10 | FFPE tissue punch | 2004 | Ambion Recoverall | Nanodrop | 1.28 | 1.88 | Partially degraded | CK20+, CK7-, CHR+, LMWK+, NSE+, S100- | Positive | 65 |
| MCC11 | FFPE tissue punch | 2003 | Ambion Recoverall | Nanodrop | 0.56 | 2.00 | Partially degraded | CK20+, LMWK+ | Indeterminate | 85 |
| MCC12 | FFPE tissue punch | 2001 | Ambion Recoverall | Nanodrop | 1.20 | 2.00 | Partially degraded | CK20+, CK7-, CEA+, LMWK+, NSE+, SYN+ | Positive | 50 |
| NS1 | FFPE tissue punch | 2008 | Ambion Recoverall | Nanodrop | 0.28 | 1.75 | Partially degraded | NT | Positive | NA |
| NS2 | FFPE tissue punch | 2007 | Ambion Recoverall | Nanodrop | 0.36 | 1.88 | Partially degraded | NT | Indeterminate | NA |
| NS3 | FFPE tissue punch | 2005 | Ambion Recoverall | Nanodrop | 0.36 | 2.25 | Partially degraded | NT | Indeterminate | NA |
| NS4 | FFPE tissue punch | 2006 | Ambion Recoverall | Nanodrop | 0.36 | 2.25 | Partially degraded | NT | Negative | NA |
| BCC1 | FFPE tissue punch | 2008 | Ambion Recoverall | Nanodrop | 0.28 | 1.75 | Partially degraded | NT | Negative | 20 |
| BCC2 | FFPE tissue punch | 2008 | Ambion Recoverall | Nanodrop | 0.52 | 2.17 | Partially degraded | NT | Negative | 75 |
| BCC3 | FFPE tissue punch | 2008 | Ambion Recoverall | Nanodrop | 1.12 | 2.09 | Partially degraded | NT | Negative | 95 |
| BCC4 | FFPE tissue punch | 2008 | Ambion Recoverall | Nanodrop | 0.28 | 2.33 | Partially degraded | NT | Negative | 75 |
| MCC13a | FFPE tissue roll | 2007 | Epicenter Masterpure | SmartSpec | 0.48 | 1.58 | Partially degraded | CK20+, CHR+, SYN+, NF-, TTF1- | NT | 80 |
| MCC13b | FFPE tissue roll | 2007 | Epicenter Masterpure | SmartSpec | 0.64 | 1.69 | Partially degraded | CK20+, CHR+, SYN+, NF-, TTF1- | NT | 80 |
| MCC14a | FFPE tissue roll | 2007 | Epicenter Masterpure | SmartSpec | 1.40 | 1.75 | Partially degraded | CK20+, CK7-, NSE+ | NT | 80 |
| MCC14b | FFPE tissue roll | 2007 | Epicenter Masterpure | SmartSpec | 1.80 | 1.73 | Partially degraded | CK20+, CK7-, NSE+ | NT | 80 |
| NS5a | FFPE tissue roll | 2008 | Epicenter Masterpure | SmartSpec | 0.01 | 1.99 | Partially degraded | NT | NT | NA |
| NS5b | FFPE tissue roll | 2008 | Epicenter Masterpure | SmartSpec | 0.06 | 2.00 | Partially degraded | NT | NT | NA |
| BCC5a | FFPE tissue roll | 2008 | Epicenter Masterpure | SmartSpec | 0.44 | 1.83 | Partially degraded | NT | NT | 80 |
| BCC5b | FFPE tissue roll | 2008 | Epicenter Masterpure | SmartSpec | 0.52 | 1.63 | Partially degraded | NT | NT | 80 |
| MKL-1a | Cell line | Not fixed | TRIzol Reagent | SmartSpec | 0.83 | 1.59 | Intact | NT | Positive | NA |
| MCC13 | Cell line | Not fixed | TRIzol Reagent | SmartSpec | 0.33 | 1.84 | Intact | NT | Negative | NA |
| MCC28 | Cell line | Not fixed | TRIzol Reagent | SmartSpec | 0.81 | 1.98 | Intact | NT | Negative | NA |
| MS-1 | Cell line | Not fixed | TRIzol Reagent | SmartSpec | 0.94 | 1.73 | Intact | NT | Positive | NA |
| MKL-1b | Cell line | Not fixed | TRIzol Reagent | SmartSpec | 1.47 | 1.61 | Intact | NT | Positive | NA |
| U820 | Cell line | Not fixed | TRIzol Reagent | SmartSpec | 2.90 | 1.68 | Intact | NT | Negative | NA |
| MKL-1c | Cell line | Not fixed | TRIzol Reagent | SmartSpec | 2.03 | 1.60 | Intact | NT | Positive | NA |
| MKL-2 | Cell line | Not fixed | TRIzol Reagent | SmartSpec | 3.65 | NA | Intact | NT | Positive | NA |

FIG. 17

| Sample name | Sequencing run | Total reads | Calibrator | miRNA | % miRNA | None | % None | tRNA | % rRNA | tRNA | % tRNA | MiscRNA | % MiscRNA | Marker | % Marker |
|---|---|---|---|---|---|---|---|---|---|---|---|---|---|---|---|
| MCC1 | 1 | 346,160 | 213,207 | 108,829 | 81.9 | 10,084 | 7.6 | 6,248 | 4.7 | 5,886 | 4.4 | 1,776 | 1.3 | 30 | 0.0 |
| MCC2 | 1 | 269,529 | 163,366 | 83,392 | 79.0 | 7,479 | 7.1 | 6,374 | 6.0 | 6,150 | 5.8 | 2,140 | 2.0 | 34 | 0.0 |
| MCC3 | 1 | 463,784 | 184,574 | 237,241 | 85.0 | 19,242 | 6.9 | 8,428 | 3.0 | 10,696 | 3.8 | 3,494 | 1.3 | 9 | 0.0 |
| MCC4 | 1 | 508,423 | 223,255 | 233,477 | 81.9 | 16,275 | 5.7 | 16,475 | 5.8 | 15,165 | 5.3 | 3,748 | 1.3 | 5 | 0.0 |
| MCC5 | 1 | 397,029 | 209,520 | 143,966 | 78.8 | 13,934 | 7.4 | 17,040 | 9.1 | 8,264 | 4.4 | 4,399 | 2.3 | 6 | 0.0 |
| MCC6 | 1 | 433,934 | 220,098 | 150,143 | 70.2 | 18,766 | 8.8 | 23,286 | 10.9 | 14,475 | 6.8 | 7,140 | 3.3 | 26 | 0.0 |
| MCC7 | 1 | 308,621 | 158,251 | 119,650 | 80.0 | 10,787 | 7.3 | 8,868 | 6.0 | 7,954 | 5.4 | 2,169 | 1.4 | 4 | 0.0 |
| MCC8 | 1 | 401,743 | 191,749 | 163,928 | 78.1 | 13,317 | 6.3 | 15,339 | 7.3 | 14,603 | 7.0 | 2,802 | 1.3 | 6 | 0.0 |
| MCC9 | 1 | 418,710 | 211,000 | 144,291 | 69.5 | 20,148 | 9.7 | 19,985 | 9.6 | 15,836 | 7.6 | 7,433 | 3.6 | 15 | 0.0 |
| MCC10 | 1 | 475,659 | 231,104 | 138,293 | 58.5 | 35,767 | 15.0 | 35,390 | 14.5 | 22,043 | 9.0 | 12,053 | 4.9 | 9 | 0.0 |
| MCC11 | 1 | 351,074 | 177,461 | 119,249 | 68.7 | 17,209 | 9.9 | 19,685 | 11.3 | 13,397 | 7.7 | 4,086 | 2.3 | 26 | 0.0 |
| MCC12 | 1 | 275,277 | 145,448 | 71,979 | 55.0 | 11,952 | 9.2 | 26,093 | 21.6 | 13,629 | 10.5 | 4,769 | 3.7 | 7 | 0.0 |
| NS1 | 1 | 226,487 | 183,158 | 122,368 | 65.4 | 6,377 | 4.4 | 8,055 | 5.6 | 5,574 | 3.9 | 916 | 0.6 | 39 | 0.0 |
| NS2 | 1 | 121,271 | 65,628 | 47,771 | 85.9 | 2,837 | 4.7 | 2,968 | 5.3 | 1,889 | 3.4 | 375 | 0.7 | 23 | 0.0 |
| NS3 | 1 | 227,323 | 129,639 | 67,506 | 69.5 | 6,236 | 6.4 | 12,847 | 13.2 | 9,189 | 9.5 | 1,275 | 1.3 | 29 | 0.0 |
| NS4 | 1 | 371,336 | 207,777 | 130,295 | 79.7 | 7,930 | 4.8 | 16,388 | 10.0 | 7,316 | 4.5 | 1,620 | 1.0 | 29 | 0.0 |
| BCC1 | 1 | 413,375 | 183,123 | 206,096 | 88.5 | 10,338 | 4.5 | 6,741 | 2.9 | 5,321 | 2.3 | 1,706 | 0.7 | 48 | 0.0 |
| BCC2 | 1 | 447,357 | 207,843 | 217,614 | 90.9 | 10,233 | 4.3 | 4,929 | 2.1 | 5,456 | 2.3 | 1,251 | 0.5 | 31 | 0.0 |
| BCC3 | 1 | 478,255 | 217,634 | 239,447 | 91.9 | 11,100 | 4.3 | 5,586 | 2.1 | 2,774 | 1.1 | 1,660 | 0.6 | 44 | 0.0 |
| BCC4 | 1 | 556,983 | 218,261 | 308,249 | 91.0 | 10,763 | 3.2 | 10,479 | 3.1 | 7,256 | 2.1 | 1,942 | 0.6 | 36 | 0.0 |
| MCC13a | 2 | 487,374 | 175,636 | 287,241 | 66.5 | 22,355 | 7.2 | 32,641 | 10.5 | 39,365 | 12.8 | 8,562 | 2.7 | 364 | 0.3 |
| MCC13b | 2 | 398,202 | 124,398 | 185,175 | 67.6 | 19,730 | 7.2 | 27,864 | 10.2 | 32,462 | 11.9 | 7,745 | 2.8 | 848 | 0.3 |
| MCC14a | 2 | 309,206 | 144,867 | 181,900 | 62.0 | 26,961 | 16.4 | 12,685 | 7.4 | 18,601 | 11.3 | 4,422 | 2.7 | 370 | 0.2 |
| MCC14b | 2 | 193,036 | 152,228 | 18,724 | 45.8 | 10,294 | 25.2 | 5,050 | 12.4 | 4,597 | 11.2 | 2,123 | 5.2 | 77 | 0.2 |
| NS5a | 2 | 242,202 | 204,422 | 27,485 | 72.8 | 3,575 | 9.5 | 2,911 | 7.7 | 3,097 | 8.2 | 385 | 1.0 | 327 | 0.9 |
| NS5b | 2 | 245,432 | 201,504 | 31,921 | 72.7 | 3,577 | 8.1 | 2,902 | 6.6 | 3,929 | 8.9 | 329 | 0.7 | 1180 | 2.7 |
| BCC5a | 2 | 649,145 | 162,408 | 401,500 | 82.5 | 14,056 | 2.9 | 29,080 | 6.2 | 38,735 | 7.3 | 4,876 | 1.0 | 592 | 0.1 |
| BCC5b | 2 | 550,843 | 188,053 | 319,392 | 83.4 | 13,450 | 3.5 | 17,556 | 4.6 | 28,533 | 7.5 | 3,666 | 1.0 | 283 | 0.1 |
| MKL1a | 2 | 537,480 | 139,582 | 361,783 | 80.9 | 15,635 | 3.9 | 3,428 | 0.9 | 12,297 | 3.1 | 3,906 | 1.0 | 781 | 0.2 |
| MKL1a | 2 | 372,321 | 140,858 | 216,435 | 93.6 | 7,382 | 3.2 | 679 | 0.3 | 5,480 | 2.4 | 719 | 0.3 | 648 | 0.3 |
| MCC29a | 2 | 327,222 | 177,471 | 130,673 | 87.3 | 9,115 | 6.1 | 1,270 | 0.8 | 6,055 | 4.0 | 1,167 | 0.8 | 1469 | 1.0 |
| MS1 | 2 | 588,366 | 107,475 | 448,106 | 93.2 | 13,167 | 2.7 | 4,138 | 0.9 | 8,737 | 1.8 | 5,698 | 1.2 | 1085 | 0.2 |
| MKL1b | 2 | 845,227 | 152,483 | 434,595 | 88.2 | 21,066 | 4.3 | 4,679 | 0.9 | 17,222 | 3.5 | 13,920 | 2.8 | 1261 | 0.3 |
| U150 | 2 | 364,004 | 199,572 | 150,539 | 91.6 | 7,813 | 4.8 | 1,106 | 0.7 | 2,673 | 1.7 | 676 | 0.4 | 1423 | 0.9 |
| MKL1c | 2 | 356,963 | 138,724 | 197,841 | 89.8 | 10,119 | 4.6 | 2,827 | 1.3 | 5,404 | 2.5 | 2,903 | 1.3 | 1142 | 0.5 |
| MKL2 | 2 | 391,740 | 168,396 | 193,668 | 85.3 | 12,266 | 6.5 | 3,277 | 1.5 | 10,951 | 5.8 | 3,082 | 1.4 | 1200 | 0.5 |

| Carbodiimide derivative | Reaction time (h) | Reaction temperature (°C) | Optimal reaction pH |
|---|---|---|---|
| Ethyl-3-(3-dimethylaminopropyl)carbodiimide hydrochloride (EDC-HCl) | 28 | 25 | 8.0 |
| | 7 | 50 | 8.0 |
| Ethyl-3-(3-dimethylaminopropyl)carbodiimide methiodide (EDC-MeI) | 12 | 25 | 8.0 |
| | 3 | 50 | 7.5 |
| N-Cyclohexyl-N'-(2-morpholinoethyl)carbodiimide metho-p-toluenesulfonate (CMC) | 10 | 50 | 7.5 |
| N,N'-Diisopropylcarbodiimide (DIC) | 24 | 50 | 8.0 |

FIG. 20
| Heterocyclic derivative | Reaction time (h) | Reaction temperature (°C) | Optimal reaction pH |
|---|---|---|---|
|  2-Methylimidazole pKa ~ 7.8 | 14 | 50 | 8.0 |
|  Imidazole pKa ~ 7.0 | 11 | 50 | 7.5 - 8.0 |
|  1-Hydroxy-benzotriazole pKa ~ 5.0 | 4 | 50 | 8.0 - 8.5 |
| 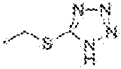 5-Ethylthio-1H-tetrazole pKa ~ 4.3 | 3 | 50 | 8.0 |
|  2-Chloroimidazole pKa ~ 2.0 | 15 | 50 | 8.0 |

FIG. 21A

| Probe | Lenght (nt) | Antisense probe | Tm (°C) |
|---|---|---|---|
| hsa-miR-205 LNA | 22 | 5' CaGaCTCCGGtGGAatGaaGGa | 70.7 |
| hsa-miR-205 DNA | 22 | 5' CAGACTCCGGTGGAATGAAGGA | 41.3 |
| hsa-miR-205 LNA | 14 | 5' GGTGGAtgaAgga | 61.6 |
| hsa-miR-205 LNA | 14 | 5' GGTGGAAtGaAggA | 58.5 |
| hsa-miR-205 DNA | 14 | 5' GGTGGAATGAAGGA | 33.1 |
| hsa-miR-375 LNA | 22 | 5' tCaCGCGAgcCGAAcgAaCaAa | 73.0 |
| hsa-miR-375 DNA | 22 | 5' TCACGCGAGCCGAACGAACAAA | 38.2 |
| hsa-miR-375 LNA | 15 | 5' agcCGaaCGaAcaaA | 75.9 |
| hsa-miR-375 LNA | 15 | 5' AGCCGaaCGaAcaaA | 62.1 |
| hsa-miR-375 LNA | 15 | 5' aGCCGAaCGaACaAa | 53.8 |
| hsa-miR-375 LNA | 15 | 5' aGCCGaACgAacAAa | 63.3 |
| hsa-miR-375 DNA | 15 | 5' AGCCGAACGAACAAA | 30.3 |

FIG. 21B

| Probe | Lenght (nt) | Antisense probe | Tm (°C) |
|---|---|---|---|
| hsa-rRNA LNA1 | 17 | 5' CTttTCtGggGTcTGaT | 83.5 |
| hsa-rRNA LNA2 | 15 | 5' TCCcGtCCgTTCCG | 78.5 |
| hsa-rRNA LNA3 | 18 | 5' CATCTcTcAGGAcCgAcT | 77.3 |
| hsa-rRNA LNA4 | 17 | 5' GGTtCctCtCGtACTgA | 78.2 |

FIG. 25

| Sample name | miR-375 (mean intensity) | sum of pixels* | exposure (ms) | miR-205 (mean intensity) | sum of pixels* | exposure (ms) | rRNA (mean intensity) | sum of pixels* | exposure (ms) | miR-375 (normalized)# | miR-205 (normalized)# |
|---|---|---|---|---|---|---|---|---|---|---|---|
| MCC1 | 2207 | 78835 | 50 | 1090 | 1724 | 100 | 1196 | 72829 | 250 | 2.00 | 0.02 |
| MCC2 | 2170 | 12005877 | 50 | 2017 | 539306 | 100 | 4085 | 12147745 | 250 | 0.53 | 0.02 |
| MCC3 | 5411 | 123320 | 50 | 1215 | 12024 | 100 | 3272 | 113299 | 250 | 1.65 | 0.04 |
| MCC4 | 2587 | 132879 | 50 | 1358 | 1921 | 100 | 2471 | 131663 | 250 | 1.06 | 0.01 |
| MCC5 | 2215 | 131862 | 50 | 1426 | 9376 | 100 | 2009 | 130468 | 250 | 1.11 | 0.05 |
| MCC6 | 2379 | 156358 | 50 | 1590 | 6079 | 100 | 2355 | 157611 | 250 | 1.00 | 0.03 |
| MCC7 | 6956 | 11402977 | 50 | 1819 | 1751522 | 100 | 2571 | 11213780 | 250 | 2.59 | 0.11 |
| MCC8 | 3770 | 10097631 | 50 | 1450 | 634629 | 100 | 3574 | 10097360 | 250 | 0.91 | 0.03 |
| MCC9 | 1924 | 13851031 | 50 | 1889 | 156289 | 100 | 2591 | 11438599 | 250 | 0.90 | 0.01 |
| MCC10 | 2538 | 72267 | 50 | 1379 | 3478 | 100 | 5431 | 71732 | 250 | 0.47 | 0.01 |
| MCC11 | 2134 | 14803085 | 50 | 1627 | 557850 | 100 | 2640 | 14805770 | 250 | 0.81 | 0.02 |
| MCC12 | 1802 | 12550860 | 50 | 1544 | 253568 | 100 | 4211 | 12550930 | 250 | 0.43 | 0.01 |
| MCC13 | 2160 | 9513945 | 50 | 1443 | 508613 | 100 | 3099 | 10293898 | 250 | 0.64 | 0.02 |
| BCC1 | 21 | 16 | 50 | 1967 | 59684 | 100 | 1889 | 68082 | 250 | 0.00 | 0.91 |
| BCC2 | 33 | 1347 | 50 | 1642 | 13678440 | 100 | 1616 | 14872308 | 250 | 0.00 | 0.93 |
| BCC3 | 12 | 22 | 50 | 1099 | 79182 | 100 | 832 | 99121 | 250 | 0.00 | 1.06 |
| BCC4 | 1040 | 865 | 50 | 1755 | 69873 | 100 | 1641 | 72460 | 250 | 0.01 | 1.03 |
| BCC5 | 1162 | 306310 | 50 | 1387 | 10758779 | 100 | 755 | 8360325 | 250 | 0.06 | 2.36 |

* sum of pixels above defined threshold, encompassing interval from 1,000 to 10,000 pixel intensities

(mean intensity of miRNA*pixel count)/(mean intensity of rRNA*pixel count)

FIG. 26

| Target | Fluorescent dye | Ex. | Em. | QY | Filter |
|---|---|---|---|---|---|
| Nuclei/DNA | DAPI | 353 nm | 460 nm | 0.60 | 310 nm - 390 nm (Ex.)<br>430 nm - 480 nm (Em.) |
| miR-375 | ATTO 488 | 500 nm | 523 nm | 0.80 | 475 nm - 505 nm (Ex.)<br>505 nm - 550 nm (Em.) |
| miR-205 | ATTO 532 | 532 nm | 553 nm | 0.90 | 535 nm - 575 nm (Ex.)<br>570 nm - 650 nm (Em.) |
| rRNA | ATTO 647N | 644 nm | 669 nm | 0.65 | 620 nm - 650 nm (Ex.)<br>660 nm - 705 nm (Em.) |

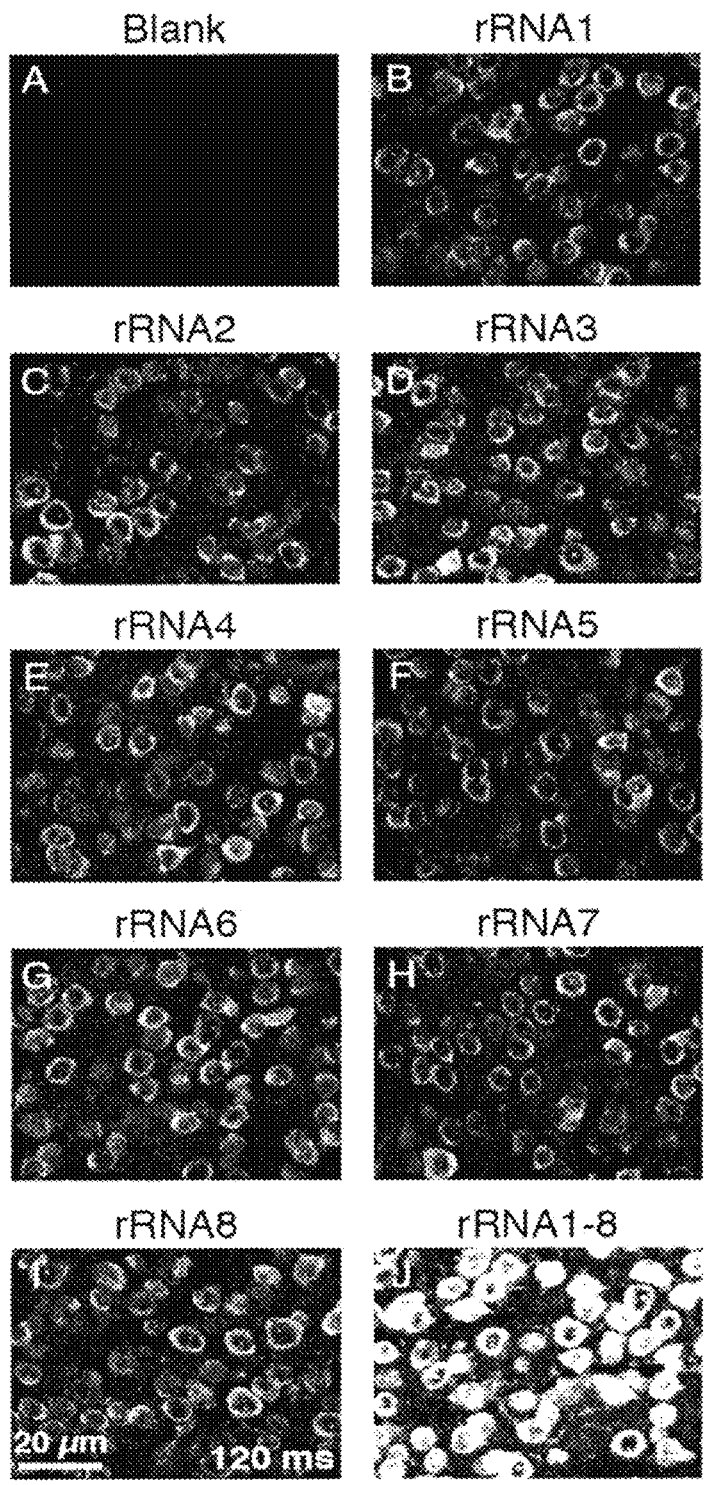

FIG. 35

| Probe | Length (nt) | rRNA sequence (mmu 28S rRNA) | Position | LNA sequence | Intensity | Tm (°C) |
|---|---|---|---|---|---|---|
| Blank | | | | | 572 | |
| rRNA1 | 20 | GGAAAGAAACTAACCAGGA | 57-76 | TCcTGgTtAgTtcTtTTCC | 58320 | |
| rRNA2 | 17 | ATCAGACCCCAGAAAAG | 1731-1747 | CTtTCtGggGTcTGaT | 54104 | 78.1 |
| rRNA3 | 20 | CTAAGGAGTGTGTAACAACT | 1798-1817 | AGTtGTtACaCACTcCTaG | 71824 | |
| rRNA4 | 19 | CTGAAAATGGATGGCGCTG | 1839-1857 | CAGcGCcATcCAtTTtCAG | 59983 | |
| rRNA5 | 15 | CGGAACGGGACGGA | 1897-1911 | TCCcgTcCCgTTCCg | 53829 | 71.8 |
| rRNA6 | 18 | AGTCGGTCCTGAGAGATG | 2193-2210 | CATcTcTcAGgAcCgAcT | 63003 | 71.3 |
| rRNA7 | 16 | GGAGCAGAAGGGCAAA | 3918-3933 | TtTgGCccTtCTgCtCc | 57460 | |
| rRNA8 | 17 | TCAGTACGAGAGAGGAACC | 4249-4265 | GGTtCcTcCgTaCTgA | 69603 | 70.6 |
| rRNA1-8 | | | | | 469068 | |

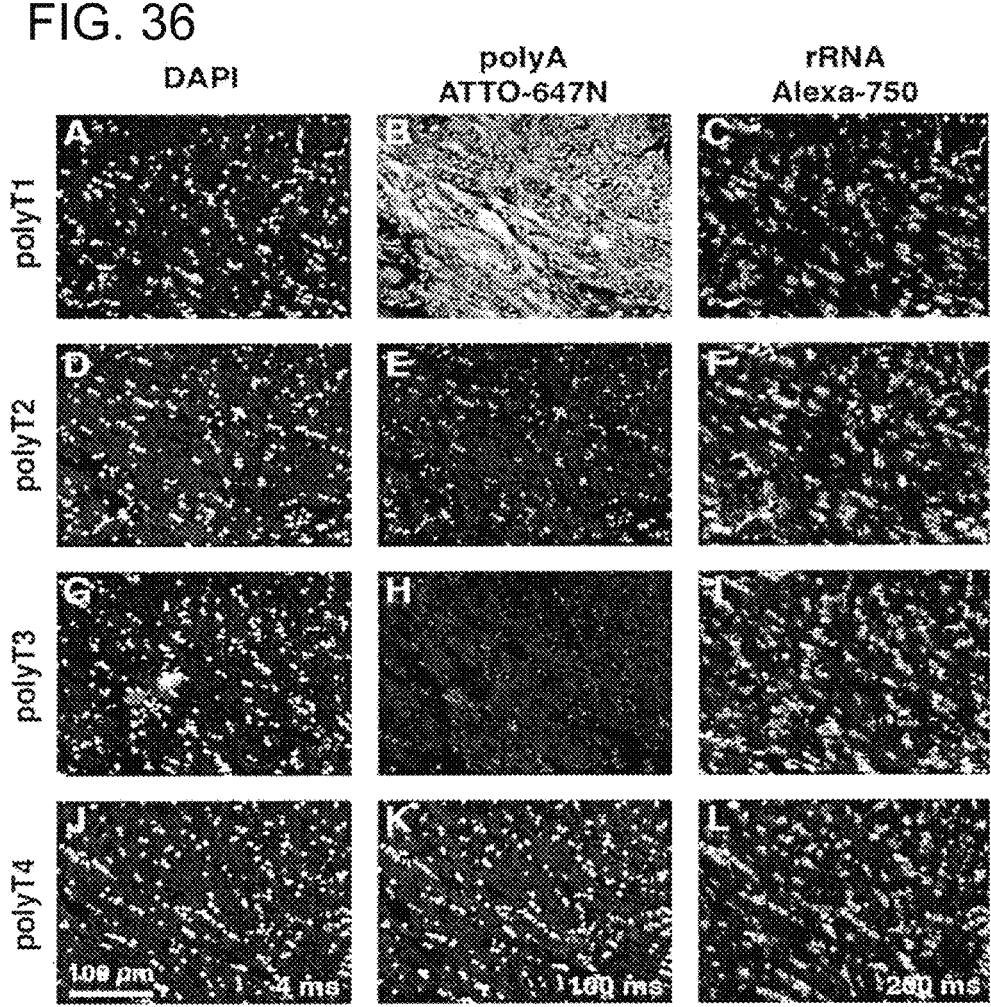

FIG. 37

| | LNA sequence | Length | Norm. intensity | Tm (°C) |
|---|---|---|---|---|
| polyT1 | TtTtTtTtTtTtTtTtTtTtTtTtTtTtTtT | 30-mer | 30.15 | 49.5 |
| polyT2 | TtTtTtTtTtTtTtTtTtTtT | 21-mer | 8.72 | |
| polyT3 | TtTTtTtTTtTtTTtTtTTtT | 21-mer | 4.34 | |
| polyT4 | TtttTtttTtttTtttTtttT | 21-mer | 16.16 | |

FIG. 38

| RNA category | Name | Transcript length (nt) | Read counts (Mio) | Read counts/ transcript length | Normalized Intensity from RNA FISH |
|---|---|---|---|---|---|
| rRNA | 5S | 121 | 10.6 | 8.78E+04 | |
| rRNA | 5.8S | 156 | 10.9 | 6.99E+04 | |
| rRNA | 18S | 1,889 | 45.2 | 2.42E+04 | |
| rRNA | 28S | 5,070 | 84.5 | 1.67E+04 | 2.15E+07 |
| scRNA | hY3 | 102 | 1.28 | 1.25E+04 | 1.03E+07 |
| snRNA | U1 | 164 | 1.63 | 9.94E+03 | 8.60E+06 |
| snRNA | U3 | 217 | 2.08 | 9.60E+03 | 3.00E+06 |
| snRNA | U2 | 188 | 1.57 | 8.35E+03 | 5.51E+06 |
| mt-rRNA | 16S | 1,559 | 5.84 | 3.62E+03 | 3.92E+06 |
| snRNA | U6 | 106 | 0.31 | 2.92E+03 | |
| scRNA | 7SL | 299 | 0.75 | 2.51E+03 | 2.95E+06 |
| mt-rRNA | 12S | 954 | 2.20 | 2.31E+03 | 3.52E+06 |
| snRNA | 7SK | 332 | 0.25 | 7.53E+02 | |
| mt-mRNA | COX1 | 1,542 | 0.64 | 4.15E+02 | |
| mt-mRNA | COX2 | 684 | 0.19 | 2.78E+02 | |
| mRNA | ACTB | 1,852 | 0.04 | 2.16E+01 | |
| mRNA | RPL8 | 903 | 0.01 | 1.11E+01 | |
| mRNA | EEF2 | 3,163 | 0.033 | 1.04E+01 | |

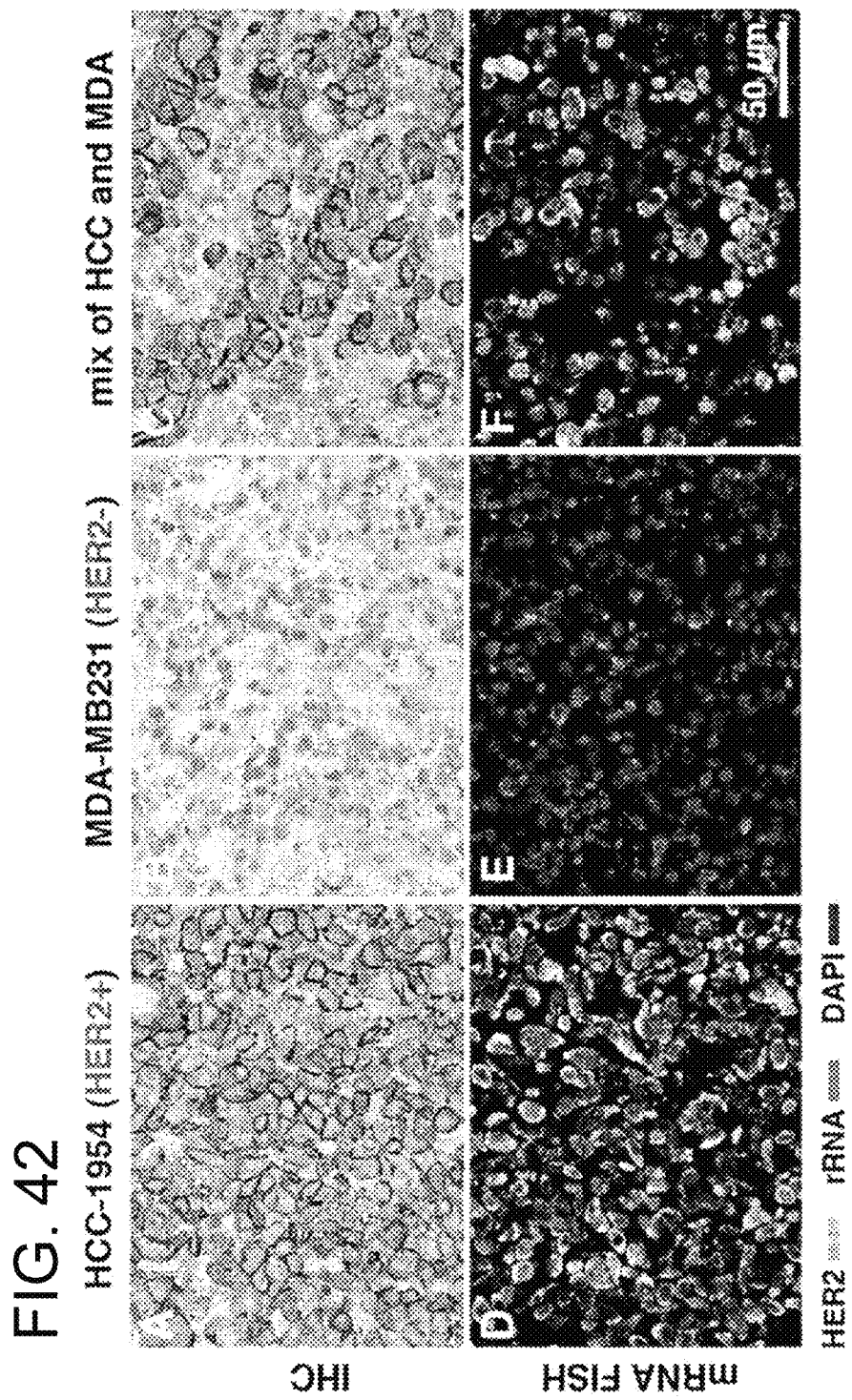

FIG. 43

| RNA category | Probe | Length (nt) | RNA Sequence | LNA sequence |
|---|---|---|---|---|
| hsa/mmu-28S rRNA | 1 | 17 | AGGAGUGUGUAACAACU | Z-aGTtGTtaCaCaCTCCt-Y |
| | 2 | 17 | CUGAAAAUGGAUGGCGC | Z-GCGCCaTCCaTtTtCaG-Y |
| | 3 | 17 | GUCGGUCCUGAGAGAUG | Z-CaTCtCtCaGGaCCGaC-Y |
| | 4 | 17 | GUACCCAUAUCCGCAGC | Z-GCTGCGGAtatGGGtaC-Y |
| | 5 | 17 | UCAGUACGAGAGGAACC | Z-GGTtCCtCtCGtACTGa-Y |
| hsa-mt-rRNA | 1 | 17 | UUGGUCCUAGCCUUUCU | Z-aGaaaGGCtAGGACCaa-Y |
| | 2 | 17 | AACUAAGCUAUACUAAC | Z-GTtaGTaTaGCTtaGTt-Y |
| | 3 | 17 | GGUCACACGAUUAACCC | Z-GGGTTaaTCGTGtGaCC-Y |
| | 4 | 17 | GCCAUCUUCAGCAAACC | Z-GGTtGCtGAaGAtGGC-Y |
| | 5 | 17 | AAGACGUUAGGUCAAGG | Z-CCttGaCCtAaCGTCtT-Y |
| | 6 | 17 | AGGCUACAAAGUAAGCG | Z-CGCtTaCtTtGTAGCCt-Y |
| | 7 | 17 | CUACCAGACAACCUUAG | Z-CTaaGGTtGtCTGGtaG-Y |
| | 8 | 17 | CAGCUAAAAGAGCACAC | Z-GtGTGCTCTTtAGCtG-Y |
| | 9 | 17 | GGUUGUCCAAGAUAGAA | Z-TtCtaTCTtGGaCaaCC-Y |
| | 10 | 17 | UCCUCACACCCAAUUGG | Z-CCaAttGGGTGTGaGGa-Y |
| | 11 | 17 | AAAACAUCACCUCUAGC | Z-GCTaGaGGtGatGTtTT-Y |
| | 12 | 17 | AACAGUACCUAACAAAC | Z-GtTtGTtaGGtACtGTt-Y |
| mmu-mt-rRNA | 1 | 15 | GAGGGUAUCAAGCAC | Z-GtGCtTGaTACCCtC-Y |
| | 2 | 15 | GGCGUAAAACGUGUC | Z-GaCaCGttTtaCGCC-Y |
| | 3 | 15 | GCCAUCUUCAGCAAA | Z-TttGCtGaaGAtGGC-Y |
| | 4 | 15 | CCACUAUGCUUAGCC | Z-GGCtAaGCATaGtGG-Y |
| | 5 | 15 | GGACUCAGCAGUGAU | Z-atCACTGCTGaGtCC-Y |
| | 6 | 15 | CUCCAGGCAUACGCG | Z-CGCGtAtGCCTGGaG-Y |
| | 7 | 15 | CAAGAGAAAUAGAGC | Z-GCtCtaTTtCtCttG-Y |
| | 8 | 15 | CUGUUAACCCUGUUAG | Z-GtGTtGGGTTaaCaG-Y |
| | 9 | 15 | AUGCAACACUGUUAG | Z-CTaaCaGtGTtGCaT-Y |
| | 10 | 15 | CCUACGUGAUCUGAG | Z-CtCaGaTCaCGTaGG-Y |

FIG. 43 Continued

| RNA category | Probe | Length (nt) | RNA Sequence | LNA sequence |
|---|---|---|---|---|
| hsa-U1 snRNA | 1 | 12 | GGAGAUACCAUG | Z-CatGGTaTCtCC-Y |
| | 2 | 14 | GAGGCUUAUCCAUU | Z-aAtGGAtaAGCCtC-Y |
| | 3 | 12 | GGAUGUGCUGAC | Z-GtCAGCACAtCC-Y |
| | 4 | 12 | UGCGAUUCCCC | Z-GGGGaaatCGCa-Y |
| | 5 | 14 | GCAUAAUUGUGGU | Z-aCCaCaaAtTatGC-Y |
| | 6 | 12 | GGGACUGCGUUC | Z-GaACGCAGtCCC-Y |
| | 7 | 12 | CGCUUCCCCUG | Z-CaGGGGAaaGCG-Y |
| hsa-U2 snRNA | 1 | 15 | CUUUUGGCUAAGAUC | Z-GatCtTagCCAaAaG-Y |
| | 2 | 15 | GUGUAGUAUCUGUUC | Z-GaaCaGaTaCtACaC-Y |
| | 3 | 15 | AUAUCUGAUACGUCC | Z-GGaCGTatCAGatAt-Y |
| | 4 | 15 | AAUGGAUUUUUGGAG | Z-CtCCAaaaATCCaTt-Y |
| | 5 | 12 | AGCUUGCUCCGU | Z-aCGGAGCAaGCT-Y |
| | 6 | 12 | ACCUCCAGGAAC | Z-GtTCCTGGAGGt-Y |
| | 7 | 12 | GAACGGUGCACC | Z-GGTGCaCCGTtC-Y |
| hsa-hy3 scRNA | 1 | 15 | AGUGGUGUUACAAC | Z-GtTGTaaACACCaCt-Y |
| | 2 | 15 | CACAACCAGUACAG | Z-CtGTaCtGGtTGtG-Y |
| | 3 | 15 | GUUCCUUCUCCACUC | Z-GaGtGGaGaAGgaaC-Y |
| | 4 | 15 | CACUGCUUCACUGA | Z-tCaAGtGAaGCaGtG-Y |
| hsa-7SL scRNA | 1 | 15 | GUGCCUGUAGUCCCA | Z-tGGGACTaCAGGCaC-Y |
| | 2 | 15 | GCACUAAGUUCGGCA | Z-tGCCGAacTtAGtGC-Y |
| | 3 | 15 | ACCAGGUUGCCUAAG | Z-CtTaGGCaACCTGGt-Y |
| | 4 | 15 | CAGGUCAAAACTCCC | Z-GGGAgTtTtgaCCTG-Y |
| | 5 | 15 | GCUGAUCAGUAGUGG | Z-CCaCTaCtGATCaGC-Y |
| | 6 | 15 | TAGCCACUGCACTCC | Z-GGAGTGCaGTGGCtA-Y |
| hsa-U3 snoRNA | 1 | 14 | ACUAUACUUUCAGG | Z-CCtgAAaGTaTagT-Y |
| | 2 | 16 | UCAUUUCUAUAGUGUG | Z-CaCAcTaTagAaATga-Y |
| | 3 | 14 | UGUAGAGCACCGAA | Z-tTCGGTGCTCTaCa-Y |
| | 4 | 14 | GCGUUUUCUCCUGA | Z-TcAGGaGaaAAcGC-Y |
| | 5 | 12 | GCUGCAACUGCC | Z-GGCAGttGCAGC-Y |

FIG. 44

| RNA category | Probe | Length (nt) | RNA Sequence | LNA sequence |
|---|---|---|---|---|
| HER2/ERBB2 | 1 | 12 | GCTGCUGAGGA | tCCTCaaGCAGC-L-X-L-W |
| | 2 | 13 | CCCUUACTGCGC | GCGCAGtaAaGGG-L-X-L-W |
| | 3 | 11 | CCCUCUTGCCC | GGGCAaGaGGG-L-X-L-W |
| | 4 | 12 | CCACCTGGACAU | atGTCCAGGTGG-L-X-L-W |
| | 5 | 13 | CCACCCTCUACCAG | CtGGTaGAGGtGG-L-X-L-W |
| | 6 | 12 | CACCAAUGCCAG | CTGGCattGGtG-L-X-L-W |
| | 7 | 14 | GCUCACAACCAAGU | aCtTGGTtGTGaGC-L-X-L-W |
| | 8 | 11 | CACUGCAGAGG | CCTCTGCagtG-L-X-L-W |
| | 9 | 14 | CUAGACAAUGGAGA | tCTCCAtTGTCTaG-L-X-L-W |
| | 10 | 14 | CCTCACAGAGATCU | aGATCtCtGtGAGG-L-X-L-W |
| | 11 | 12 | CAGCTCUGCUAC | GtaGCaGAGCTG-L-X-L-W |
| | 12 | 15 | GACACGATUUTGUGG | CCaCAaaAtCGTGTC-L-X-L-W |
| | 13 | 14 | GGACAUCUTCCACA | tGtGGAaGaTGTCC-L-X-L-W |
| | 14 | 14 | CCUGUTCTCCGAUGU | aCaTCGGAGAaCatGG-L-X-L-W |
| | 15 | 12 | GACUGCTGCCAU | atGGCAGCagtC-L-X-L-W |
| | 16 | 12 | GAGCAGTGUGCU | aGCaCACTGCTC-L-X-L-W |
| | 17 | 15 | CUGGTCACCTACAAC | GtTGTAGGTGACCaG-L-X-L-W |
| | 18 | 15 | AGACACGUUTGAGUC | GaCTXAaaCGTGTCt-L-X-L-W |
| | 19 | 14 | CGGUAUACATUCGG | CCGaAtGtaTaCCG-L-X-L-W |
| | 20 | 13 | AGCTGUGTGACUG | CagtCACaCAGCt-L-X-L-W |
| | 21 | 16 | CUACAACTACCTUTCTAC | GtAGAaAGGTAGTtGTaG-L-X-L-W |
| | 22 | 13 | GCACAACCAAGAG | CtCTTGGTtGtGC-L-X-L-W |
| | 23 | 11 | GGAACACAGCG | CGCtGTGTtCC-L-X-L-W |
| | 24 | 14 | GTGTGCTATGGUCU | aGaCCAtAGCACAC-L-X-L-W |
| | 25 | 14 | GAGAGCTUTGAUGG | CCaTCAaaGCTCtC-L-X-L-W |
| | 26 | 12 | CUCCAACACGGC | GCaGTGTtGGaG-L-X-L-W |
| | 27 | 16 | CCAAGTGUTGGAGAUC | aGtCTCaAaCACTtGG-L-X-L-W |
| | 28 | 13 | AAGAGAUCACAGG | CCTGTGatCtCTt-L-X-L-W |
| | 29 | 15 | CCUAUACAUCUCAGC | GCTGAaTGtAtaGG-L-X-L-W |
| | 30 | 14 | ACCTGCAAGUAAUC | GatTaCTtGCAGGt-L-X-L-W |
| | 31 | 14 | GACCGAAUUCTGCAC | GTGCAGaaTTCGtC-L-X-L-W |
| | 32 | 15 | UCATCCACCAUAACA | tGtTatGGTGGAtGa-L-X-L-W |
| | 33 | 12 | CCAAGCUCTGCU | aGCAGaGCtTGG-L-X-L-W |
| | 34 | 14 | UGUGTCAACTGCAG | CtGCAGtTGACaCa-L-X-L-W |
| | 35 | 12 | CGAGUACTGCAG | CtGCAGtaCtCG-L-X-L-W |
| | 36 | 13 | ACCUGUUUTGGAC | GtCCAaaaCaGGt-L-X-L-W |
| | 37 | 15 | ACGTCCAUCATCUCU | aGaGATGatGGACGt-L-X-L-W |
| | 38 | 13 | GAAGUACACGAUG | CatCGTGtaCttC-L-X-L-W |
| | 39 | 12 | CUGACACCTAGC | GCtAGGTGTCaG-L-X-L-W |
| | 40 | 12 | GCACAGTCUACA | tGtaGACtGtGC-L-X-L-W |
| | 41 | 15 | AUCTGGATCCCTGAU | atCAGGGATCCAGat-L-X-L-W |
| | 42 | 15 | GUGACACAGCTTAUG | CatAAGCTGTGTCaC-L-X-L-W |
| | 43 | 12 | CUCGUACACAGG | CCTGtGtaCGaG-L-X-L-W |
| | 44 | 13 | CCAGAGTGATGUG | CaCAtCACTCtGG-L-X-L-W |
| | 45 | 13 | GUGTGACUGTGUG | CaCACaGTCACaC-L-X-L-W |
| | 46 | 15 | CCAAACCUACGATG | CAtCGTaGGTttGG-L-X-L-W |
| | 47 | 15 | CAUCTGCACCAUUGA | tCaAtGGTGCAGatG-L-X-L-W |
| | 48 | 15 | GUGGTCATCCAGAAU | atTCtGGAtGACCaC-L-X-L-W |
| | 49 | 15 | CUUCUUCTGTCCAGA | tCtGGACAGaaGaaG-L-X-L-W |
| | 50 | 12 | CCTGACAACUAGG | CCTtaGtGTCAGG-L-X-L-W |
| | 51 | 15 | CGAACAACUCUCUAUUA | taATaGaGGTtGtCG-L-X-L-W |
| | 52 | 12 | AGAACCAGAGUA | taCTCTGGGTTCt-L-X-L-W |
| | 53 | 14 | CUGACTUCTGCTGG | CCAGCAGaAGTCaG-L-X-L-W |
| | 54 | 12 | GACCACUUCCAG | CtGGaaGTGGTC-L-X-L-W |
| | 55 | 11 | AAGCCUUAGGG | CCCTaaGGCtT-L-X-L-W |
| | 56 | 14 | CAUTCAGAGACUGU | aCaGTCtCtGaatG-L-X-L-W |
| | 57 | 13 | GUACAGAGTGCUU | aaGCACTCtGtaC-L-X-L-W |

SEQUENCE LISTING

```
<160> NUMBER OF SEQ ID NOS: 278

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
```

```
<220> FEATURE:
<223> OTHER INFORMATION: C-term NH2

<400> SEQUENCE: 1

Gly Phe Lys Gly
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (3)..(3)
<223> OTHER INFORMATION: Lys, Glu, Gln, Cys, Ser or Gly
<220> FEATURE:
<223> OTHER INFORMATION: C-term NH2

<400> SEQUENCE: 2

Gly Phe Xaa Gly
1

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 3
agttgttaca cactccttag                                               20

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 4
uccuucauuc caccggaguc ug                                            22

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 5
uuuguucguu cggcucgcgu ga                                            22

<210> SEQ ID NO 6
<211> LENGTH: 17
<212> TYPE: RNA
<213> ORGANISM: Artificial Sequence
```

-continued

```
<220> FEATURE:
<223> OTHER INFORMATION: Description of Artificial Sequence: Synthetic
      probe

<400> SEQUENCE: 6
aucagacccc agaaaag                                                    17

<210> SEQ ID NO 7
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 7
cggaacggga cggga                                                      15

<210> SEQ ID NO 8
<211> LENGTH: 18
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 8
agucgguccu gagagaug                                                   18

<210> SEQ ID NO 9
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 9
ucaguacgag aggaacc                                                    17

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ggtggaatga agga                                                       14

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
agccgaacga acaaa                                                      15

<210> SEQ ID NO 12
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 12

Gly Phe Glu Gly
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 13

Gly Phe Gln Gly
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 14

Gly Phe Cys Gly
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2

<400> SEQUENCE: 15

Gly Phe Ser Gly
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term CONH2
```

<400> SEQUENCE: 16

Gly Phe Gly Gly
1

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
cttttctggg gtctgat                                                  17

<210> SEQ ID NO 18
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tcccgtcccg ttccg                                                    15

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
catctctcag gaccgact                                                 18

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ggttcctctc gtactga                                                  17

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
cttttctggg gtctgat                                                  17

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 22
tcccgtcccg ttccg                                                      15

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
catctctcag gaccgact                                                   18

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
ggttcctctc gtactga                                                    17

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
ccttttctgg ggtctgatga gcgtcggc                                        28

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
cgctcccgtc ccgttccgtt c                                               21

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cactcgccca tctctcagga ccgactgacc                                      30

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
```
cctgcggttc ctctcgtact gagcagg          27

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
cagactccgg tggaatgaag ga          22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cagactccgg tggaatgaag ga          22

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ggtggaatga agga          14

<210> SEQ ID NO 32
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ggtggaatga agga          14

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
tcacgcgagc cgaacgaaca aa          22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
tcacgcgagc cgaacgaaca aa                                           22

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
agccgaacga acaaa                                                   15

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
agccgaacga acaaa                                                   15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
agccgaacga acaaa                                                   15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
agccgaacga acaaa                                                   15

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 39
ggaaaagaaa ctaaccagga                                              20

<210> SEQ ID NO 40
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:

<223> OTHER INFORMATION: Description of Combined DNA/RNA Molecule:
      Synthetic probe

<400> SEQUENCE: 40
atcagacccc agaaaag                                                    17

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 41
ctaaggagtg tgtaacaact                                                 20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 42
ctgaaaatgg atggcgctg                                                  19

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 43
agtcggtcct gagagatg                                                   18

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 44
ggagcagaag ggcaaa                                                     16

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      probe <220> FEATURE:
<223> OTHER INFORMATION: Description of Combined DNA/RNA Molecule:
      Synthetic probe

<400> SEQUENCE: 45
tcagtacgag aggaacc                                                17

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 46
tcctggttag tttcttttcc                                             20

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 47
cagcgccatc cattttcag                                              19

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 48
tttgcccttc tgctcc                                                 16

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
tttttttttt tttttttttt tttttttttt                                  30

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
tttttttttt tttttttttt t                                        21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
tttttttttt tttttttttt t                                        21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
tttttttttt tttttttttt t                                        21

<210> SEQ ID NO 53
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 53
aggagugugu aacaacu                                             17

<210> SEQ ID NO 54
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 54
cugaaaaugg auggcgc                                             17

<210> SEQ ID NO 55
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 55
gucgguccug agagaug                                             17

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56

```
guacccauau ccgcagc                                                    17

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 57
ucagtacgag aggaacc                                                    17

<210> SEQ ID NO 58
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 58
uugguccuag ccuuucu                                                    17

<210> SEQ ID NO 59
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 59
aacuaagcua uacuaac                                                    17

<210> SEQ ID NO 60
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 60
ggucacacga uuaaccc                                                    17

<210> SEQ ID NO 61
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 61
gccaucuuca gcaaacc                                                    17

<210> SEQ ID NO 62
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 62
aagacguuag gucaagg                                                    17
```

<210> SEQ ID NO 63
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 63
aggcuacaaa guaagcg                                                    17

<210> SEQ ID NO 64
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 64
cuaccagaca accuuag                                                    17

<210> SEQ ID NO 65
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 65
cagcuaaaag agcacac                                                    17

<210> SEQ ID NO 66
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 66
gguuguccaa gauagaa                                                    17

<210> SEQ ID NO 67
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 67
uccucacacc caauugg                                                    17

<210> SEQ ID NO 68
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 68
aaaacaucac cucuagc                                                    17

```
<210> SEQ ID NO 69
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 69
aacaguaccu aacaaac                                                 17

<210> SEQ ID NO 70
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 70
gaggguauca agcac                                                   15

<210> SEQ ID NO 71
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 71
ggcguaaaac guguc                                                   15

<210> SEQ ID NO 72
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 72
gccaucuuca gcaaa                                                   15

<210> SEQ ID NO 73
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 73
ccacuaugcu uagcc                                                   15

<210> SEQ ID NO 74
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 74
ggacucagca gugau                                                   15
```

```
<210> SEQ ID NO 75
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 75
cuccaggcau acgcg                                                           15

<210> SEQ ID NO 76
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 76
caagagaaau agagc                                                           15

<210> SEQ ID NO 77
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 77
cuguuaaccc aacac                                                           15

<210> SEQ ID NO 78
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 78
augcaacacu guuag                                                           15

<210> SEQ ID NO 79
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 79
ccuacgugau cugag                                                           15

<210> SEQ ID NO 80
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 80
ggagauacca ug                                                              12

<210> SEQ ID NO 81
```

```
<211> LENGTH: 14
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 81
gaggcuuauc cauu                                                         14

<210> SEQ ID NO 82
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 82
ggaugugcug ac                                                           12

<210> SEQ ID NO 83
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 83
ugcgauuucc cc                                                           12

<210> SEQ ID NO 84
<211> LENGTH: 14
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 84
gcauaauuug uggu                                                         14

<210> SEQ ID NO 85
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 85
gggacugcgu uc                                                           12

<210> SEQ ID NO 86
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 86
cgcuuucccc ug                                                           12

<210> SEQ ID NO 87
<211> LENGTH: 15
```

```
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 87
cuuuuggcua agauc                                                      15

<210> SEQ ID NO 88
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 88
guguaguauc uguuc                                                      15

<210> SEQ ID NO 89
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 89
auaucugaua cgucc                                                      15

<210> SEQ ID NO 90
<211> LENGTH: 15
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 90
aauggauuuu uggag                                                      15

<210> SEQ ID NO 91
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 91
agcuugcucc gu                                                         12

<210> SEQ ID NO 92
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 92
accuccagga ac                                                         12

<210> SEQ ID NO 93
<211> LENGTH: 12
<212> TYPE: RNA
```

```
<213> ORGANISM: Artificial Sequence
<220> FEATURE:
<223> OTHER INFORMATION: Description of Artificial Sequence: Synthetic
      probe

<400> SEQUENCE: 93
gaacggugca cc                                                          12

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 94
aguggtgtuu acaac                                                       15

<210> SEQ ID NO 95
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 95
cacaaccagt uacag                                                       15

<210> SEQ ID NO 96
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 96
guucctucuc cacuc                                                       15

<210> SEQ ID NO 97
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 97
cacugcutca ctuga                                                       15

<210> SEQ ID NO 98
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 98
gugcctguag tccca                                                    15

<210> SEQ ID NO 99
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 99
gcactaagut cggca                                                    15

<210> SEQ ID NO 100
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 100
accaggtugc cuaag                                                    15

<210> SEQ ID NO 101
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 101
caggucaaaa ctccc                                                    15

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 102
gcugatcagu agugg                                                    15

<210> SEQ ID NO 103
<211> LENGTH: 15
<212> TYPE: DNA
<213> ORGANISM: Artificial Sequence
```

```
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 103
tagccacugc actcc                                              15

<210> SEQ ID NO 104
<211> LENGTH: 14
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 104
acuauacuuu cagg                                               14

<210> SEQ ID NO 105
<211> LENGTH: 16
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 105
ucauuucuau agugug                                             16

<210> SEQ ID NO 106
<211> LENGTH: 14
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 106
uguagagcac cgaa                                               14

<210> SEQ ID NO 107
<211> LENGTH: 14
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 107
gcguuuucuc cuga                                               14

<210> SEQ ID NO 108
<211> LENGTH: 12
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 108
gcugcaacug cc                                                 12

<210> SEQ ID NO 109
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 109
agttgttaca cactcct                                                     17

<210> SEQ ID NO 110
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 110
gcgccatcca ttttcag                                                     17

<210> SEQ ID NO 111
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 111
catctctcag gaccgac                                                     17

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 112
gctgcggata tgggtac                                                     17

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 113
ggttcctctc gtactga                                                     17

<210> SEQ ID NO 114
```

-continued

```
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 114
agaaaggcta ggaccaa                                                    17

<210> SEQ ID NO 115
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 115
gttagtatag cttagtt                                                    17

<210> SEQ ID NO 116
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 116
gggttaatcg tgtgacc                                                    17

<210> SEQ ID NO 117
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 117
ggtttgctga agatggc                                                    17

<210> SEQ ID NO 118
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 118
ccttgaccta acgtctt                                                    17
```

```
<210> SEQ ID NO 119
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 119
cgcttacttt gtagcct                                                  17

<210> SEQ ID NO 120
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 120
ctaaggttgt ctggtag                                                  17

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 121
gtgtgctctt ttagctg                                                  17

<210> SEQ ID NO 122
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 122
ttctatcttg gacaacc                                                  17

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 123
ccaattgggt gtgagga                                                  17
```

```
<210> SEQ ID NO 124
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 124
gctagaggtg atgtttt                                                  17

<210> SEQ ID NO 125
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 125
gtttgttagg tactgtt                                                  17

<210> SEQ ID NO 126
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 126
gtgcttgata ccctc                                                    15

<210> SEQ ID NO 127
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 127
gacacgtttt acgcc                                                    15

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 128
tttgctgaag atggc                                                    15
```

```
<210> SEQ ID NO 129
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 129
ggctaagcat agtgg                                                      15

<210> SEQ ID NO 130
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 130
atcactgctg agtcc                                                      15

<210> SEQ ID NO 131
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 131
cgcgtatgcc tggag                                                      15

<210> SEQ ID NO 132
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 132
gctctatttc tcttg                                                      15

<210> SEQ ID NO 133
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 133
```
gtgttgggtt aacag                                                      15

<210> SEQ ID NO 134
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 134
ctaacagtgt tgcat                                                      15

<210> SEQ ID NO 135
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 135
ctcagatcac gtagg                                                      15

<210> SEQ ID NO 136
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 136
catggtatct cc                                                         12

<210> SEQ ID NO 137
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 137
aatggataag cctc                                                       14

<210> SEQ ID NO 138
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 138

```
gtcagcacat cc                                                          12

<210> SEQ ID NO 139
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 139
ggggaaatcg ca                                                          12

<210> SEQ ID NO 140
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 140
accacaaatt atgc                                                        14

<210> SEQ ID NO 141
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 141
gaacgcagtc cc                                                          12

<210> SEQ ID NO 142
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 142 cagggaaag cg                                                           12

<210> SEQ ID NO 143
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
```

-continued

<400> SEQUENCE: 143
gatcttagcc aaaag                                                        15

<210> SEQ ID NO 144
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 144
gaacagatac tacac                                                        15

<210> SEQ ID NO 145
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 145
ggacgtatca gatat                                                        15

<210> SEQ ID NO 146
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 146
ctccaaaaat ccatt                                                        15

<210> SEQ ID NO 147
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 147
acggagcaag ct                                                           12

<210> SEQ ID NO 148
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 148
gttcctggag gt                                                          12

<210> SEQ ID NO 149
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 149
ggtgcaccgt tc                                                          12

<210> SEQ ID NO 150
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 150
gttgtaaaca ccact                                                       15

<210> SEQ ID NO 151
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 151
ctgtaactgg ttgtg                                                       15

<210> SEQ ID NO 152
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 152
gagtggagaa ggaac                                                       15

<210> SEQ ID NO 153
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:

Synthetic probe

<400> SEQUENCE: 153
tcaagtgaag cagtg                    15

<210> SEQ ID NO 154
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 154
tgggactaca ggcac                    15

<210> SEQ ID NO 155
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 155
tgccgaactt agtgc                    15

<210> SEQ ID NO 156
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 156
cttaggcaac ctggt                    15

<210> SEQ ID NO 157
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 157
gggagttttg acctg                    15

<210> SEQ ID NO 158
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:

```
<223> OTHER INFORMATION: Description of Combined DNA/RNA Molecule:
      Synthetic probe

<400> SEQUENCE: 158
ccactactga tcagc                                                          15

<210> SEQ ID NO 159
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 159
ggagtgcagt ggcta                                                          15

<210> SEQ ID NO 160
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 160
cctgaaagta tagt                                                           14

<210> SEQ ID NO 161
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 161
cacactatag aaatga                                                         16

<210> SEQ ID NO 162
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 162
ttcggtgctc taca                                                           14

<210> SEQ ID NO 163
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: Description of Combined DNA/RNA Molecule:
      Synthetic probe

<400> SEQUENCE: 163
tcaggagaaa acgc                                                     14

<210> SEQ ID NO 164
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 164
ggcagttgca gc                                                       12

<210> SEQ ID NO 165
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 165
gctgcuugag ga                                                       12

<210> SEQ ID NO 166
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 166
cccutuactg cgc                                                      13

<210> SEQ ID NO 167
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 167
cccucutgcc c                                                        11

<210> SEQ ID NO 168
<211> LENGTH: 12
<212> TYPE: DNA
<213> ORGANISM: Artificial Sequence
<220> FEATURE:
<223> OTHER INFORMATION: Description of Artificial Sequence: Synthetic
``` probe
<220> FEATURE:
<223> OTHER INFORMATION: Description of Combined DNA/RNA Molecule:
      Synthetic probe

<400> SEQUENCE: 168
ccacctggac au                                                            12

<210> SEQ ID NO 169
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 169
ccacctcuac cag                                                           13

<210> SEQ ID NO 170
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 170
caccaaugcc ag                                                            12

<210> SEQ ID NO 171
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 171
gcucacaacc aagu                                                          14

<210> SEQ ID NO 172
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 172
cacugcagag g                                                             11

<210> SEQ ID NO 173
<211> LENGTH: 14
<212> TYPE: DNA
<213> ORGANISM: Artificial Sequence
<220> FEATURE:

```
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 173
cuagacaaug gaga                                                        14

<210> SEQ ID NO 174
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 174
cctcacagag atcu                                                        14

<210> SEQ ID NO 175
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 175
cagctcugcu ac                                                          12

<210> SEQ ID NO 176
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 176
gacacgatuu tgugg                                                       15

<210> SEQ ID NO 177
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 177
ggacaucutc caca                                                        14

<210> SEQ ID NO 178
<211> LENGTH: 15
<212> TYPE: DNA
<213> ORGANISM: Artificial Sequence
```

-continued

```
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 178
ccugutctcc gaugu                                                    15

<210> SEQ ID NO 179
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 179
gacugctgcc au                                                       12

<210> SEQ ID NO 180
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 180
gagcagtgug cu                                                       12

<210> SEQ ID NO 181
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 181
cuggtcacct acaac                                                    15

<210> SEQ ID NO 182
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 182
agacacguut gaguc                                                    15

<210> SEQ ID NO 183
<211> LENGTH: 14
<212> TYPE: DNA
```

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 183
cgguauacat ucgg                                                         14

<210> SEQ ID NO 184
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 184
agctgugtga cug                                                          13

<210> SEQ ID NO 185
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 185
cuacaactac ctutctac                                                     18

<210> SEQ ID NO 186
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 186
gcacaaccaa gag                                                          13

<210> SEQ ID NO 187
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 187
ggaacacagc g                                                            11

<210> SEQ ID NO 188
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 188
gtgtgctatg gucu                                                         14

<210> SEQ ID NO 189
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 189
gagagctutg augg                                                         14

<210> SEQ ID NO 190
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 190
cuccaacacu gc                                                           12

<210> SEQ ID NO 191
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 191
ccaagtgutu gagacu                                                       16

<210> SEQ ID NO 192
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 192
aagagaucac agg                                                          13

<210> SEQ ID NO 193
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 193
ccuatacauc tcagc                                                       15

<210> SEQ ID NO 194
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 194
acctgcaagu aauc                                                        14

<210> SEQ ID NO 195
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 195
gacgaauuct gcac                                                        14

<210> SEQ ID NO 196
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 196
ucatccacca uaaca                                                       15

<210> SEQ ID NO 197
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 197
ccaagcuctg cu                                                          12
```

```
<210> SEQ ID NO 198
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 198
ugugtcaact gcag                                                       14

<210> SEQ ID NO 199
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 199
cgaguactgc ag                                                         12

<210> SEQ ID NO 200
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 200
accuguuutg gac                                                        13

<210> SEQ ID NO 201
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 201
acgtccauca tcucu                                                      15

<210> SEQ ID NO 202
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 202
gaaguacacg aug                                                        13
```

<210> SEQ ID NO 203
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 203
cugacaccta gc                                                           12

<210> SEQ ID NO 204
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 204
gcacagtcua ca                                                           12

<210> SEQ ID NO 205
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 205
auctggatcc ctgau                                                        15

<210> SEQ ID NO 206
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 206
gugacacagc ttaug                                                        15

<210> SEQ ID NO 207
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 207
cucguacaca gg                                                           12

<210> SEQ ID NO 208
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 208
ccagagtgat gug                                                          13

<210> SEQ ID NO 209
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 209
gugtgacugt gug                                                          13

<210> SEQ ID NO 210
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 210
ccaaacctua cgatg                                                        15

<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 211
cauctgcacc atuga                                                        15

<210> SEQ ID NO 212
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 212
guggtcatcc agaau                    15

<210> SEQ ID NO 213
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 213
cuucuuctgt ccaga                    15

<210> SEQ ID NO 214
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 214
cctgacacua gg                       12

<210> SEQ ID NO 215
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 215
cgacaaccuc uatua                    15

<210> SEQ ID NO 216
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 216
agaacccaga gua                      13

<210> SEQ ID NO 217
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 217
cugacuucug cugg                                                              14

<210> SEQ ID NO 218
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 218
gaccacuucc ag                                                                12

<210> SEQ ID NO 219
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 219
aagccuuagg g                                                                 11

<210> SEQ ID NO 220
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 220
cautcagaga cugu                                                              14

<210> SEQ ID NO 221
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 221
guacagagtg cuu                                                               13

<210> SEQ ID NO 222
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

```
<400> SEQUENCE: 222
tcctcaagca gc                                                             12

<210> SEQ ID NO 223
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 223
gcgcagtaaa ggg                                                            13

<210> SEQ ID NO 224
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 224
gggcaagagg g                                                              11

<210> SEQ ID NO 225
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 225
atgtccaggt gg                                                             12

<210> SEQ ID NO 226
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 226
ctggtagagg tgg                                                            13

<210> SEQ ID NO 227
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
```

<400> SEQUENCE: 227
ctggcattgg tg                                                          12

<210> SEQ ID NO 228
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 228
acttggttgt gagc                                                        14

<210> SEQ ID NO 229
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 229
cctctgcagt g                                                           11

<210> SEQ ID NO 230
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 230
tctccattgt ctag                                                        14

<210> SEQ ID NO 231
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 231
agatctctgt gagg                                                        14

<210> SEQ ID NO 232
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:

Synthetic probe

<400> SEQUENCE: 232
gtagcagagc tg                                                          12

<210> SEQ ID NO 233
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 233
ccacaaaatc gtgtc                                                       15

<210> SEQ ID NO 234
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 234
tgtggaagat gtcc                                                        14

<210> SEQ ID NO 235
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 235
acatcggaga acagg                                                       15

<210> SEQ ID NO 236
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 236
atggcagcag tc                                                          12

<210> SEQ ID NO 237
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:

```
<223> OTHER INFORMATION: Description of Combined DNA/RNA Molecule:
      Synthetic probe

<400> SEQUENCE: 237
agcacactgc tc                                                           12

<210> SEQ ID NO 238
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 238
gttgtaggtg accag                                                        15

<210> SEQ ID NO 239
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 239
gactcaaacg tgtct                                                        15

<210> SEQ ID NO 240
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 240
ccgaatgtat accg                                                         14

<210> SEQ ID NO 241
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 241
cagtcacaca gct                                                          13

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<223> OTHER INFORMATION: Description of Combined DNA/RNA Molecule:
      Synthetic probe

<400> SEQUENCE: 242
gtagaaaggt agttgtag                                                 18

<210> SEQ ID NO 243
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 243
ctcttggttg tgc                                                      13

<210> SEQ ID NO 244
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 244
cgctgtgttc c                                                        11

<210> SEQ ID NO 245
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 245
agaccatagc acac                                                     14

<210> SEQ ID NO 246
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 246
ccatcaaagc tctc                                                     14

<210> SEQ ID NO 247
<211> LENGTH: 12
<212> TYPE: DNA
<213> ORGANISM: Artificial Sequence
<220> FEATURE:
<223> OTHER INFORMATION: Description of Artificial Sequence: Synthetic
```

-continued

```
      probe
<220> FEATURE:
<223> OTHER INFORMATION: Description of Combined DNA/RNA Molecule:
      Synthetic probe

<400> SEQUENCE: 247
gcagtgttgg ag                                                          12

<210> SEQ ID NO 248
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 248
agtctcaaac acttgg                                                      16

<210> SEQ ID NO 249
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 249
cctgtgatct ctt                                                         13

<210> SEQ ID NO 250
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 250
gctgagatgt atagg                                                       15

<210> SEQ ID NO 251
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 251
gattacttgc aggt                                                        14

<210> SEQ ID NO 252
<211> LENGTH: 14
<212> TYPE: DNA
<213> ORGANISM: Artificial Sequence
<220> FEATURE:
```

<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 252
gtgcagaatt cgtc                                                       14

<210> SEQ ID NO 253
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 253
tgttatggtg gatga                                                      15

<210> SEQ ID NO 254
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 254
agcagagctt gg                                                         12

<210> SEQ ID NO 255
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 255
ctgcagttga caca                                                       14

<210> SEQ ID NO 256
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 256
ctgcagtact cg                                                         12

<210> SEQ ID NO 257
<211> LENGTH: 13
<212> TYPE: DNA
<213> ORGANISM: Artificial Sequence

```
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 257
gtccaaaaca ggt                                                         13

<210> SEQ ID NO 258
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 258
agagatgatg gacgt                                                       15

<210> SEQ ID NO 259
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 259
catcgtgtac ttc                                                         13

<210> SEQ ID NO 260
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 260
gctaggtgtc ag                                                          12

<210> SEQ ID NO 261
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 261
tgtagactgt gc                                                          12

<210> SEQ ID NO 262
<211> LENGTH: 15
<212> TYPE: DNA
```

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 262
atcagggatc cagat                                                         15

<210> SEQ ID NO 263
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 263
cataagctgt gtcac                                                         15

<210> SEQ ID NO 264
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 264
cctgtgtacg ag                                                            12

<210> SEQ ID NO 265
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 265
cacatcactc tgg                                                           13

<210> SEQ ID NO 266
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 266
cacacagtca cac                                                           13

<210> SEQ ID NO 267
<211> LENGTH: 15
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 267
catcgtaagg tttgg                                                     15

<210> SEQ ID NO 268
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 268
tcaatggtgc agatg                                                     15

<210> SEQ ID NO 269
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 269
attctggatg accac                                                     15

<210> SEQ ID NO 270
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 270
tctggacaga agaag                                                     15

<210> SEQ ID NO 271
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 271
cctagtgtca gg                                                        12

<210> SEQ ID NO 272
```

-continued

```
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 272
taatagaggt tgtcg                                                      15

<210> SEQ ID NO 273
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 273
tactctgggt tct                                                        13

<210> SEQ ID NO 274
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 274
ccagcagaag tcag                                                       14

<210> SEQ ID NO 275
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 275
ctggaagtgg tc                                                         12

<210> SEQ ID NO 276
<211> LENGTH: 11
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 276
ccctaaggct t                                                          11
```

```
<210> SEQ ID NO 277
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 277
acagtctctg aatg                                                     14

<210> SEQ ID NO 278
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 278
aagcactctg tac                                                      13
```

METHODS FOR FIXING AND DETECTING RNA

CROSS-REFERENCE TO RELATED APPLICATIONS

This application is a U.S. National Phase Application of International Application No. PCT/US2012/048727 filed on Jul. 27, 2012 and asserts priority to U.S. Provisional Patent Application No. 61/512,228 filed on Jul. 27, 2011, all of which are hereby incorporated by reference in their entirety.

This application claims priority to U.S. Provisional Application No. 61/512,228 filed Jul. 27, 2011.

This invention was made with government support under NCI RO1 CA159227-01 awarded by the National Institutes of Health. Accordingly, the government has certain rights in the invention.

BACKGROUND OF THE INVENTION

RNA impacts nearly every aspect of gene expression and many human diseases are caused by or result in mistakes in RNA metabolism, e.g. mutations in pre-mRNAs lead to splicing defects or degradation of mRNAs by trigger nonsense-mediated mRNA decay. It has been shown that in addition to RNA's fundamental roles in information transfer from DNA to protein, RNA molecules play crucial roles in gene regulation as their stability or rate of protein synthesis is regulated by mRNA binding proteins or ribonucleoprotein complexes (RNPs), e.g. microRNA-containing RNPs.

Given this widespread clinical utility, there is a significant need to develop and optimize RNA detection, quantitation, and visualization assays for diagnostic purposes.

For example, recent studies link micro RNAs ("miRNAs") with diseases such as cancer and neurological disorders. To date, miRNA profiling has been used to classify cancers of known and unknown primary origin, determine prognosis and disease progression, predict chemoresistance, monitor therapy, and screen for disease.

miRNAs have specific expression and function in specialized cell types, emphasizing the need to define cell-type-specific miRNA expression patterns. The most common method for visualizing gene expression in specific cell types is in situ hybridization (ISH).

However, conventional ISH methods permit the release and diffusion of small nucleic acids, such as miRNA, from tissue. As a consequence, current ISH are not reliable for measuring small nucleic acids such as miRNA.

To establish miRNA-based diagnostics, it is essential to define a clinical need, reliably extract small RNAs from clinical materials, detect and quantitate miRNA expression differences between samples, and establish tractable molecular tests for clinical laboratory use.

Developing quantitative RNA ISH methods to detect cell-type-specific gene expression signatures in archived clinical materials would be a major advance in molecular diagnostics. Because RNA remains intact in archived samples (though partially hydrolyzed into shorter segments) and next-generation RNA sequencing is being used to resolve gene expression variation at the cellular level in tissue sections, RNA visualization methods are urgently needed.

Therefore, there remains a need for improved methods to fix, retain, quantify, visualize and detect RNA in a biological sample.

SUMMARY OF THE INVENTION

The invention provides a method for fixing an RNA molecule in a biological sample. The method includes contacting the biological sample with an aldehyde-containing fixative, and subsequently contacting the sample with a solution comprising a carbodiimide and a heterocyclic derivative selected from the group consisting of an imidazole, pyrazole, triazole or tetrazole or a combination thereof.

In one embodiment, the heterocyclic derivative has at least one of the following structures:

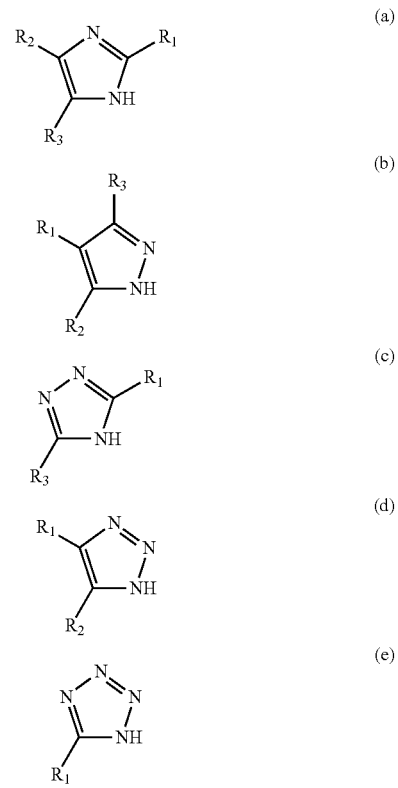

wherein $R_1$, $R_2$, and $R_3$ independently are H, alkyl, aryl, F, Cl, Br, I, CN, $NO_2$, $NH_2$, OH, SH, ethylthio-, alkyloxy-, or carbonyl.

In one aspect of the invention, the aldehyde-containing fixative is formaldehyde.

In another aspect, the heterocyclic derivative is selected from the group consisting of 2-methylimidazole, imidazole, 1-hydroxyl-benzotriazole, 5-ethylthiotetrazole, and 2-chloroimidazole. In an embodiment, the heterocyclic derivative is 5-ethylthiotetrazole.

In another embodiment, the carbodiimide is selected from the group consisting of 1-ethyl-3-(3-dimethylaminopropyl) carbodiimide (EDC), 1-ethyl-3-(3-dimethylaminopropyl) carbodiimide hydrochloride (EDC-HCl), 1-cyclohexyl-3-(2-morpholinyl-(4)-ethyl)carbodiimide metho-p-toluenesulfonate (CMC), N,N'-dicyclohexylcarbodiimide (DCC), N,N'-diisopropylcarbodiimide (DIC), and 1-ethyl-3-(3-dimethylaminopropyl)-carbodiimide methiodide (EDC-MeI). In another aspect, the carbodiimide is 1-ethyl-3-(3-dimethylaminopropyl)carbodiimide hydrochloride (EDC-HCl) or 1-ethyl-3-(3-dimethylaminopropyl)-carbodiimide methiodide (EDC-MeI).

In a preferred embodiment, the carbodiimide is 1-ethyl-3-(3-dimethylaminopropyl)carbodimide hydrochloride (EDC-HCl) or 1-ethyl-3-(3-dimethylaminopropyl)carbodiimide methiodide (EDC-MeI) and the heterocyclic derivative is 5-ethylthiotetrazole.

In yet another embodiment, the 1-ethyl-3-(3-dimethylaminopropyl)carbodiimide hydrochloride (EDC-HCl) or 1-ethyl-3-(3-dimethylaminopropyl)carbodiimide methiodide (EDC-MeI) has a concentration of about 20 mM to about 300 mM.

In one aspect, the solution comprising 1-ethyl-3-(3-dimethylaminopropyl)carbodiimide hydrochloride (EDC-HCl) or 1-ethyl-3-(3-dimethylaminopropyl)carbodiimide methiodide (EDC-MeI) contacts the sample at a temperature of about 20° C. to about 70° C.

In another aspect of the invention, the solution comprising a carbodiimide and a heterocyclic derivative and has a pH of about 6.0 to about 10.0. In an alternate embodiment, the solution comprising a carbodiimide and a heterocyclic derivative has a pH of about 7.0 to about 8.0.

In an embodiment of the invention, the RNA molecule is a short RNA. In an additional embodiment, the RNA molecule is a miRNA.

In yet another embodiment of the invention, the solution comprising a carbodiimide and a heterocyclic derivative further comprises a detergent. In one aspect, the detergent is selected from the group consisting of TWEEN20 (Polysorbate20), TWEEN80 (Polysorbate80), TRITON A-100 (Octylphenol ethoxylate), TRITON-114 (tert-octylphenoxypoly (ethoxyethanol)), Digitonin, Saponin, CHAPS (3-[(3-Cholamidopropyl)dimethyammonio]-1-propanesulfonate), Denhardt's solution, Heparin, BRIJ35 (Polyethylene glycol hexadecylether), Sodium dodecyl sulfate (SDS), and urea.

In another aspect, the method further comprises contacting the solution comprising a carbodiimide and a heterocyclic derivative with a cyanogen halide. In one aspect, the cyanogen halide is selected from the group consisting of cyanogen bromide, cyanogen iodide, cyanogen chloride and cyanogen fluoride.

In a preferred embodiment, the cyanogen halide is cyanogen bromide or cyanogen iodide.

A method for detecting a target RNA molecule in a biological sample is also provided. The method includes contacting the biological sample with an aldehyde-containing fixative, then contacting the sample with a solution comprising a carbodiimide and a heterocyclic derivative to produce crosslinked RNA in the sample. The heterocyclic derivative can be selected from the group consisting of an imidazole, pyrazole, triazole or tetrazole or a combination thereof. Next, the sample is contacted with a probe that is complementary to all or a part of a region of interest of the RNA in the sample, thereby producing hybridized RNA. Finally, the hybridized RNA is detected as the target RNA.

In one embodiment, the heterocyclic derivative has at least one of the following structures:

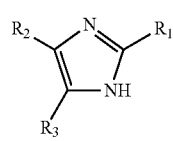

(a)

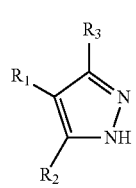

(b)

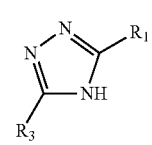

(c)

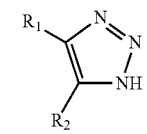

(d)

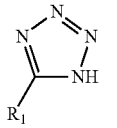

(e)

wherein $R_1$, $R_2$, and $R_3$ independently are H, alkyl, aryl, F, Cl, Br, I, CN, $NO_2$, $NH_2$, OH, SH, ethylthio-, alkyloxy-, or carbonyl. In one aspect of the invention, the aldehyde-containing fixative is formaldehyde.

In another aspect, the heterocyclic derivative is selected from the group consisting of 2-methylimidazole, imidazole, 1-hydroxyl-benzotriazole, 5-ethylthiotetrazole, and 2-chloroimidazole. In an embodiment, the heterocyclic derivative is 5-ethylthiotetrazole.

In another embodiment, the carbodiimide is selected from the group consisting of 1-ethyl-3-(3-dimethylaminopropyl) carbodiimide (EDC), 1-ethyl-3-(3-dimethylaminopropyl) carbodiimide hydrochloride (EDC-HCl), 1-cyclohexyl-3-(2-morpholinyl-(4)-ethyl)carbodiimide metho-p-toluenesulfonate (CMC), N,N'-dicyclohexylcarbodiimide (DCC), N,N'-diisopropylcarbodiimide (DIC), and 1-ethyl-3-(3-dimethylaminopropyl)-carbodiimide methiodide (EDC-MeI). In another aspect, the carbodiimide is 1-ethyl-3-(3-dimethylaminopropyl)carbodiimide hydrochloride (EDC-HCl).

In a preferred embodiment, the carbodiimide is 1-ethyl-3-(3-dimethylaminopropyl)carbodiimide hydrochloride (EDC-HCl) or 1-ethyl-3-(3-dimethylaminopropyl)carbodiimide methiodide (EDC-MeI) and the heterocyclic derivative is 5-ethylthiotetrazole.

In yet another embodiment, the 1-ethyl-3-(3-dimethylaminopropyl)carbodiimide hydrochloride (EDC-HCl) or 1-ethyl-3-(3-dimethylaminopropyl)carbodiimide methiodide (EDC-MeI) has a concentration of about 20 mM to about 300 mM.

In one aspect, the solution comprising 1-ethyl-3-(3-dimethylaminopropyl) carbodiimide hydrochloride (EDC-HCl) or 1-ethyl-3-(3-dimethylaminopropyl)carbodiimide methiodide (EDC-MeI) contacts the sample at a temperature of about 20° C. to about 70° C.

In another aspect of the invention, the solution comprising a carbodiimide and a heterocyclic derivative and has a pH of about 6.0 to about 10.0. In an alternate embodiment, the solution comprising a carbodiimide and a heterocyclic derivative has a pH of about 7.0 to about 8.0.

In an embodiment of the invention, the RNA molecule is a short RNA. In an additional embodiment, the RNA molecule is a miRNA.

In yet another embodiment of the invention, the solution comprising a carbodiimide and a heterocyclic derivative further comprises a detergent. In one aspect, the detergent is selected from the group consisting of TWEEN20 (Polysorbate20), TWEEN80 (Polysorbate80), TRITON A-100 (Octylphenol ethoxylate), TRITON-114 (tert-octylphenoxypoly (ethoxyethanol)), Digitonin, Saponin, CHAPS (3-[(3-Cholamidopropyl)dimethyammonio]-1-propanesulfonate), Denhardt's solution, Heparin, BRIJ35 (Polyethylene glycol hexadecylether), Sodium dodecyl sulfate (SDS), and urea.

In another aspect, the method further includes contacting the solution comprising a carbodiimide and a heterocyclic derivative with a cyanogen halide. In one aspect, the cyanogen halide is selected from the group consisting of cyanogen bromide, cyanogen iodide, cyanogen chloride and cyanogen fluoride. In a preferred embodiment, the cyanogen halide is cyanogen bromide or cyanogen iodide.

In one embodiment, the probe includes a locked nucleic acid (LNA) residue. In another embodiment, the probe includes a or PNA probe, or 2'-OMe probe or 2'-O-ethyl (2'-OEt) probe or 2'-O-methoxyethyl (MOE) or 2',4'-contrained MOE bicyclic nucleic acid (cMOE BNA) probe or 2',4'-contrained 2'-O-ethyl bicyclic (cEt BNA) probe or S-DNA probe residue, and the like. In one aspect, the probe further includes a linker having a length greater than about 3.0 nm.

A kit for fixing a RNA in a biological sample is also provided. The kit includes a support substrate for holding the sample, an aldehyde-containing fixative, a carbodiimide; and a heterocyclic derivative selected from the group consisting of an imidazole, pyrazole, triazole or tetrazole derivative or a combination thereof.

In one embodiment, the heterocyclic derivative has at least one of the following structures:

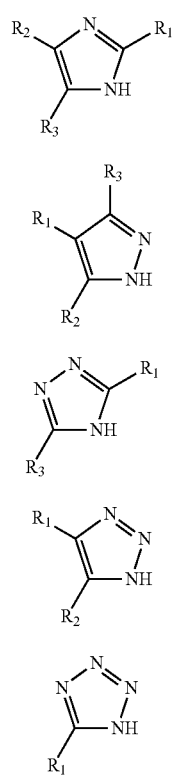

wherein $R_1$, $R_2$, and $R_3$ independently are H, alkyl, aryl, F, Cl, Br, I, CN, $NO_2$, $NH_2$, OH, SH, ethylthio-, alkyloxy-, or carbonyl. In one aspect of the invention, the aldehyde-containing fixative is formaldehyde.

In one embodiment, the water soluble carbodiimide is 1-ethyl-3-(3 dimethylaminopropyl)carbodiimide hydrochloride (EDC-HCl) or 1-ethyl-3-(3-dimethylaminopropyl)carbodiimide methiodide (EDC-MeI). In another embodiment, the heterocyclic derivative is 5-ethylthiotetrazole.

The invention also provides a method for differentiating cells in a biological sample. The method includes contacting the biological sample with an aldehyde-containing fixative, then contacting the sample with a solution comprising a carbodiimide and a heterocyclic derivative to produce crosslinked RNA in the sample. The heterocyclic derivative is selected from the group consisting of an imidazole, pyrazole, triazole or tetrazole derivative or a combination thereof. The sample is contacted with a labeled probe that is complementary to all or a part of a region of interest of the RNA in the sample, thereby producing hybridized RNA. Next, hybridized RNA is detected with the labeled probe; and the cells are differentiated based upon the detection.

In one embodiment, the heterocyclic derivative has at least one of the following structures:

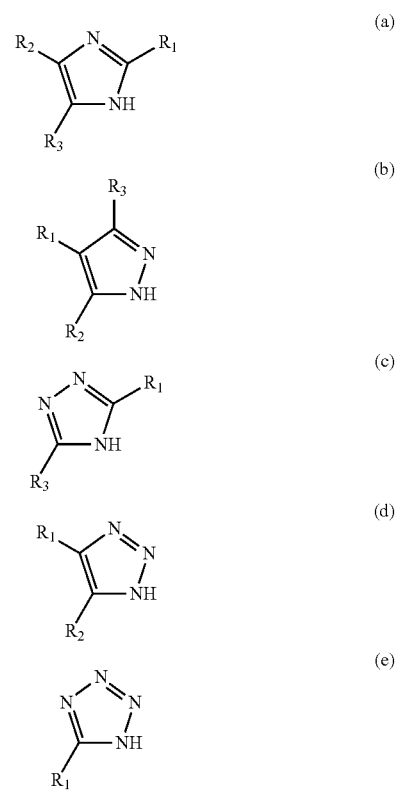

wherein $R_1$, $R_2$, and $R_3$ independently are H, alkyl, aryl, F, Cl, Br, I, CN, $NO_2$, $NH_2$, OH, SH, ethylthio-, alkyloxy-, or carbonyl. In one aspect of the invention, the aldehyde-containing fixative is formaldehyde.

In another aspect, the heterocyclic derivative is selected from the group consisting of 2-methylimidazole, imidazole, 1-hydroxyl-benzotriazole, 5-ethylthiotetrazole, and 2-chloroimidazole. In an embodiment, the heterocyclic derivative is 5-ethylthiotetrazole.

In another embodiment, the carbodiimide is selected from the group consisting of 1-ethyl-3-(3-dimethylaminopropyl) carbodiimide (EDC), 1-ethyl-3-(3-dimethylaminopropyl) carbodiimide hydrochloride (EDC-HCl), 1-cyclohexyl-3-(2- morpholinyl-(4)-ethyl)carbodiimide metho-p-toluenesulfonate (CMC), N,N'-dicyclohexylcarbodiimide (DCC), N,N'-diisopropylcarbodiimide (DIC), and 1-ethyl-3-(3-dimethylaminopropyl)-carbodiimide methiodide (EDC-MeI). In another aspect, the carbodiimide is 1-ethyl-3-(3-dimethylaminopropyl)carbodiimide hydrochloride (EDC-HCl).

In a preferred embodiment, the carbodiimide is 1-ethyl-3-(3-dimethylaminopropyl)carbodiimide hydrochloride (EDC-HCl) or 1-ethyl-3-(3-dimethylaminopropyl)carbodiimide methiodide (EDC-MeI) and the heterocyclic derivative is 5-ethylthiotetrazole.

In yet another embodiment, the 1-ethyl-3-(3-dimethylaminopropyl)carbodiimide hydrochloride (EDC-HCl) or 1-ethyl-3-(3-dimethylaminopropyl)carbodiimide methiodide (EDC-MeI) has a concentration of about 20 mM to about 300 mM.

In one aspect, the solution comprising 1-ethyl-3-(3-dimethylaminopropyl)carbodiimide hydrochloride (EDC-HCl) or 1-ethyl-3-(3-dimethylaminopropyl)carbodiimide methiodide (EDC-MeI) contacts the sample at a temperature of about 20° C. to about 70° C.

In another aspect of the invention, the solution comprising a carbodiimide and a heterocyclic derivative and has a pH of about 6.0 to about 10.0. In an alternate embodiment, the solution comprising a carbodiimide and a heterocyclic derivative has a pH of about 7.0 to about 8.0.

In yet another embodiment of the invention, the solution comprising a carbodiimide and a heterocyclic derivative further comprises a detergent. In one aspect, the detergent is selected from the group consisting of TWEEN20 (Polysorbate20), TWEEN80 (Polysorbate80), TRITON A-100 (Octylphenol ethoxylate), TRITON-114 (tert-octylphenoxypoly (ethoxyethanol)), Digitonin, Saponin, CHAPS (3-[(3-Cholamidopropyl)dimethyammonio]-1-propanesulfonate), Denhardt's solution, Heparin, BRIJ35 (Polyethylene glycol hexadecylether), Sodium dodecyl sulfate (SDS), and urea.

In another aspect, the method further includes contacting the solution comprising a carbodiimide and a heterocyclic derivative with a cyanogen halide. In one aspect, the cyanogen halide is selected from the group consisting of cyanogen bromide, cyanogen iodide, cyanogen chloride and cyanogen fluoride. In a preferred embodiment, the cyanogen halide is cyanogen bromide or cyanogen iodide.

In one embodiment, the probe comprises a locked nucleic acid residue. In another embodiment, the probe comprises a or PNA probe, or 2'-OMe probe or 2'-O-ethyl (2'-OEt) probe or 2'-O-methoxyethyl (MOE) or 2',4'-contrained MOE bicyclic nucleic acid (cMOE BNA) probe or 2',4'-contrained 2'-O-ethyl bicyclic (cEt BNA) probe or S-DNA probe residue, and the like. In one aspect, the probe further comprises a linker having a length greater than about 3.0 nm.

In one aspect of the invention, the hybridized RNA is miRNA. In another aspect, the detection further comprises quantifying said hybridized miRNA using the labeled probe.

In another embodiment, the contacting step includes a plurality of different probes, wherein each probe hybridizes to a specific type of RNA and/or protein. In one aspect of the invention, each probe has a different label.

In an embodiment, the detecting further includes quantifying the specific types of hybridized RNA and/or protein. In another embodiment, the specific types of RNA are selected from the group consisting of mRNA, rRNA, mt-mRNA, mt-rRNA, tRNA, shRNA, siRNA or Piwi-interacting RNA, or a pri-miRNA, pre-miRNA, miRNA, anti-miRNA, snRNA, snoRNA, scRNA and long ncRNA or other non-coding RNA.

In a preferred embodiment, the specific types of RNA are snRNA, snoRNA, scRNA, mt-rRNA, rRNA and mRNA.

In one aspect, U1 snRNA, U2 snRNA, U6 snRNA, U3 snoRNA, 7SL scRNA, hy3 scRNA, 7SK scRNA, rRNA, mt-rRNA, miRNA or other non-coding RNA, mt-mRNA and mRNA are quantified to calculate a ratio, and the ratio is indicative of a certain cell type. In another embodiment, the specific types of RNA and protein are quantified to calculate a ratio, and the ratio is indicative of a certain cell type. For example, the cell can be a certain type of cancer cell.

For molecular diagnostic purposes, short (e.g. miRNA) and long (e.g. mRNA) RNAs can be quantitated in clinical or biological samples using a variety of methods including barcoded RNA sequencing with reference calibration markers (here barcoded small RNA sequencing). Specific oligonucleotide probes targeting differentially expressed transcripts can be designed for subsequent fluorescence detection. These signals can be normalized against signals obtained from reference RNA molecules, such as rRNA, mt-rRNA, polyA tails (total mRNA), mt-mRNA, snRNAs, snoRNAs, scRNAs, among others.

Normalized RNA ratios can be used to differentiate specific cell types, and normal and diseased states. Within disease states, RNA ratios can be used for diagnostic, classificatory, prognostic purposes and for therapeutic monitoring.

In one embodiment, the detecting includes the use of fluorescence ISH (FISH). In another embodiment, the different probes comprise different fluorescent stains.

BRIEF DESCRIPTION OF THE DRAWINGS

FIG. 4: miR-205 and miR-375 concentrations in clinical samples. Sequencing-derived miR-205 and miR-375 concentrations (fmol/μm total RNA) are depicted for (a) all samples and (b) training set samples. miRNA microarray and real-time RT-PCR analyses of a subset of six MCC and two NS samples confirmed our sequencing-based results. Principal component analysis differentiated MCC from non-MCC(NS) groups (data not shown). miR-205 was 505-fold higher in NS than MCC (p=0.003) and miR-375 was 310-fold higher in MCC than NS (p=0.006). miR-375 real-time RT-PCR expression levels were assessed for (c) 11 MCC and 4 NS samples and were significantly higher in MCC compared to NS (ANOVA p<0.001, $N_{MCC}$=11, $N_{NS}$=4, FCH=233.5). miR-205 expression was not assessed due to paucity of material. Sequencing-derived miR-375 concentrations and real-time PCR measurements correlated strongly (Spearman correlation 0.94 (p<0.001); Pearson correlation of log 2-transformed variables 0.99 (p<0.001). Error bars indicate the standard error of the mean.

FIG. 7 discloses the core sequence of those labeled under "peptides" as SEQ ID NOS 1 and 12-16, respectively, in order of appearance, and the core sequence under "AMP-pep product" as SEQ ID NO: 1.

FIG. 16: Total RNA isolation from clinical samples. Total RNA was isolated from FFPE BCC, MCC (ten primary and two metastatic), and NS tissues, and freshly cultured MCC-derived cell lines using three different RNA extraction methods. Sample replicates are denoted by the suffixes a-c. FFPE tissue roll thickness in microns is indicated in superscript. Immunohistochemical staining was performed for carcinoembryonic antigen (CEA), chromogranin (CHR), cytokeratin 7 (CK7), cytokeratin 20 (CK20), epithelial membrane antigen (EMA), leukocyte common antigen (LCA), low molecular weight keratin (LMWK), neuron-specific enolase (NSE), neurofilament (NF), synaptophysin (SYN), and thyroid transcription factor 1 (TTF-1). MCV status is indicated where available. NA denotes measurement not available. NT denotes not tested.

FIG. 17: Small RNA sequence read counts and annotation. miRNA expression profiles were generated for all 36 samples in two barcoded sequencing runs. Total sequence reads per sample averaged 395,855 (range: 121,271-649,145) and were similar for each run, respectively averaging 379,502 (range: 121,271-556,983) and 416,297 (range: 193,092-649,145) sequence reads. Following barcode extraction, sequence reads were annotated into the following RNA categories: calibrator (spiked in calibrator oligoribonucleotides for miRNA quantitation), miRNA, none (sequences with unclear or no match to the human genome), rRNA, transfer RNA (tRNA), miscellaneous RNA (miscRNA: poorly annotated non-coding RNA transcripts), and marker RNA (size marker RNAs that were used for isolating ligation products during cDNA library preparation). Following annotation, miRNA was the most abundant (average 78.9%, range: 45.8-93.6%) small RNA class in each sample. The sum of proportions may not equal 100 due to rounding errors.

FIG. 18: Total and specific miRNA concentrations in clinical samples. Total miRNA and specific miRNA-205 and miR-375 concentrations were derived for all samples. Relative miR-375 expression levels, derived from real-time RT-PCR measurements, indicate relative fold expression in each sample over a reference value (arbitrarily set at 1) from an NS sample. NT denotes not tested.

FIG. 19: Optimized condensation reaction conditions using different carbodiimide derivatives. Four different carbodiimide derivatives (0.1 M) were tested to identify optimal reaction conditions for phosphate activation while minimizing hydrolysis in 1-methylimidazole buffer (0.1 M 1-methylimidazole, 0.3 M NaCl, pH 8.0). Despite the shorter reaction time for EDC-MeI, we selected EDC-HCl to avoid overcrosslinking, which would decrease access of antibody-based signal amplification reagents to the target-RNA-bound probe-conjugated.

FIG. 20: Optimized condensation reaction conditions using different heterocyclic derivatives and EDC-HCl. Five different heterocyclic derivatives (0.1 M) combined with EDC-HCl (0.1 M) in 1-methylimidazole buffer (0.1 M 1-methylimidazole, 0.3 M NaCl, pH 8.0) were tested to identify optimal reaction conditions for minimizing hydrolysis through intermediate formation. For miRNA FISH experiments, we selected EDC-HCl and 5-ETT in 1-methylimidazole buffer (pH 8.0).

FIG. 21: miR probe and rRNA sequences and melting temperatures of miRNA and rRNA duplexes. (a) Several probes were designed to detect miR-205 (sense RNA sequence: 5'UCCUUCAUUCCACCGGAGUCUG (SEQ ID NO: 4)) and miR-375 (sense RNA sequence: 5'UUUGUUCGUUCGGCUCGCGUGA (SEQ ID NO: 5)); LNA residues are indicated in lowercase letters. Probe sequences that were used in the current study are highlighted in blue. FIG. 21(a) discloses SEQ ID NOS 29-30, 10, 31-35, 11 and 36-38, respectively, in order of appearance. (b) Four probes were designed to detect human 28S rRNA. The sense RNA sequences for LNA1, LNA2, LNA3 and LNA4 are 5'AUCAGACCCCAGAAAAG (SEQ ID NO: 6), 5'CGGAACGGGACGGGA (SEQ ID NO: 7), 5'AGUCGGUCCUGAGAGAUG (SEQ ID NO: 8) and 5'UCAGUACGAGAGGAACC (SEQ ID NO: 9), respectively. These probes were synthesized on 3'-amino-modifier C7 CPG (500 Å) solid glass support, deprotected, and conjugated to ATTO-647N-NHS ester. Melting temperatures were measured using 50% formamide, 1 M NaCl, and 50 mM phosphate (pH 7.0) and probe concentrations were 1.5 µM. Based on melting temperatures of the probes highlighted in blue, we determined the hybridization temperature to be 55° C. in miRNA FISH experiments. FIG. 21(b) discloses SEQ ID NOS 21-24, respectively, in order of appearance.

FIG. 22 discloses SEQ ID NOS 33, 35 and 11, respectively, in order of appearance.

FIG. 25. miRNA signal normalization and establishment of cut-off values to enable tumor differential diagnosis. Mean signal intensities for miR-375, miR-205, and rRNA and the sum of pixels (encompassing the interval from 1,000 to 10,000 pixel intensities representing specific RNA signal and excluding background signal) for five BCC and thirteen were recorded for miR-375, miR-205, and rRNA. Exposure times for miR-375, miR-205, and rRNA were 50, 100, and 250 ms, respectively.

FIG. 26. Fluorescent dyes and their properties, and filters for fluorescent imaging. Specific fluorescent dyes were used to identify DNA (nuclei) and RNA (miR-375, miR-205 and rRNA) targets in our study. Excitation (Ex.) and emission (Em.) wavelengths and the quantum yield (QY) of each dye, and the excitation and emission filters for the Sedat Quad filter set are indicated.

FIG. 28 discloses SEQ ID NOS 29 and 10, respectively, in order of appearance.

FIG. 34. Additive detection of probe signal intensities using RNA FISH. Eight oligonucleotide probes targeting different regions of mouse 28S rRNA were assessed separately (B-I), in combination (J), and in their absence (A), in neurons of mouse brain cortex using RNA FISH. Probe signal intensities (listed in FIG. 35) for this probe set were detected in an additive fashion. All probes (100 nM) were hybridized at 55° C. for 16 h in hybridization buffer containing 50% formamide and 1.0 M NaCl.

FIG. 35. Mouse 28S rRNA probe sequences. Eight oligonucleotide probes were designed to detect mouse 28S rRNA in neurons of mouse brain cortex using RNA FISH; LNA residues are indicated in lowercase letters. Signal intensities were recorded for each probe separately (RNA1-RNA8), in combination (rRNA1-8), and in their absence (blank). Signal intensity for each probe was approx. 100 times higher than that of the no probe (blank) control. Pooling all 8 probes yielded a signal intensity that was 8 times higher that that for an individual probe, indicating that RNA FISH can be used for accurate target quantitation. Melting temperatures for select probes are shown; melting temperature was measured using 50% formamide, 1 M NaCl, and 50 mM phosphate (pH 7.0) and probe concentrations were 1.5 µM. All probes (100 nM) were hybridized at 55° C. for 16 h in hybridization buffer containing 50% formamide and 1.0 M NaCl. FIG. 35 discloses the "rRNA" sequences as SEQ ID NOS 39-42, 7 and 43-45, respectively, in order of appearance, and the "LNA" sequences as SEQ ID NOS 46, 21, 3, 47, 22-23, 48 and 24, respectively, in order of appearance.

FIG. 36. Detection of mRNA-associated polyA tails in FFPE mouse brain. Four oligonucleotide probes (polyT1-4, for sequences see FIG. 37) were designed to target mRNA-associated polyA tails in oligodendrocytes (characterized by scant cytoplasm) in FFPE mouse brain. polyT1 likely targets proteins to highlight dendritic bundles (B). Specific cellular signals are seen with polyT2-4 (E, H, K) with polyT4 (K) producing a distinct signal without highlighting dendritic bundles, therefore polyT4 is preferred probe to target polyA tails. Nuclear DAPI (A, D, G, J) and nucleocytoplasmic rRNA (C, F, I, L) signals were similar for each probe. Probes were hybridized using 50% Formamide and 1M NaCl at 50° C. Exposure times are indicated in ms. Scale bar, 100 µm, (A-L).

FIG. 37. Poly T probe sequences and normalized signal intensities. 4 oligonucleotide probes were designed to detect polyA tail in PEFF mouse brain using RNA FISH; LNA residues are indicated in lowercase letters. Signal intensities were recorded for each probe separately. Melting temperature for polyT1 is shown; melting temperature was measured using 50% formamide, 1 M NaCl, and 50 mM phosphate (pH 7.0) and probe concentrations were 1.5 µM. All probes (100 nM) were hybridized at 50° C. for 16 h in hybridization buffer containing 50% formamide and 1.0 M NaCl. Normalized intensity=intensity of polyT/intensity of rRNA. polyT4 is preferred probe to target polyA tails. FIG. 37 discloses SEQ ID NOS 49-52, respectively, in order of appearance.

FIG. 38. Comparison of non-coding RNA, their sequencing counts from small RNA sequencing and normalized intensity derived from RNA FISH. Read counts were determined using approx. 2000 small RNA cDNA libraries from various tissues. All probes were conjugated to the same ATTO-550 dye and the intensity was measured using the same window size with ca. 200 cells. Comparing intensities, the ratios between non-coding RNAs are similar to the ratios can be calculated from read counts/transcript length. This demonstrates that the same relative abundance of RNAs can be determined by read counts and measured intensities by RNA FISH indicating that pool of 7 non-coding RNAs can be used to determine both RNA retention and abundance of RNAs in a tissue sample. This parameters can be subsequently used to design specific probes for mRNA targets. The table also shows that abundant RNAs such as ACTB, RPL8 and EEF2 are still 250 to 2,500 times less abundant than non-coding RNAs (from mt-rRNA to rRNA), therefore, the probes targeting mRNAs must be design avoiding mishybridization to these non-coding RNAs. Normalized intensity=total intensity/number of probes/exposure time (ms).

FIG. 42. Comparative detection of HER2-ERBB2 in breast cancer cell lines using IHC and RNA FISH. HER2 was detected in HER2 positive (HCC-1954) and HER negative (MDA-MB231) cell lines using either IHC or RNA FISH. Positive IHC (brown) and RNA FISH (green) signals were seen as expected in HER2 positive (A, D) but not HER2 negative (B, E) cells. Mixtures of cells yielded the expected mixture of signals (C, F). rRNA (red) and nuclei (blue) were visualized using rRNA probes and DAPI stain (D-F). Probes were hybridized using 25% formamide and 1M NaCl at 45° C. Scale bar, 50 μm, (A-F).

FIG. 43. Probe sequences targeting 28S rRNA, human and mouse mt-rRNA, human U1 snRNA, U2 snRNA, hy3 scRNA, 7SL scRNA and U3 snoRNA. LNA residues are indicated in lowercase letters. All 5 probes crosshybridize to both human (hsa) and mouse (mmu) 28S rRNA. Y: 3'-PT-amino-modifier C6 CPG (Glen Research); Z: 5' Amino Modifier C6-TFA (Glen Research). FIG. 43 discloses the "RNA" sequences as SEQ ID NOS 53-108, respectively, in order of appearance, and the "LNA" core sequences as SEQ ID NOS 109-164, respectively, in order of appearance.

FIG. 44. Probe sequences targeting HER2/ERBB2. LNA residues are indicated in lowercase letters. X: Fmoc amino-modifier C6 dT Phosphoramide (GlenResearch); L: spacer 18 (GlenResearch); W: 3'-Fmoc-amino-modifier C7 CPG (Glen Research). FIG. 44 discloses the "RNA" sequences as SEQ ID NOS 165-221, respectively, in order of appearance, and the "LNA" core sequences as SEQ ID NOS 222-278, respectively, in order of appearance.

Formamide and 1M NaCl at 40, 50 and 60° C. HCC-1954 cell line could not be sufficiently distinguished from MDA-MB231 due to rRNA mishybridization of DNA probes. Only hybridization at 40° C. allowed small discrimination between the cell lines (M, N, O). At higher temperatures (A, B, C, G, H, I), rRNA mishybridization dominates the signal indicating that further denaturation of rRNA secondary structure increases rRNA mishybridization. To avoid mishybridization, the probes need to be shorter to increase their specificity. Exposure times for rRNA and HER2 were 80 ms and 200 ms, respectively. Scale bar, 50 µm, (A-R).

Figure 45A:
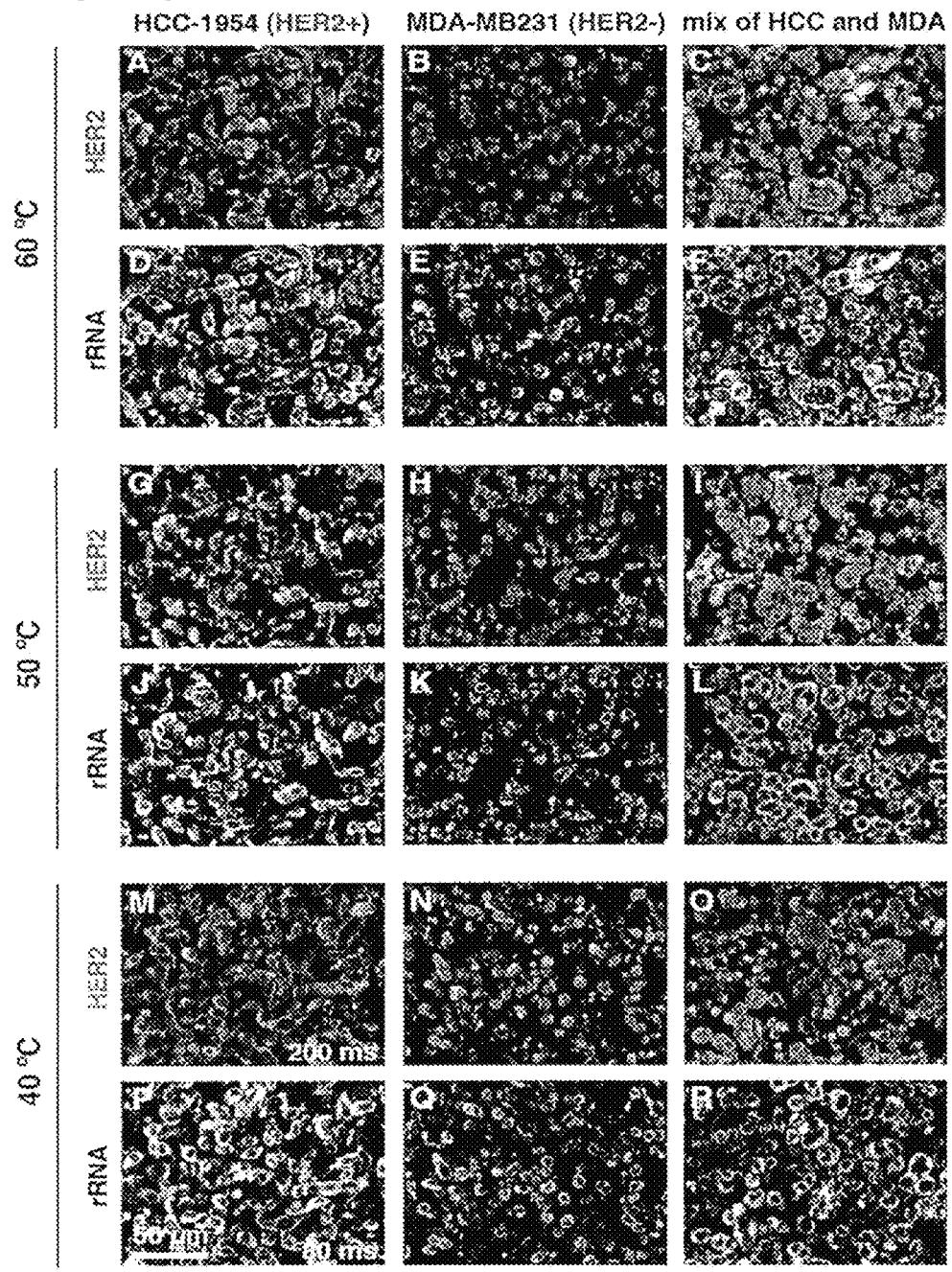
FIG. 45a. Differentiating FFPE breast cancer cell lines using RNA FISH and DNA probes (24-30 nt long). 45 DNA probes (24-30 nt long) conjugated to ATTO-550 were used to differentiate two breast cancer cell lines; HCC-1954 that is HER2 positive and MDA-MB231, which is HER2 negative. Five rRNA probes listed in FIG. 43 were conjugated to ATTO-488. The probes were designed with GC content between 50 and 64% and TC content between 45 and 66%. No special care was taken regarding probes mishybridization to rRNA. Melting temperature of these DNA probes vary from 48.1 to 56.9° C.; melting temperature was measured using 50% formamide, 1 M NaCl, and 50 mM phosphate (pH 7.0) and probe concentrations were 1.5 μM. Probes were hybridized using 25% Formamide and 1M NaCl at 40, 50 and 60° C. HCC-1954 cell line could not be distinguished from MDA-MB231 due to rRNA mishybridization of DNA probes. Exposure times for rRNA and HER2 were 80 ms and 200 ms, respectively. Scale bar, 50 μm, (A-R).
Figure 45B:
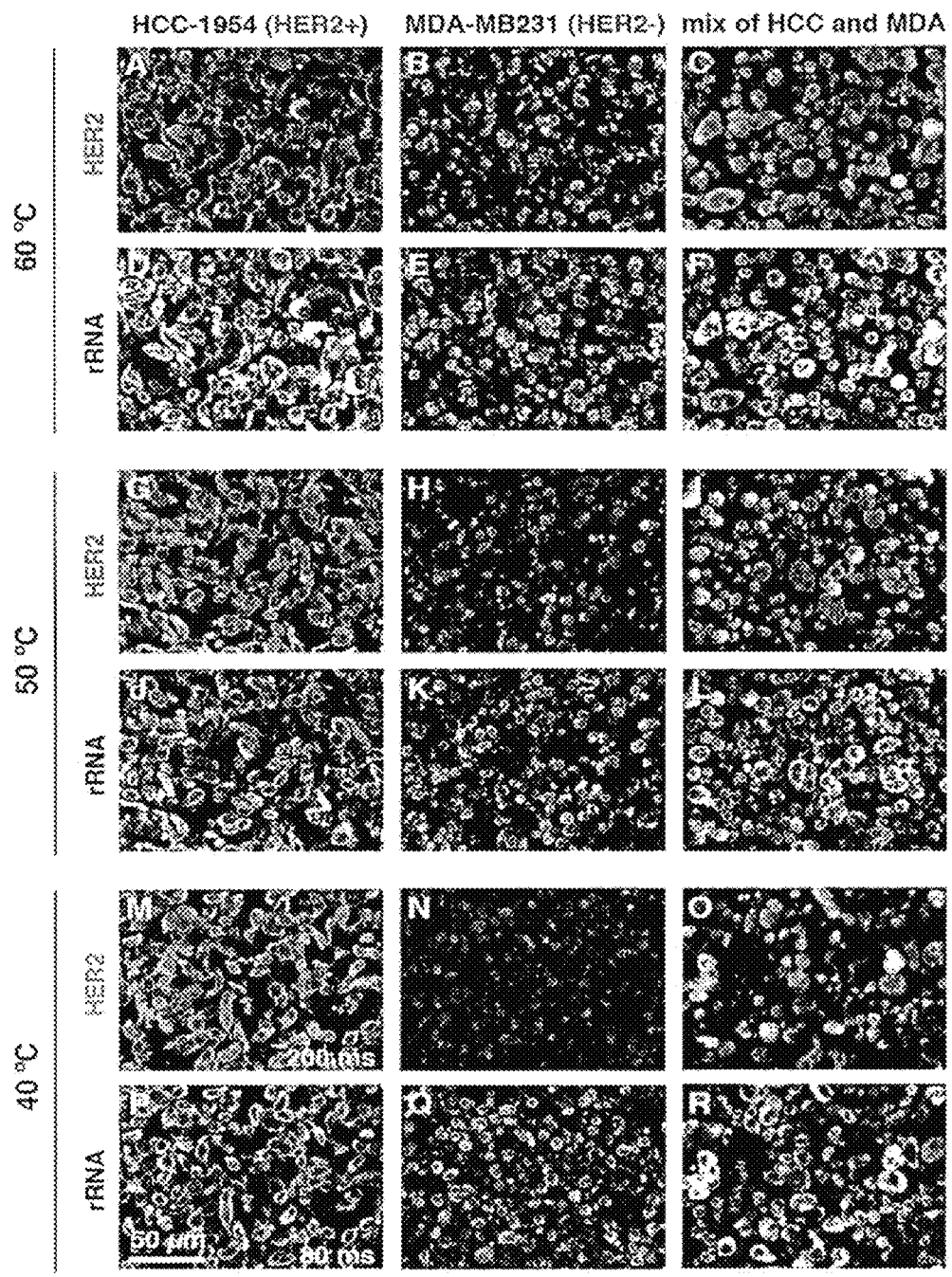
FIG. 45b. Differentiating FFPE breast cancer cell lines using RNA FISH and shorter DNA probes (14-21 nt long). 39 DNA probes (14-21 nt long) conjugated to ATTO-550 were used to differentiate two breast cancer cell lines; HCC-1954 that is HER2 and MDA-MB231. Five rRNA probes listed in FIG. 43 were conjugated to ATTO-488. Previous DNA probes (24-30 nt long) were shorten either from 5'-end or 3'-end to avoid rRNA mishybridization (no segment longer than 8 nt with rRNA sequence complementarity. Melting temperature of these DNA probes vary from 38.8 to 47.1° C. (approximately 10° C. lower than longer DNA probes (24-30 nt long); melting temperature was measured using 50% formamide, 1 M NaCl, and 50 mM phosphate (pH 7.0) and probe concentrations were 1.5 μM. Probes were hybridized using 25%
Figure 45C:
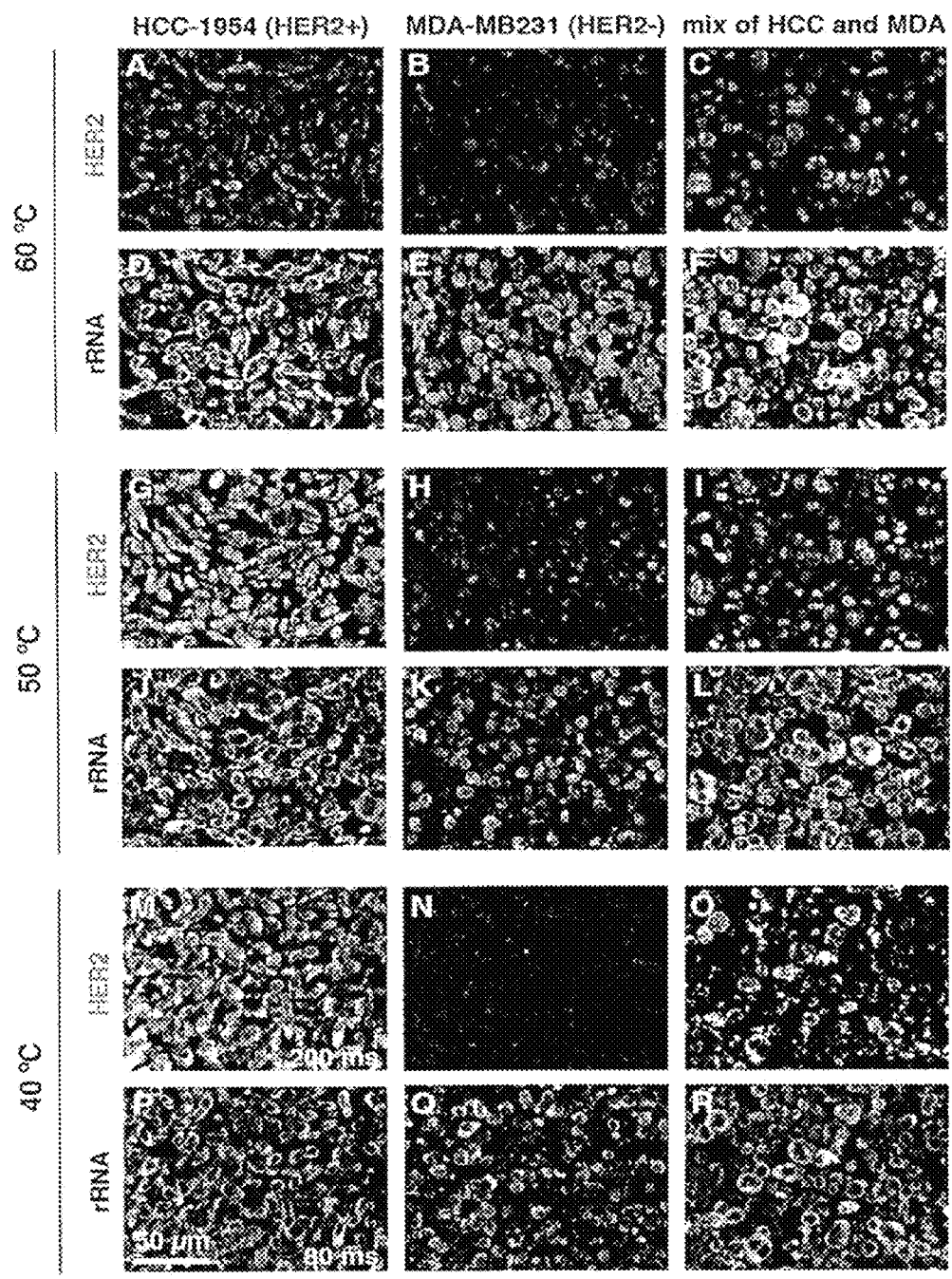

FIG. 45c. Differentiating FFPE breast cancer cell lines using RNA FISH and LNA/DNA probes (11-15 nt long). 53 LNA/DNA probes (11-15 nt long) conjugated to ATTO-550 were used to differentiate two breast cancer cell lines; HCC-1954 that is HER2 and MDA-MB231. Five rRNA probes listed in FIG. 43 were conjugated to ATTO-488. Our probe design excludes even short homology to rRNA (no segment longer than 6 nt with rRNA sequence complementarity) or other RNA sequences. The LNA residues were placed to the sequence to increase duplex stability of whole probe but not stability of 6 nt long segments, which crosshybridize to rRNA or other highly abundant RNAs. Melting temperature of these LNA/DNA probes vary from 44.2 to 52.1° C. (approximately 5° C. lower than longer DNA probes (24-30 nt long), but 5° C. higher than shorter DNA probes (14-21 nt long)); melting temperature was measured using 50% formamide, 1 M NaCl, and 50 mM phosphate (pH 7.0) and probe concentrations were 1.5 µM. Probes were hybridized using 25% Formamide and 1M NaCl at 40, 50 and 60° C. Hybridization at 40° C. (M, N, O) allowed great discrimination between HCC-1954 (HER2+) and MDA-MB231 (HER2−) breast cancer cell lines. At higher temperatures (A, B, C, G, H, I), rRNA mishybridization can be observed but does not dominates the signal indicating great specificity of LNA/DNA probes. Exposure times for rRNA and HER2 were 80 ms and 200 ms, respectively. Scale bar, 50 µm, (A-R).

Figure 46A:
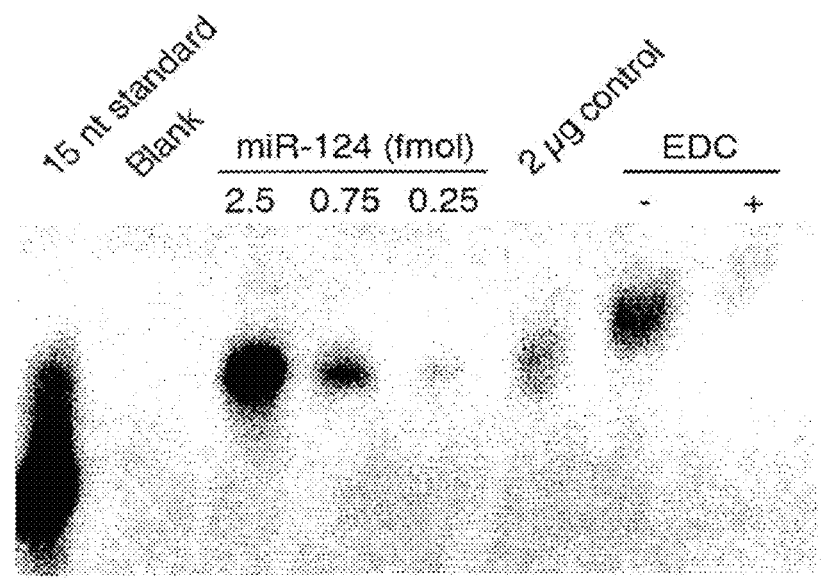
Figure 46B:
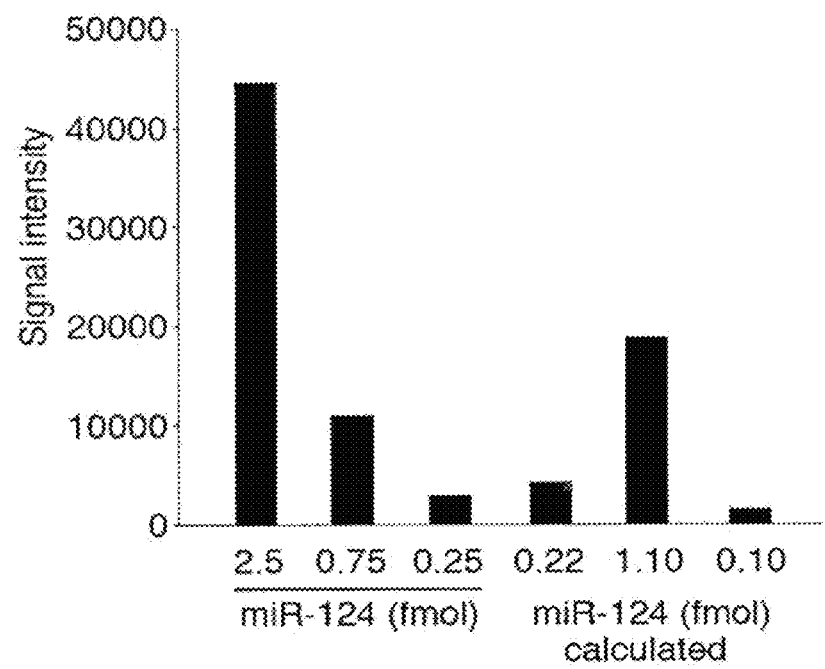

FIG. 46. miRNA retention in EDC-fixed FFPE tissues. (a) Northern blotting analysis shows substantial escape of miR-124 into ISH buffer (50% formamide, 1 M NaCl) when EDC fixation is omitted (−EDC) compared to EDC-fixed FFPE tissues (+EDC). (b) The signal intensities of three miR-124 standards were plotted against their amounts (2.5, 0.75 and 0.25 fmol) to give the linear equation y=17,325*x, where the intercept b was set to zero. The slope was used to estimate fmol amounts of miR-124 present in 2 µg total RNA from a human brain (control), and ISH buffer solutions obtained following 16 h incubation of FFPE monkey brain tissue with (+EDC) and without EDC (−EDC) fixation. Quantification of Northern blot signals shows that 0.90 fmol (corresponding to approximately 90% of total miR-124) and 0.10 fmol (corresponding to approximately 10% of total miR-124) of miR-124 were respectively present in ISH buffer from no EDC and EDC-fixed FFPE tissues, indicating that miRNA retention is substantially increased upon EDC fixation and that the EDC fixation is crucial for miRNA detection by miRNA FISH to get specific miRNA signal instead of false positive signal corresponding to rRNA- or other high abundant RNA-mishybridization.

DETAILED DESCRIPTION OF THE INVENTION

Method for Fixing

In one aspect, the invention relates to a method for fixing RNA in a biological sample. The method includes contacting the biological sample with an aldehyde-containing fixative, and subsequently contacting the sample with a solution comprising a carbodiimide and a heterocyclic derivative.

"Fixing" as used herein refers to immobilizing RNA within the biological sample. "Immobilizing" as used herein refers to binding the RNA to the biological sample such that the binding is sufficient to be stable under conditions of washing, probing, labeling, and/or analysis.

RNA may be any type RNA. Exemplary RNA includes mRNA, tRNA, rRNA, mt-mRNA, mt-rRNA, shRNA, siRNA or Piwi-interacting RNA, or a pri-miRNA, pre-miRNA, miRNA, snoRNA, scRNA, long ncRNAs, anti-miRNA, and any variants thereof. In one embodiment, the RNA is a short RNA molecule derived from a degraded source, such as, for example, degraded mRNA.

RNA may include variants thereof. A "variant" as used herein refers to (i) a portion of a referenced RNA; (ii) the complement of a referenced RNA or portion thereof; (iii) a RNA that is substantially identical to a referenced RNA or the complement thereof; or (iv) an RNA that hybridizes under stringent conditions to the referenced nucleic acid, complement thereof, or a sequences substantially identical thereto.

RNA may be synthesized as a single stranded molecule or expressed in a cell (in vitro or in vivo) using a synthetic gene. RNA may be obtained by chemical synthesis methods or by recombinant methods.

A "short" RNA refers to an RNA that has a maximum number of base pairs in length of about 100, 90, 80, 70, 60, 50, 40, 35, 34, 33, 32, 31, 30, 29, 28, 27, 26, 25, 24, 23, 22, or 21 bp. The RNA has a minimum number of base pairs in length of about 5, 6, 7, 8, 9, 10, 11, 12, 13, 14, 15, 16, 17, 18, 19, or 20 bp. Any minimum amount can be combined with any maximum amount to define a range for an RNA.

In a preferred embodiment, the RNA is microRNA (miRNA). miRNA molecules are known in the art (see, for example, Bartel, *Cell,* 2004, 116, 281-297 for a review on microRNA molecules). The definitions and characterizations of miRNA molecules in the article by Bartel are hereby incorporated by reference. Such molecules are derived from genomic loci and are produced from specific miRNA genes.

miRNAs are typically small RNA molecules of generally about 13-33, 18-24, or 21-23 nucleotides in length. The miRNA may also have a total of at about 5-40 nucleotides in length. These microRNAs are non-coding RNAs, which are cleaved from hairpin precursors. miRNAs are naturally 5' phosphorylated and carry 2', 3' dihydroxyl termini. The sequence of the miRNA may comprise the sequence of a miRNA disclosed in U.S. Pat. Nos. 7,825,229 and 7,642,348 the contents of which are incorporated herein, or variants thereof.

The source of the RNA can be any known source. In one embodiment, the source of the RNA is a biological sample. A "biological sample" as used herein refers to a sample of biological tissue or fluid that includes biomolecules. Such samples include, but are not limited to, tissue or fluid isolated from animals or plants. Biological samples also include viruses or unicellular organisms. Biological samples may also include sections of tissues such as surgical pathology (including biopsy) and autopsy samples, frozen sections taken for histologic purposes, hair, and skin. Biological samples also include explants and primary and/or transformed cell cultures derived from animal or patient tissues. Biological samples may also be blood, a blood fraction, plasma, serum, urine, pleural effusion, mucus, ascitic fluid, amniotic fluid, stool, tears, saliva, cerebrospinal fluid, cervical secretions, vaginal secretions, endometrial secretions, gastrointestinal secretions, bronchial secretions, sputum, secretions from ovarian cyst, sperm, secretions from the breast, cell line, or tissue sample.

A biological sample may be provided by removing a sample of cells from an animal, or plant, but can also be accomplished by using previously isolated cells (e.g., isolated by another person, at another time, and/or for another purpose), or by performing the methods described herein in vivo. "Animal" as used herein refers to any animal, including fish, amphibians, reptiles, birds, and mammals, such as mice, rats, rabbits, goats, cats, dogs, cows, apes and humans.

As used herein, the term "biomolecule" refers to any molecule found in a biological sample. Biomolecules include biological molecules, such as a protein, nucleic acid, carbohydrate, fat, and lipid. Exemplary RNA-binding biomolecules include polypeptides, nucleic acids, small molecules such as hormones, cytokines, and drugs. In one preferred embodiment, the biomolecule is a nucleic acid.

Contacting the Biological Sample with a Fixative

The method includes contacting the biological sample with an aldehyde-containing fixative under conditions in which a biomolecule covalently bonds to a nucleic acid, as is known in the art. Such methods are known in the art. See, e.g., Feldman, "Reactions of nucleic acids and nucleoproteins with formaldehyde," *Prog. Nucleic Acid Res Mol. Biol.* 1973, 13:1-49, which is incorporated by reference.

The aldehyde-containing fixative can include an aldehyde-based fixative alone, or in combination with other fixative agents. Exemplary fixative agents include osmium tetroxide, picric acid, dialdehyde starch, AEDP (3-[(2-Aminoethyl)dithio]propionic acid.HCl) ethanol, Ketones, Isocyanate-containing compounds to label hydroxyl-containing molecules, Woodward's reagent K (WRK) (N-ethyl-5-phenylisoxazolium-3'-sulphonate), 1,1'-Carbonyldiimidazole (CDI), Bis[2-(N-succinimidyl-oxycarbonyloxy)ethyl]sulfone (BSOCOES) and sulfo-BSOCOES, Ethylene glycol-bis(succinic acid N-hydroxysuccinimide ester) EGS, Sulfo-EGS, N,N'-Disuccinimido Carbonate (DSC), Imidoester. Modification of the 5' phosphate using EDC and other coupling reagents, Cystamine followed by DTT and a sulfhydryl crosslinker. (N-Succinimidyl 3-(2-pyridyldithio)-propionate) and LC-SPDP (Succinimidyl 6-(3-[2-pyridyldithio]-propionamido)hexanoate), SPDP modification of amines coupled to the 5' phosphate of nucleotides followed by a reducing agent, DTT, creating a sulfhydryl group attachment, and a sulfhydryl crosslinker. SATA to modify a 5'-amine derivative of oligonucleotides, forming a protected sulfhydryl for crosslinking.

Examples of an aldehyde-based fixative agent include, but are not limited to, for example, formaldehyde, a derivative of formaldehyde, paraformaldehyde, glyoxal, and glutaraldehyde.

By "biological sample" it is meant that the sample can be directly from an individual (e.g. tissue sample, biopsy, etc), or previously derived from an individual and fixed with an aldehyde-based fixative (e.g. archived samples). In the case where the sample was previously derived from an individual and already fixed with an aldehyde-based fixative, the step of contacting the biological sample with an aldehyde-containing fixative may not be necessary.

Therefore, in some embodiments, the biological sample is optionally contacted with an aldehyde-containing fixative.

Contacting the Biological Sample with Solution Comprising a Carbodiimide and a Heterocyclic Derivative Subsequent to the step of contacting a biological sample with an aldehyde-containing fixative, the method includes contacting the sample with a solution comprising a carbodiimide and a heterocyclic derivative.

Any suitable carbodiimide can be used in the methods. Both water-soluble and water-insoluble carbodiimides can be used. Exemplary suitable water-soluble carbodiimides include 1-ethyl-3-(3-dimethylaminopropyl)-carbodiimide (EDC), 1-ethyl-3-(3-dimethylaminopropyl)-carbodiimide hydrochloride (EDC-HCl), 1-ethyl-3-(3-dimethylaminopropyl)-carbodiimide methiodide (EDC-MeI), 1-cyclohexyl-3-(2-morpholinyl-(4)-ethyl)-carbodiimide metho-p-toluenesulfonate (CMC), N,N'-dicyclohexylcarbodiimide (DCC), and N,N'-diisopropylcarbodiimide (DIC), and derivatives thereof. Examples of carbodiimides include those illustrated in FIG. 19.

In a preferred embodiment, a water-soluble carbodiimide is used. For example, 1-ethyl-3-(3-dimethylaminopropyl)-carbodiimide hydrochloride (EDC-HCl) or 1-ethyl-3-(3-dimethylaminopropyl)-carbodiimide methiodide (EDC-MeI), can be used.

Non-water soluble carbodiimides can also be utilized in the methods of the invention by adding dimethylformamide (DMF), dioxane, tetrahydrofuran (THF), dimethyl sulfoxide (DMSO) or other polar (hydrophilic) aprotic organic solvent to the solution. Suitable carbodiimides for the invention can also be synthesized.

Any suitable heterocyclic derivative can be used in the methods. Examples of suitable heterocyclic derivatives include the following structures:

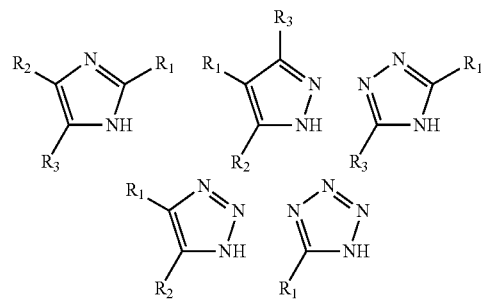

The heterocyclic derivative can be an imidazole, pyrazole, triazole or tetrazole derivative wherein $R_1$, $R_2$, and $R_3$ independently are selected from H, alkyl, aryl, F, Cl, Br, I, CN, $NO_2$, $NH_2$, OH, SH, ethylthio-, alkyloxy-, or carbonyl. Examples of heterocyclic derivatives are depicted in FIG. 20 and include 2-methylimidazole, imidazole, 1-hydroxyl-benzotriazole, 5-ethylthiotetrazole, and 2-chloroimidazole.

The carbodiimide and heterocyclic derivative solution produces crosslinking between proteins in the biological solution, which retain also long RNA species such as, for example, rRNA and mRNA.

The carbodiimide and heterocyclic derivative are in solution with a buffer. Any suitable buffer can be utilized. An exemplary buffer for a water-soluble carbodiimide includes 1-methylimidazole buffer.

The solution comprising a carbodiimide and a heterocyclic derivative has a pH of greater than about 6.0 and less than about 10.0. In a preferred embodiment, the solution comprising a carbodiimide and a heterocyclic derivative is about 7.0 to about 8.0.

In one embodiment, the solution comprising a carbodiimide and a heterocyclic derivative has a concentration of about 20 mM to about 300 mM. In another embodiment, the solution contacts the sample at a temperature of about 20° C. to about 70° C.

In another embodiment, the solution comprising a carbodiimide and a heterocyclic derivative further comprises a surfactant or detergent. Any suitable surfactant or detergent can be used in the method. For example, the surfactant or detergent can be of TWEEN20 (Polysorbate20), TWEEN80 (Polysorbate80), TRITON A-100 (Octylphenol ethoxylate), TRITON-114 (tert-octylphenoxypoly(ethoxyethanol)), Digitonin, Saponin, CHAPS (3-[(3-Cholamidopropyl)dimethyammonio]-1-propanesulfonate), Denhardt's solution, Heparin, BRIJ35 (Polyethylene glycol hexadecylether), Sodium dodecyl sulfate (SDS), and urea.

In yet a further embodiment, the solution comprising a carbodiimide and a heterocyclic derivative is further contacted with a cyanogen halide. Examples of cyanogen halides include cyanogen bromide, cyanogen iodide, cyanogen chloride and cyanogen fluoride. Preferred cyanogen halides are cyanogen bromide (CNBr) and cyanogen iodide (CNI).

Any suitable buffer can be utilized with the cyanogen halide. An exemplary buffer for a cyanogen halide includes N-morpholinoehanesulfonate (MES) buffer.

In another embodiment, a solution comprising a cyanogen halide is used in place of the solution containing a carbodiimide and a heterocyclic derivative.

Method for Detecting

In another aspect, the invention relates to a method for detecting a target RNA in a biological sample. The method includes contacting the biological sample with solution comprising an aldehyde-containing fixative and subsequently contacting the sample with a solution comprising a carbodiimide and a heterocyclic derivative to produce a cross-linked RNA and protein. The method further includes contacting the cross-linked RNA with a probe, said probe being complementary to all or a part of a region of interest of the RNA, thereby producing a hybridized RNA. The method also includes detecting the hybridized RNA as the target RNA.

"Detecting" refers to determining the presence of a component in a sample. Detection may also mean determining the absence of a component. Detection may also mean measuring the level of a component, either quantitatively or qualitatively.

A "target RNA" as used herein refers to any RNA that is to be identified, fixed, or otherwise analyzed. The target RNA may be any type of RNA including mRNA, mt-mRNA, tRNA, rRNA, mt-rRNA, shRNA, siRNA or Piwi-interacting RNA, or a pri-miRNA, pre-miRNA, miRNA, snRNA, snoRNA, scRNA, long ncRNAs, anti-miRNA, and any variants thereof. In one embodiment, the target RNA a short RNA molecule derived from a degraded source, such as, for example, degraded mRNA. In a preferred embodiment, the target RNA is miRNA.

As stated above, subsequent to fixing or cross-linking, the method includes contacting the cross-linked RNA with a probe. In one embodiment, one or more probes may be used to bind to the target RNA.

The probe is capable of binding to a target RNA of complementary sequence or a substantially complementary sequence through one or more types of chemical bonds, usually through complementary base pairing, usually through hydrogen bond formation. Probes may bind to RNA without complete complementarity to the probe sequence, depending upon the stringency of the hybridization conditions.

In a preferred embodiment, the probe has 100% complementarity to all or a portion of a region of interest of the target RNA. "Complement" or "complementary" as used herein refers to Watson-Crick (e.g., A-T/U and C-G) or Hoogsteen base pairing between nucleotides or nucleotide analogs of nucleic acid molecules.

"Substantially complementary" used herein may mean that a first sequence is at least 50%, 55%, 60%, 65%, 70%, 75%, 80%, 85%, 90%, 95%, 97%, 98% or 99% identical to the complement of a second sequence over a region of 2, 3, 4, 5, 6, 7, 8, 9, 10, 11, 12, 13, 14, 15, 16, 17, 18, 19, 20-40, 40-60, 60-100, or more nucleotides, or that the two sequences hybridize under stringent hybridization conditions.

The site on the target RNA on which the probe binds is the "target binding site." The target binding site may be 5-100 or 10-60 nucleotides in length. The target binding site may include a total of 5, 6, 7, 8, 9, 10, 11, 12, 13, 14, 15, 16, 17, 18, 19, 20, 21, 22, 23, 24, 25, 26, 27, 28, 29, 30-40, 40-50, 50-60, 61, 62 or 63 nucleotides. Any minimum amount can be combined with any maximum amount to define a range for a target binding site.

The probe is preferably contacted with the biological sample under stringent hybridization conditions. "Stringent hybridization conditions" used herein may mean conditions under which a first nucleic acid sequence (e.g., probe) will hybridize to a second nucleic acid sequence (e.g., target RNA), such as in a complex mixture of nucleic acids. Stringent conditions are sequence-dependent and will be different in different circumstances. Stringent conditions may be selected to be about 5-30° C. lower than the thermal melting point ($T_M$) for the specific sequence at a defined ionic strength pH. The $T_M$ may be the temperature (under defined ionic strength, pH, and nucleic concentration) at which 50% of the probes complementary to the target hybridize to the target sequence at equilibrium (as the target sequences are present in excess, at $T_M$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.5 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

The probe may be a DNA, RNA, locked nucleic acid (LNA), 2'-O-methyl (2'-OMe), peptide nucleic acid (PNA), phosphorothioate-linked DNA (S-DNA), 2'-fluoro (2'-F) or Morpholino probe, 2'-O-ethyl (2'-OEt), or 2'-O-methoxyethyl (MOE), 2',4'-contrained MOE bicyclic nucleic acid (cMOE BNA), or 2',4'-contrained 2'-O-ethyl bicyclic (cEt BNA), or the like. The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe is preferably about 10 to 30 nucleotides in length, more preferably 18-25 nucleotides in length. Any minimum amount can be combined with any maximum amount to define a range for a probe. Examples of probes are depicted in, for example, FIGS. 15, 21, 35, 37, 43 and 44.

The probe may be directly labeled or indirectly labeled. A "label" as used herein refers to a composition that is detectable by spectroscopic, photochemical, biochemical, immunochemical, chemical, and/or physical means. For example, suitable labels include $^{32}P$, fluorescent dyes, electron-dense reagents, enzymes (e.g., as commonly used in an ELISA), biotin, digoxigenin, fluorescein, 2,4-dinitrophenol (DNP) or haptens and other molecules that can be made detectable.

The label may be a fluorophore, such as described in U.S. Pat. No. 6,541,618. The label may also be a quencher molecule, which when in proximity to another label, may decrease the amount of detectable signal of the other label, such as described in U.S. Pat. No. 6,541,618. The label may be incorporated into nucleic acids and proteins at any position of the nucleic acids or proteins.

Examples of direct labeling, such as chemical labeling, include Kreatech ULS chemical labeling technology, which labels miRNA or probes or target nucleic acids with biotin. Another example of direct labeling is part of a PerkinElmer Micromax™ Direct Labeling Kit, which labels miRNAs with biotins along the length of the miRNA. An example of enzymatic End labeling includes ligation of dinucleotides with a biotin entity (pCU-bio). Signal amplification, such as Tyramide signal amplification (TSA) amplifies the number of biotins in site, starting from one biotin to which a Streptavidin-horse radish peroxidase (HRP) conjugate is bound. The Tyramide biotin substrate is processed by the HRP to produce a non-soluble biotin that is precipitated in site, creating a cluster of biotins on the appropriate microsphere.

The probe may further include a linker. The linker exits between the probe and the label. The linker may be about 1.2 to about 200 nm in length. Preferably, the linker may be about 3.0 to about 100 nm in length. More preferably, the linker is about 30 nm in length. The linker may not be capable of forming a stable secondary structure, may not be capable of folding on itself, or may not be capable of folding on a non-linker portion of a nucleic acid contained in the probe. The sequence of the linker may not appear in the genome of the animal from which the probe non-linker nucleic acid is derived. Exemplary linkers can be found in FIG. 12.

In addition to contacting the cross-linked RNA with a probe, the method may further include contacting the biological sample with a probe complementary to all or a part of a region of interest of another target RNA in the biological sample, thereby producing a hybridized target RNA.

Accordingly, in one embodiment, more than one target nucleic acid may be hybridized with a probe and identified. In a further embodiment, multiple probes with different labels can be hybridized to different target RNA. For example, a probe can be used that hybridizes to a miRNA of interest, concurrently with another probe that hybridizes to a RNA that is degraded mRNA and/or an mRNA variant. The identification of a specific probe or a combination of different probes can be used to identify the phenotype of the cell, for example whether the biological sample is a type of cancer.

The invention also provides a method for direct visualization of rRNA, mt-rRNA, U1 snRNA, U2 snRNA, U6 snRNA, U3 snoRNA, 7SL scRNA, hy3 scRNA, 7SK scRNA or other non-coding RNA, mRNA and polyA tails by using fluorescently labeled probes and fluorescently labeled polyT probe, respectively. In addition, a method for assessing RNA retention and specificity for probe hybridization has been discovered.

Kit

In another aspect, the invention relates to a kit for fixing RNA in a biological sample. The kit includes a support substrate for holding the sample, an aldehyde-containing fixative, and a carbodiimide and a heterocyclic derivative.

A "support substrate" refers to a composition that is amenable to at least one detection method and contains individual sites that are appropriate for attachment or association of the biological sample, probe, and nucleic acid. Exemplary support substrates include glass, modified or functionalized glass, plastics (including acrylics, polystyrene and copolymers of styrene and other materials, polypropylene, polyethylene, polybutylene, polyurethanes, Teflon J, etc.), polysaccharides, nylon or nitrocellulose, resins, silica or silica-based materials including silicon and modified silicon, carbon, metals, inorganic glasses and plastics. The substrates may allow optical detection without appreciably fluorescing.

Preferably, the support substrate is one to which the biological sample may be bound. The binding of the biological sample to the support substrate may be covalent or non-covalent. Covalent bonds may be formed directly between the probe or biological sample and the solid support or may be formed by a cross-linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

The kit may also include any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. For example, the kit may be a kit for the fixation, amplification, detection, identification or quantification of a target nucleic acid sequence.

Method of Differentiating Cells

In another aspect, a method is provided for differentiating cells in a biological sample. The method for differentiating cells includes the method of detection as described above. The method can be performed on any type of cell, such as, for example, cancer cells.

In one embodiment, cells are differentiated by assessing the differences between the level of miRNA that is hybridized in each cell. Probes which are complementary to specific miRNA can be used. As discussed above, the probes can also include a label. The levels of miRNA expression can therefore be measured by determining the amount of label present. For example, the miRNA can be measured using fluorescence in situ hybridization (FISH). Cells can be differentiated by assessing the miRNA concentration in each cell and comparing the concentrations in the cells.

In another embodiment, a plurality of probe types can be used. Each probe can be complementary to a different type of RNA. As discussed above, the hybridized RNA of interest can be any RNA. In addition, each probe type can have a different label, thereby permitting the detection of the different types of RNA. In a preferred embodiment, the differentiation of cells is based upon the detection of different types of RNA in the different cells.

For example, the target RNA can be rRNA, mt-rRNA, U1 snRNA, U2 snRNA, U6 snRNA, U3 snoRNA, 7SL scRNA, hy3 scRNA, 7SK scRNA, polyA and mRNA, with different probes being complementary to each RNA type. The different probes can also include different labels L such that the expression of each RNA type can be quantified by measuring the presence of the different labels. Ratios of the different RNA types can then be quantified that are indicative of a particular cell type. The cells in the biological sample can be differentiated based upon the different ratios of RNA type.

Figure 13:
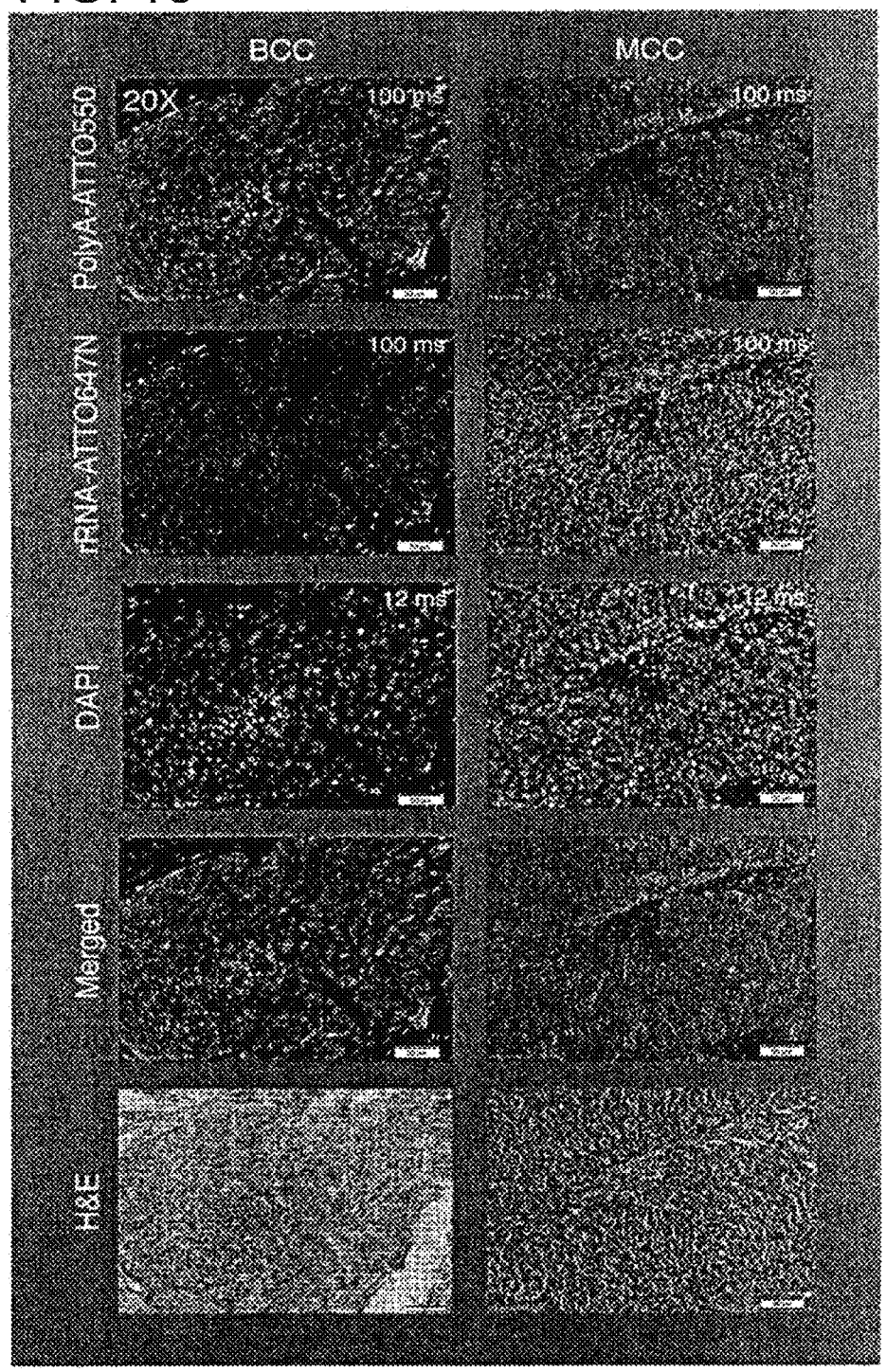
FIG. 13: Poly A and rRNA signal ratios. Comparison of Poly A and rRNA fluorescence markers versus hematoxylin-eosin staining for delineating cytoarchitecture. Fluorescence ratios in MCC and BCC show distinct signals and enable molecular classification.

By this method, differentiation between cell types, such as cancer cells, can be determined. For example, differentiation between Merkel cell carcinoma (MCC) and basal cell carcinoma (BCC) based on polyA:rRNA signal ratios can be accomplished. The ratio of polyA:rRNA has been shown to be approximately three times in higher in BCC than MCC, indicating tumor-specific changes in global markers of RNA regulation (FIG. 13). PolyA and rRNA signals potentially serve as surrogate markers of transcriptional and translational activities, respectively, and may be useful normalization controls against which gene-specific expression can be assessed.

Figure 14:
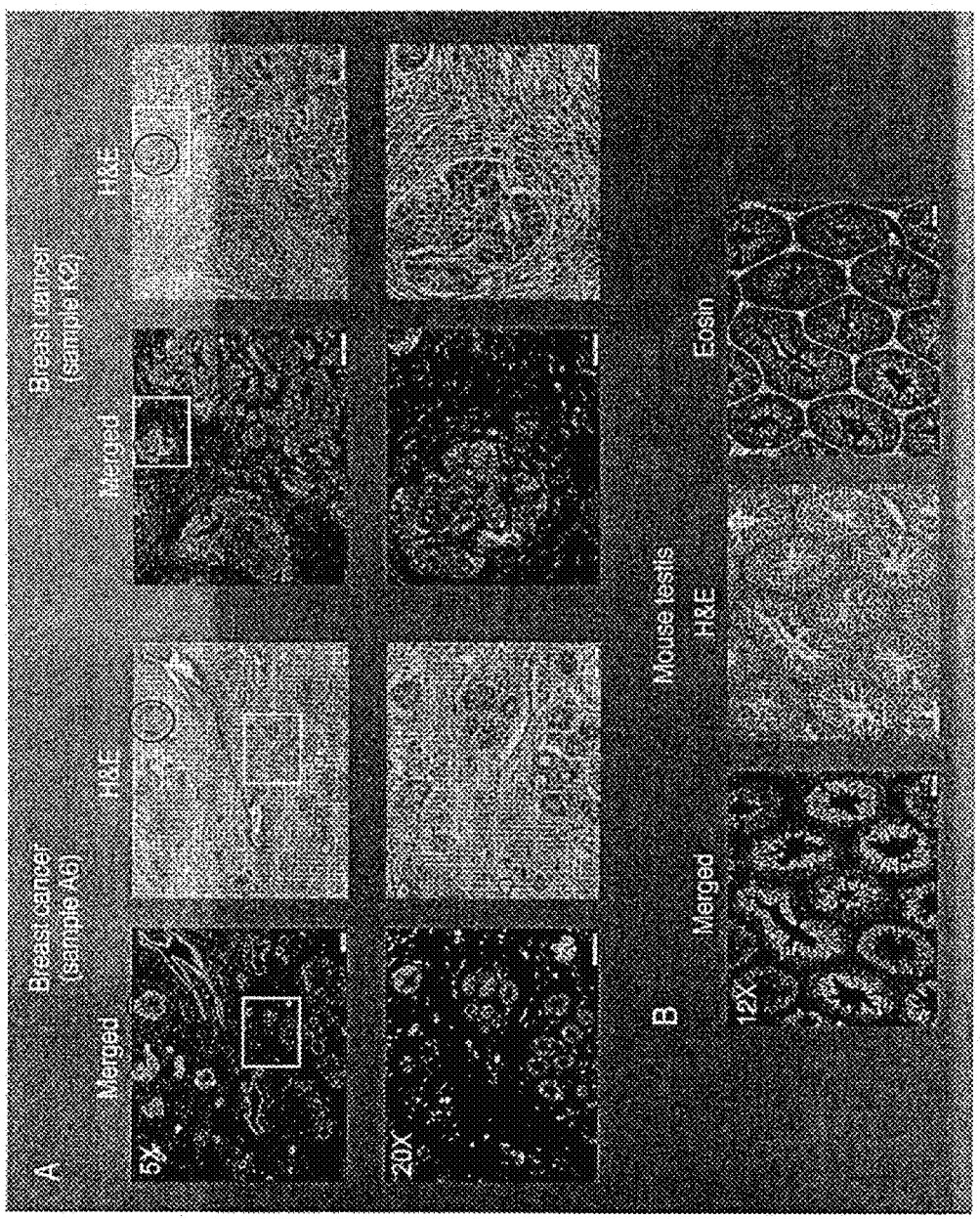
FIG. 14: PolyA and rRNA signals in breast cancer and mouse testis tissues. Comparison of PolyA and rRNA fluorescence markers versus hematoxylin-eosin (H&E) staining for delineating cytoarchitecture. (a) PolyA vs. rRNA ratio enabled differentiation of two histologically similar breast cancers. We examined the cytoarchitecture of two well-characterized breast carcinomas and compared PolyA and rRNA fluorescence signal detection with conventional hematoxylin-eosin (H&E) stain. Both tissue specimens were obtained from breast cancer patients with absence of distant metastases, and were diagnosed as ER and HER2 positive invasive ductal carcinomas of poor histological grade. Even though both specimens share the same histological classification and the tumors look identical using H&E stains (in blue circle), the patient corresponding to specimen A6 developed distant metastases and did not survive, whereas the patient contributing specimen K2 was disease free at the 5 year time point. RNA fluorescence ratios in breast cancer samples A6 and K2 are distinct (greenish (polyA high; rRNA low) for A6, orange (polyA low; rRNA low) for K2, indicating higher transcription in sample A6) and could potentially provide an additional layer of molecular classification that better correlates with prognosis. (b) The major cells types and the epithelial developmental phase of each tubule in mouse testis can be differentiated by polyA vs. rRNA vs. protein fluorescent signals (triple ratio). Distinct stages of spermatogenesis in mouse testis can be distinguished based on unique fluorescence ratios. Spermatogonia, primary and secondary spermatocytes and spermatozoa were all identified. Furthermore, protein staining using Eosin B as a fluorescent dye highlights yellowish (rRNA high; polyA low; protein very high) testosterone-producing Leydig cells between the seminiferous tubules. The staining also enables rapid determination of the epithelial developmental phase of each tubule. Spermatogonia can be seen as reddish (rRNA high; polyA low; protein low), small, round, single-layer cells at the periphery of the tubule. Primary spermatocytes appear orange (rRNA high; polyA high; protein low), larger cells immediately adjacent to the spermatogonia. Secondary spermatocytes are small, round, brilliantly green (rRNA low; polyA very high; protein low) cells adjacent to the primary spermatocytes. Spermatozoa are distinguished by the narrow, blue, elongated nuclei and yellow-staining tails.
Figure 15A:
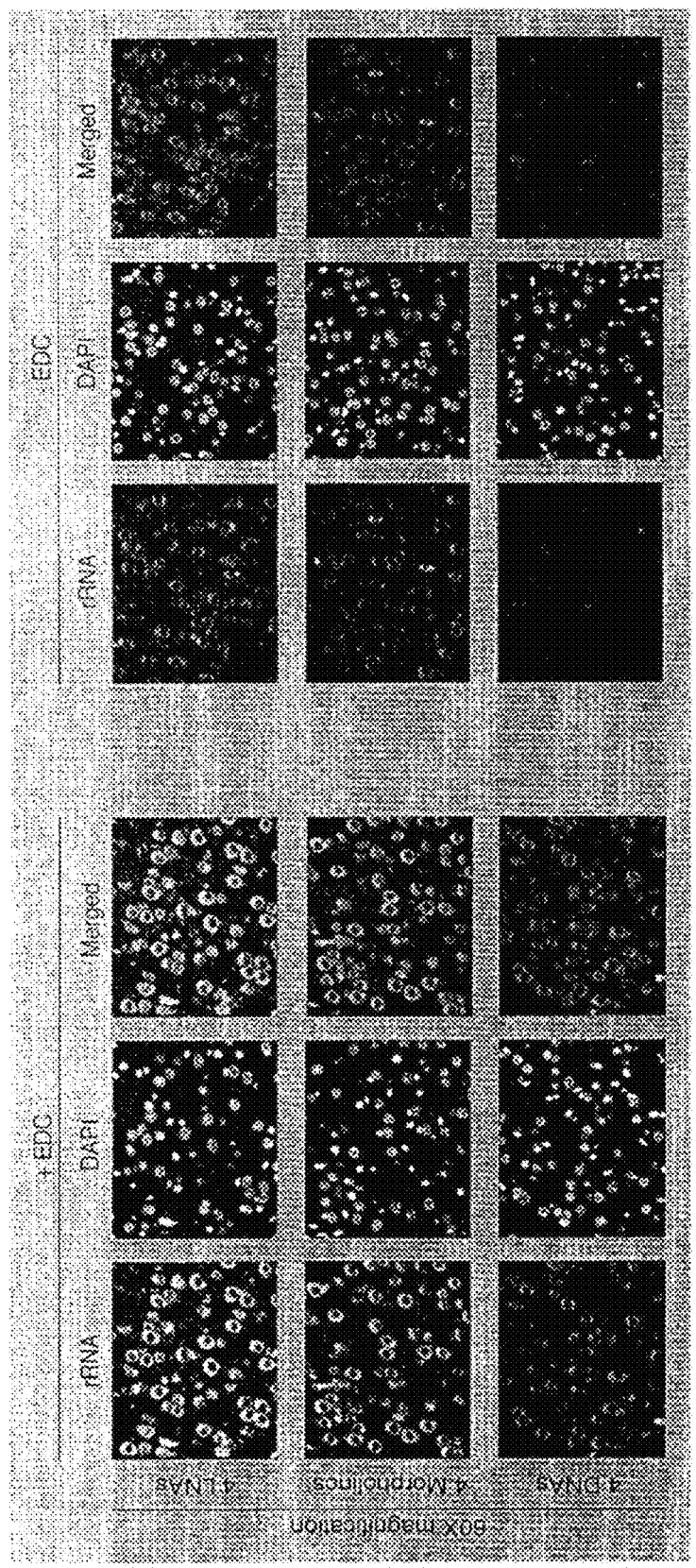
FIG. 15: Comparison of different nucleic acid backbones in RNA FISH of adult mouse brain. (a) 4 LNA, Morpholino or DNA probes (17-18 nt long) were conjugated with fluorescent dye ATTO-532 and hybridized to 28S rRNA at 50° C. for 16 h using hybridization buffer containing 25% or 50% formamide and 1 M NaCl. The images were recorded using Olympus microscope and exposure time of 40 ms. Use of EDC fixation in RNA FISH protocol increased measured signal intensity of rRNA indicating that RNA retained in the tissue. (b) Comparison of different nucleic acid backbones by measured intensities demonstrates different binding affinity of LNA, Morpholino and DNA (From highest to lowest) also affected by different duplex melting stability. Signal intensity of Morpholino in 25% formamide-based hybridization buffer was similar to signal intensity of LNA probes. For DNA, only elongation of the probes and use of 25% f formamide increased signal intensity comparable to the one of LNAs. (c) Melting temperatures of the duplexes containing different nucleic acids. (d) Sequences of target rRNA (SEQ ID NOS 6-9, respectively, in order of appearance) and antisense DNA, Morpholino (SEQ ID NOS 17-20, respectively, in order of appearance) or LNA (SEQ ID NOS 21-24, respectively, in order of appearance) probes. Lower case letter indicate incorporation of LNA modification.
FIG. 15(d) also discloses the "Antisense Long DNA" sequences as SEQ ID NOS 25-28, respectively, in order of appearance.
Figures 15B, 15C:
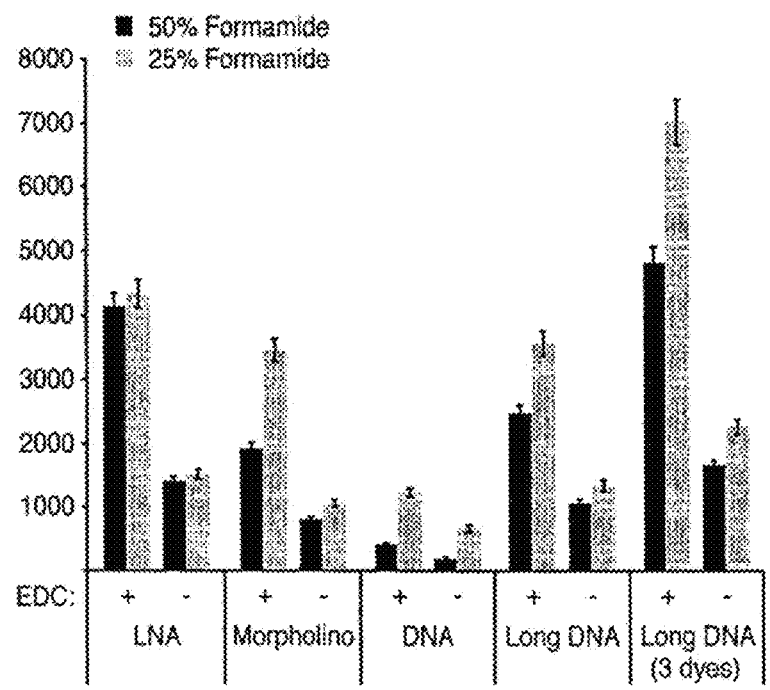

In another embodiment, the method of differentiating cells can further include the use of protein stain so as to provide a signal ratio of polyA:rRNA:protein (herein referred to as "triple ratio"). The polyA:rRNA ratio also enables differentiation between two breast cancers, see FIG. 14. In FIG. 14b, fluorescence ratios in mouse testis demarcate cellular layers that correspond to different stages of spermatogenesis. Furthermore, protein stain using Eosin B as a fluorescent dye highlights the Leydig cells between the seminiferous tubules. The major cells types of the testis can be differentiated by using a polyA vs. rRNA vs. protein comparison.

In a further embodiment, the labels can be visualized by using a suitable fluorescent stain. Exemplary protein stains include, for example, Eosin B; LUCY 565 from Sigma, Sypro Ruby from Bio-rad, Deep purple from GE and Krypton Infrared from Thermo Scientific, Eosin Y, Ethyl eosin, LUCY 506 from Sigma, LUCY 569 from Sigma, SYPRO Orange from Invitrogen, SYPRO Tangerine from Invitrogen, SYPRO Red from Invitrogen, Krypton Orange from Thermo Scientific, Oriole from Bio-Rad, Flamingo from Bio-Rad, and LavaPurple from Serva electrophoresis.

Exemplary RNA stains include, for example, directly labeled LNA probe, or DNA probe, or RNA probe, or Morpholino probe, or PNA probe, or 2'-OMe probe or 2'-O-ethyl (2'-OEt) probe or 2'-O-methoxyethyl (MOE) or 2',4'-contrained MOE bicyclic nucleic acid (cMOE BNA) probe or 2',4'-contrained 2'-O-ethyl bicyclic (cEt BNA) probe or S-DNA probe, or the like, directly labeled with any suitable dye, including for example, ATTO dye, or Cy dye or Alexa dye or BODIPY dye or DyLight dye or Cyto dye or Seta dye or RadiantDy dye or CF dye, or any fluorophore (e.g. Fluorescein and FITC).

PolyA stain can be a polyT probe (about 10 to 300 nucleotide long), and also a directly labeled LNA probe, or DNA probe, or RNA probe, or Morpholino probe, or PNA probe, or 2'-OMe probe or 2'-O-ethyl (2'-OEt) probe or 2'-O-methoxyethyl (MOE) or 2',4'-contrained MOE bicyclic nucleic acid (cMOE BNA) probe or 2',4'-contrained 2'-O-ethyl bicyclic (cEt BNA) probe or S-DNA probe, or the like; directly labeled with any suitable dye, including, for example, ATTO dye, or Cy-dye or Alexa dye, or any fluorophore. An exemplary polyT probe is polyT4 as depicted in FIG. 37.

Method for Identifying Translocations

In another aspect of the invention, the described invention utilizes RNA FISH to provide for identification of at least one of several translocations responsible for oncogenesis. Such information is useful for identifying the origin of the tumor, molecular diagnostics, and appropriate therapy. For example, sarcoma diagnostics benefit from simultaneous monitoring of the expression of multiple molecular markers by RNA FISH. Sarcomas constitute a heterogeneous group of tumors containing more than 100 histological types and subtypes; considerable morphological overlap between the different diagnostic entities contributes to difficulties in classification. Accurate sarcoma subclassification is essential since these different tumor entities require different treatment strategies and have different outcomes. Some sarcomas fall into the diagnostically challenging categories of small blue round cell tumors (SBRCTs) or spindle cell tumors (SCTs). Correct diagnosis is crucial since these morphologically overlapping tumors come from a wider variety of different cell lineages than sarcomas alone. SBRCTs represent a heterogeneous group of tumors with extremely similar histology, sharing undifferentiated small round cells with scant cytoplasm.

Using immunohistochemistry (IHC) and conventional H&E staining, many of these entities can be distinguished. However, combining these markers can streamline the diagnostic process or replace IHC due to its flexibility for including new markers, as well as the associated reduction in costs. Similarly, SCTs also require a series of diagnostic tests for unambiguous diagnosis.

The described invention encompasses the development and use of quantitative multicolor RNA FISH assays that simultaneously monitor mRNAs of multiple diagnostic protein markers, leading to rapid and reliable sarcoma subclassification.

Other aspects of the invention will become apparent to the skilled artisan by the following description of the invention.

EXAMPLES

Clinical Materials and Cell Lines

Sample collection was performed with IRB approval. Thirty-six clinical samples and cell culture aliquots were obtained for miRNA expression profiling by barcoded small RNA sequencing (FIG. 17). Tissue punches from formalin-fixed and paraffin-embedded (FFPE) biopsy specimens of MCC (n=12), BCC (n=4), and NS (n=4) were collected in the Department of Pathology and Molecular Medicine, Kingston General Hospital, Canada. Tissue rolls from FFPE biopsy specimens of MCC (n=2), BCC (n=1), and NS (n=1) were obtained from the Department of Pathology, Fox Chase Cancer Center. Biopsy samples were fixed in 10% neutral buffered formalin for 6-24 h before processing to paraffin using a standard protocol. FFPE specimens were stored at room temperature for an average of 2.5 yr (range: 1-8 yr) prior to nucleic acid extraction. Aliquots of six MCC-derived cell lines were obtained from the Tumor Virology Laboratory, University of Pittsburgh Cancer Institute; MCV status was established using PCR, Southern blot, and immunohistochemical stains for MCV T antigen.

RNA Extraction and Assessment of RNA Integrity.

Total RNA was extracted from FFPE tissue punches and rolls respectively using the RecoverAll total nucleic acid isolation kit (Ambion) or the MasterPure™ Complete DNA and RNA Purification Kit (Epicenter Biotechnologies) according to the manufacturer's guidelines. Total RNA was extracted from cultured cell lines using Trizol® Reagent (Invitrogen) following the manufacturer's instructions. Total RNA concentrations were determined using a Nanodrop spectrophotometer ND-1000 or a BioRad SmartSpec™ Plus Spectrophotometer. Concentrations of recovered total RNA respectively ranged from 0.28-2.44, 0.01-1.80, and 0.81-3.65 μg/μl for Recoverall™, Masterpure™, and Trizol® methods. Low RNA yields for samples NS5a and NS5b likely resulted from difficulty in dissolving paraffin from tissue rolls. RNA integrity was assessed by visual inspection of 28S and 18S rRNA bands following electrophoresis of 1 μg total RNA on an agarose gel stained with ethidium bromide.

Sequencing-Based miRNA Expression Profiling, Quantitation, and Sample Clustering.

Barcoded small RNA sequencing was performed as described; total RNA input was two micrograms per sample except where limited sample (NS5a, NS5b) was available. Barcoded sequence reads were annotated as reported. We excluded one sample (MCC14b) from further analyses due to the low (<20,000) number of miRNA sequence reads. miRNA expression profiles were generated from relative counts of different miRNAs within a sample. Total miRNA concentrations were calculated for each sample by multiplying the ratios of miRNA:calibrator sequence reads by the input calibration marker: total RNA concentrations. Hierarchical clustering was performed as described and miRNAs were presented as precursor clusters according to our ongoing human miRNA reannotation studies. The sequencing data discussed in this publication have been deposited in the NCBI's Gene Expression Omnibus and are accessible through GEO Series accession number GSE34137 at the following link ncbi website.

Microarray-Based miRNA Expression Profiling and Data Analysis.

We profiled miRNA expression in FFPE tissues from six MCC and two NS samples using Agilent human miRNA arrays. Briefly, 100 ng total RNA was dephosphorylated, ligated to pCp-Cy3 using T4 RNA ligase 1, purified, and hybridized to an Agilent Human miRNA Microarray (V2) consisting of eight identical subarrays with probes for 723 human miRNAs. Following scanning with the Agilent microarray scanner (Agilent), images were acquired and analyzed using Agilent feature extraction software version 9.5.3. GeneSpring software was used to normalize and log transform raw data and perform unsupervised hierarchical clustering. Differential expression between MCC and non-MCC groups was assessed by an unpaired t-test. p-values were adjusted for multiplicity using the Benjamini-Hochberg approach to control the false discovery rate (FDR). miRNAs were considered differentially expressed if the FDR was <0.05 and the fold change ≥2.

miRNA real-time PCR.

For comparison with sequencing-derived miRNA concentration estimates, we measured miR-375 expression in total RNA extracted from FFPE tissue punches from 11 MCC and four normal skin samples using TaqMan MicroRNA Assays (Applied Biosystems) according to the manufacturer's guidelines; miR-205 expression was not studied due to a paucity of material. Briefly, miRNAs were reversed transcribed using miRNA-specific stem-loop RT primers (Applied Biosystems). Subsequently, real-time PCR reactions were performed using the Eppendorf Realplex system (Eppendorf). PCR reactions were incubated in a 96-well plate at 95° C. for 10 min, followed by 40 cycles at 95° C. for 15 s, and 60° C. for 1 min. All samples were assayed in triplicate and data were normalized to endogenous RNU6B. Relative miRNA expression levels were calculated using the ΔΔCt method.

Synthesis of ABINA.

ABINA was prepared by refluxing methylisonicotinate (5.5 g, 40.0 mmol, Sigma, catalog no. M52950) and 1,4-diaminobutane (3.5 g, 40 mmol, Sigma, catalog no. D13208) in deionized water (2 ml) for 20 h. Following removal of water and volatiles, the reaction was purified by silica flash column chromatography (gradient, 2:2:1:95 to 32:32:16:20, methanol:acetonitrile:triethylamine:diethylether) to yield ABINA (2.5 g, 32%) as a yellowish oil. ABINA purity was analyzed by thin layer chromatography (TLC, silica gel; methanol/acetonitrile/triethylamine/diethylether (32:32:16:20): Rf (methylisonicotinate)=0.90, Rf (ABINA)= 0.10) and high-pressure liquid chromatography (HPLC, only a single peak was detected).

Tissue Sectioning.

FFPE tissue blocks were first cooled on ice prior to sectioning. 5 or 20 μm tissue sections were cut using a Leica RM2255 Rotary Microtome. For mounting sections on glass slides, sliced tissues were manually unfolded in a room-temperature water bath, then transferred to a 42° C. water bath to allow tissue stretching. To minimizing miRNA diffusion during this step, incubation times at 42° C. were less than 10 s. Tissue sections were immediately mounted on Colorfrost Plus slides (Fisher Scientific, catalog no. 12-550-18), air-dried for 1 h, then incubated in an on oven at 56° C. for 1 h to attach the tissue slice to the slide upon melting of the paraffin.

Synthesis of ATTO-488 and ATTO-532 Tyramides.

ATTO-488-NHS (5 mg, ATTO-TEC GmbH, catalog no. AD 488-35) was dissolved in 500 μl anhydrous N,N-dimethylformamide (DMF, Solulink, catalog no. S-4001-005) to obtain an active ester stock solution A (10 mg/ml). The tyramine-HCl stock solution B was prepared by dissolving 10 mg in 1 ml DMF (10 mg/ml) to which a 1.25-fold equimolar amount of triethylamine (10 μl, Sigma, catalog no. 90335) was added. 500 μL stock solution A was mixed with 84 μl stock solution B and the reaction mixture was left at ambient temperature in the dark for 2 h. After the completion of synthesis, 5.9 μl ethanolamine stock solution C (dissolve 10 μl ethanolamine in 990 μl DMF) was added to the reaction mixture and stirred for 5 min to quench unreacted ATTO-488-NHS ester. The synthesized tyramide conjugate was diluted with 4.4 ml anhydrous dimethyl sulfoxide (DMSO, Sigma, catalog no. D2438) to obtain a final volume of 5 ml.

We prepared ATTO-532 stock solution A (10 mg/ml) by dissolving 5 mg ATTO-532-NHS (ATTO-TEC GmbH, catalog no. AD 532-35) in 500 μl anhydrous DMF. Stock solutions B and C were prepared as above. 500 μl stock solution A was mixed with 76 μl stock solution B, incubated in the dark for 2 h at 25° C., quenched by 5.3 μl ethanolamine stock solution C, and brought to a final 5 ml volume by addition of 4.4 ml anhydrous DMSO. ATTO-tyramide solutions were aliquoted into light-protected 1.5 ml Eppendorf tubes.

miRNA FISH.

miRNA FISH was performed using an extensively modified version of our existing protocol. Briefly, we (1) optimized EDC condensation reaction conditions for crosslinking miRNAs to surrounding proteins (2) eliminated proteinase K treatment for tissue permeabilization, reducing RNA diffusion (3) designed probes with increased linker lengths to increase accessibility to HRP-mediated amplification systems and (4) synthesized fluorescent tyramide:dye derivatives as described, developing an amplification buffer for performing tyramide deposition containing 4-bromoboronic acid to control the oxidation process.

Antisense LNA-modified oligodeoxynucleotide probes targeting miR-205 and miR-375 were designed using mature miRNA sequences from miRBase (http://www.mirbase.org). To minimize rRNA crosshybridization, probe sequences with greater than six consecutive nucleotide matches were avoided and shortened to 14-nt and 15-nt for miR-205 and miR-375, respectively (Supplementary Table 6). Hairpin formation and self-dimerization of probe sequences were predicted using MFold and LNA modifications were placed in regions with no secondary structure or self-hybridization. LNA-probes were synthesized at 1.0 μmol scale on an ABI 3400 DNA synthesizer, deprotected, quantified, and their UV profiles determined as previously published.

miR-205 probe was synthesized with a linker which enabled conjugation of six fluorescein moieties: 5'-GGTG-GAAtgaAgga-(L)$_3$-F-L-F-L-F-L-F-L-F-(F-CPG) (core sequence disclosed as SEQ ID NO: 10); upper case: DNA nucleotides; lower case: LNA modification; L: spacer 18 (GlenResearch, catalog no. 10-1918-02); F: 6-fluorescein serinol (GlenResearch, catalog no. 10-1994-02); F-CPG: 3'-6-fluorescein serinol CPG (GlenResearch, catalog no. 20-2994-10). miR-375 probe was synthesized with a linker which enabled conjugation of six biotin moieties: 5'-AGC-CGaaCGaAcaaA-(L)$_3$-B-L-B-L-B-L-B-L-B-(B-CPG) (core sequence disclosed as SEQ ID NO: 11); B: protected biotinLC serinol (GlenResearch, catalog no. 10-1995-02); B-CPG: 3'-protected biotinLC serinol CPG (GlenResearch, catalog no. 20-2995-10).

Following synthesis, the CPG was transferred to a 1.5 ml screw cap tube and incubated with 1.2 ml of 28-30% aqueous ammonium hydroxide solution (EMD, catalog no. AX1303-6) for 16 h at 55° C. The tube was placed on ice for 5 min, and the supernatant transferred to a 13 ml centrifugation tube. Ten milliliters of 1-butanol was added, vigorously mixed, and the LNA pellet was collected by centrifugation at 13,000 rpm in an SS-34 rotor at 4° C. for 20 min in Sorvall RC5C Plus centrifuge. The supernatant was removed completely, the pellet dried in an Eppendorf Vacufuge concentrator and redissolved in 400 μl water. After deprotection and precipitation, probes were directly used in miRNA FISH approach without further denaturing PAGE gel purification.

Four rRNA antisense 3'-amino-modified LNA probes (Supplementary Table 6) were synthesized using 3'-amino-modifier C7 CPG (500 Å) solid glass support (GlenResearch, catalog no. 20-2957-10) and directly labeled using ATTO-647N-NHS (ATTO-TEC GmbH, catalog no. AD 647N-31) using an established protocol. All directly labeled probes were purified on a denaturing 18% PAGE gel.

Five-micron FFPE tissue sections from BCC and MCC samples were deparaffinized with Histo-Clear II (National Diagnostics, catalog no. HS-202) twice for 6 min, rehydrated with ethanol (95-70-50%) each for 1 min, and rinsed in water. Sections were fixed in 4% paraformaldehyde (PFA, Electron Microscopy Sciences, catalog no. 15710) in TBS (100 mM NaCl, 10 mM Tris-HCl, pH 7.4) for 45 min and washed in TBS for 5 min. Sections were subsequently incubated in 1-methylimidazole/5-ETT buffer (0.1 M 1-methylimidazole (Sigma, catalog no. 336092), 0.1 M 5-ETT, 0.3 M NaCl, pH 8.0) for 10 min, followed by incubation in 500 μl EDC fixative (0.1 M EDC-HCl, Fluka, catalog no. 03450) in 0.1 M 1-methylimidazole/5-ETT buffer) in a humidified chamber at 50° C. for 3 h. Slides were rinsed in 0.2% glycine in TBS for 3 min and in TBS only for 3 min. After washing, sections were incubated in 50 ml freshly prepared acetylation solution (100 mM triethanolamine (Sigma, catalog no. T1377), 52.9 mM (0.5% v/v) acetic anhydride (Acros, catalog no. 149490010) in TBS) at 25° C. for 10 min. Slides were rinsed again as above. Endogenous biotin was sequentially blocked with avidin and biotin solution from the biotin-blocking system (Dako, catalog no. X0590) at 25° C. for 10 min; following each blocking step, slides were rinsed in 50 ml TBS at 25° C. for 3 min.

Sections were pre-hybridized in 500 μl hybridization buffer (50% formamide (Sigma, catalog no. F7503), 1.0 M NaCl, 75 mM Tris (pH 8.5), 1×Denhardt's solution (Applichem, catalog no. A3792), 250 μg/ml baker's yeast tRNA (Sigma, catalog no. R8759-2KU), 500 μg/ml salmon sperm DNA (Applichem, catalog no. A2159), 2.5 mM CHAPS (Sigma, catalog no. C3023), and 0.5% (v/v) Tween 20 (Sigma, catalog no. p 1379)) in a humidified chamber at 25° C. for 1 h. Hybridization buffer was replaced with a hybridization solution, containing (1) antisense miRNA-205 probe conjugated to six fluorescein moieties (2) antisense miRNA-375 probe conjugated to six biotin moieties and (3) four antisense rRNA probes directly labeled with ATTO-647N, each at 25 nM in hybridization buffer, and hybridization proceeded at 55° C. for 16 h.

Following hybridization, slides were washed once in wash buffer 1 (50% (v/v) formamide, 250 mM NaCl, 75 mM Tris-HCl (pH 8.5), and 0.1% (v/v) Tween 20) for 10 min at 25° C., again in wash buffer 1 for 10 min at 33° C., once in wash buffer 2 (50 mM NaCl, 75 mM Tris-HCl (pH 8.5) and 0.1% (v/v) Tween 20) for 5 min at 25° C., and once in TBS-T (TBS with 0.1% (v/v) Tween 20) for 3 min at 25° C. Sections were next incubated in 0.3% hydrogen peroxide (Fisher, catalog no. H325) in TBS-T for 20 min at 25° C., and washed three times in TBS-T at 25° C. The following steps were carried out at 25° C. Slides were immersed in antibody "blocking" solution (5% goat serum (Sigma, catalog no. G9023) in TBS-T) for 30 min. Slides were incubated with 500 μl HRP-conjugated anti-fluorescein antibody diluted 1:250 in blocking solution in a humidified chamber for 1 h. Slides were washed twice in TBS-T for 10 min before incubating each slide in 400 μl tyramide-ATTO-532 solution (tyramide-dye conjugate was diluted 1:50 in PC amplification buffer (50 mM Tris-HCl (pH 8.0), 2 M NaCl, 200 μg/ml 4-bromophenylboronic acid (Aldrich, catalog no. B75956), and 0.015% hydrogen peroxide)) for 30 min in a dark, humidified chamber. Slides were washed three times in TBS-T prior to incubation in 0.3% hydrogen peroxide solution. Each slide was then incubated with 500 μl streptavidin-conjugated to HRP diluted 1:1000 for 1 h in a humidified chamber. Slides were washed twice in TBS-T for 10 min before applying 400 μl tyramide-ATTO-488 solution prepared and incubated as above. Slides were washed three times in TBS-T for 3 min, counterstained with 500 μl DAPI (5 μg/ml in TBS-T, Sigma, catalog no. D8417) in a humidified chamber for 10 min, and washed twice in TBS-T for 3 min. Each slide was mounted with MOWIOL mounting solution (25% (w/v) glycerol, 10% (w/v) MOWIOL (Polysciences Inc., catalog no. 17951) and 0.1 M Tris-HCl (pH 6.8)) and a glass coverslip. Prior to imaging, slides were dried in the dark for 30 min.

Microscopy, Image Processing, and Signal Normalization.

Images in were captured on an Olympus BX50 microscope equipped with a DP70 camera and Olympus DP controller software. For fluorescent imaging, we used the following filter sets: U-MWU2 (Olympus) for DAPI, 41001 HQ (Chroma) for Fluro488, 49004 ET (Chroma) for Cy3, and 49006 ET (Chroma) for Cy5. Images were also captured using the Olympus VS110 Virtual Microscopy System using 20× and 60×UPlanSApo objectives. For fluorescent imaging, we used ATTO-dye combinations and the 86000v2 Sedat Quad filter set (Chroma) including filters for DAPI, Cy2, Cy3, and Cy5 (Supplementary Table 8).

Figure 30:
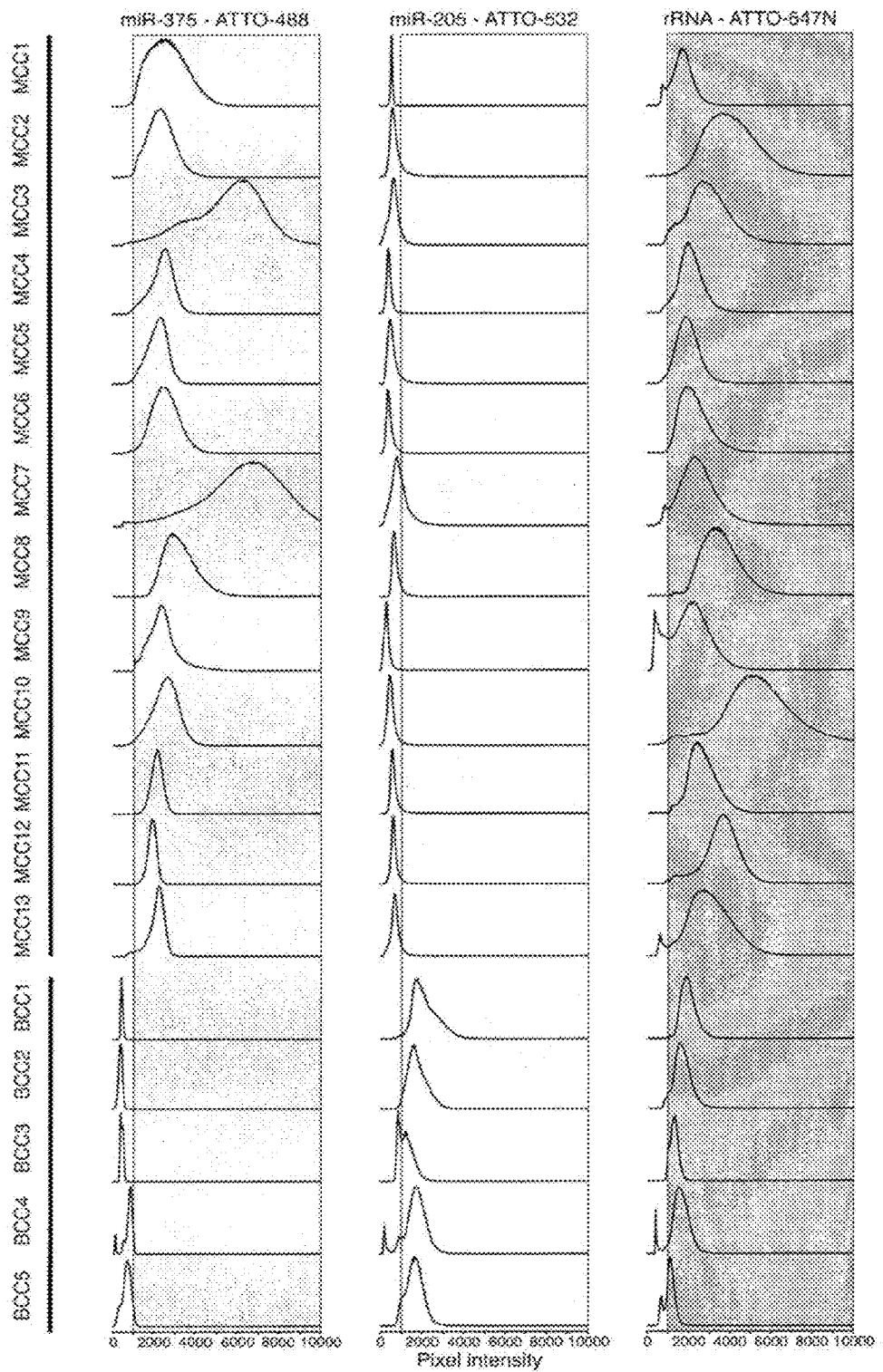
FIG. 30. miRNA signal normalization and establishment of cut-off values for tumor differentiation. Signal intensity histograms for miR-375-ATTO-488, miR-205-ATTO-532, and rRNA-ATTO-647N were used to delineate and differentiate specific RNA and background signals; cut-off values were established on a pilot set of tumors (BCC1 and MCC1) and set at 1,000 pixel intensities for miR-375, miR-205, and rRNA. Corrected miR-375, miR-205, and rRNA pixel intensities (respectively indicated by green, yellow, and red boxes) were multiplied by their corresponding sum of pixels and these values were used to normalize miRNA against reference rRNA signals. Blinded analysis of 16 BCC and MCC tumors was performed using the same cut-off values as above and all tumors were correctly identified based on normalized miR-205 and miR-375 signals; signal intensity histograms from pilot (BCC1 and MCC1) and representative (BCC2-13 and MCC2-5) are presented. The Y-axis is not shown here, instead sum of pixels above a defined threshold as seen in FIG. 25.

Coded tissue sections from 16 BCC and MCC cases were provided by the Department of Pathology and Laboratory Medicine (Queen's University) and miRNA FISH was performed in the Laboratory of RNA Molecular Biology (The Rockefeller University). Under blinded conditions, miR-205, miR-375, and rRNA signal intensities were measured on areas with at least 85% tumor composition. miR-205, miR-375, and rRNA signal intensity histograms were obtained to delineate specific RNA and background signals (FIG. 30). Following background removal, corrected pixel intensities for miR-205, miR-375, and rRNA were multiplied by the corresponding sum of pixels, and these values were subsequently used to normalize miRNA against reference RNA signals. Based on a pilot test of representative tumors (BCC1 and MCC1), a cut-off value of 0.4 was established to differentiate BCC from MCC. Following data collection and interpretation by a blinded tester, sample codes were broken and analyzed.

Immunohistochemistry on EDC-Fixed and Unfixed Tissues.

Ten micron FFPE tissue sections of human breast cancer and 5 μm FFPE tissue sections of mouse embryonic liver, human gastrointestinal stromal tumor (GIST), human Sloan- Kettering ovarian cancer cell line 3 (SKOV3) xenografted to mouse, mouse embryonic brain, and human placenta were mounted on Colorfrost® Plus Microscope Slides (Fisher Scientific catalog no. 12-550-18). Sections were deparaffinized with Histo-Clear II twice for 6 min, rehydrated with ethanol (95-70-50%) each for 1 min, and rinsed in water. Sections were fixed in 4% PFA, in TBS for 45 min and washed in TBS for 5 min. Sections were subsequently processed with and without EDC fixation. For EDC fixation, sections were incubated in 1-methylimidazole/5-ETT buffer for 10 min, followed by incubation in 500 μl EDC fixative in a humidified chamber at 50° C. for 3 h. Slides were rinsed in 0.2% glycine in TBS for 3 min and TBS for 3 min.

Figure 33:
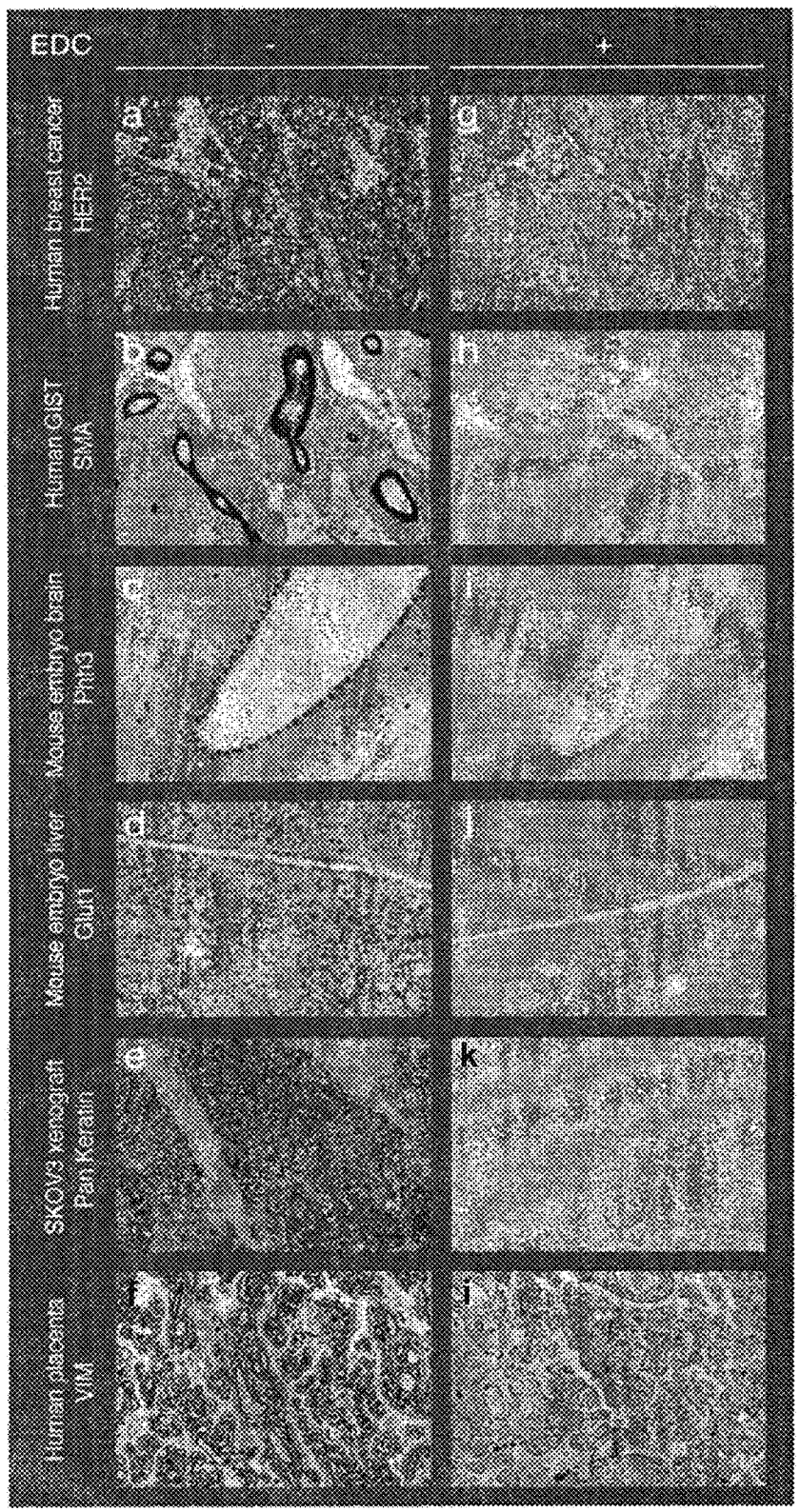
FIG. 33. EDC fixation is incompatible with immunohistochemical staining. To assess the compatibility of EDC-based RNA fixation with immunohistochemistry, we tested multiple EDC-fixed and unfixed tissue sections with commercial grade antibodies. Appropriate signals for human epidermal growth factor receptor 2 (HER2), smooth muscle actin (SMA), phospho-histone-H3 (Phh3), glucose transporter 1 (Glut1), pan-keratin, and vimentin (VIM) were respectively seen in human breast cancer, human gastrointestinal stromal tumor (GIST), mouse embryonic brain, mouse embryonic liver, SKOV3 xenograft, and human placental tissues in unfixed (a-f) but not EDC-fixed (g-l) tissue sections.
Figure 39:
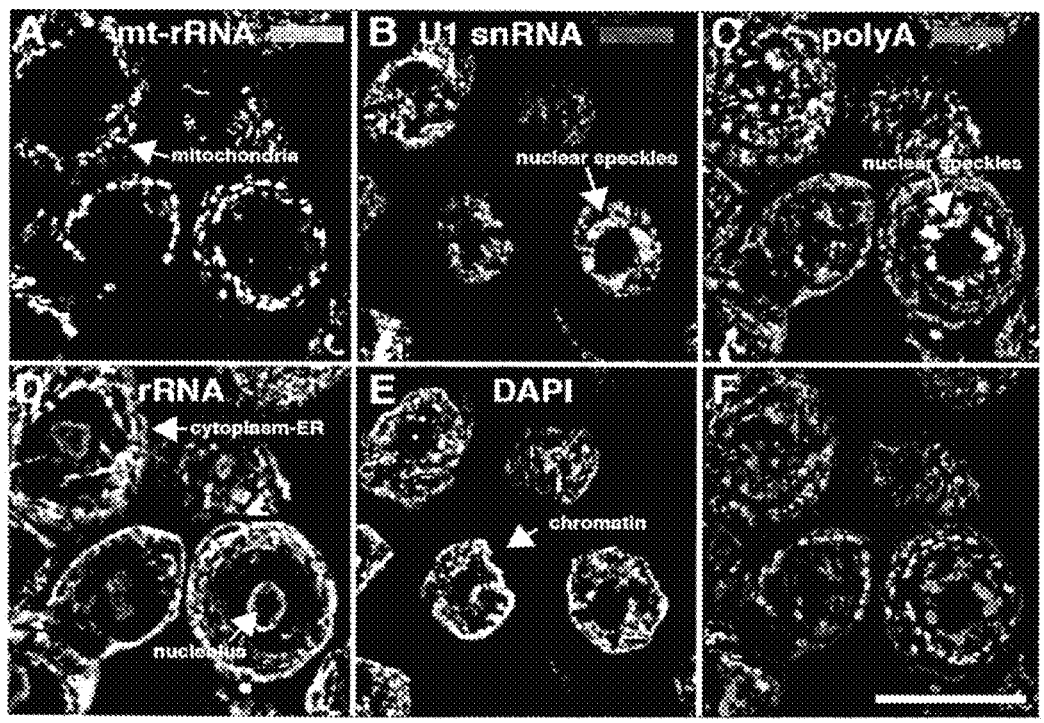
FIG. 39. Multiplexed detection of specific subcellular and variably expressed RNAs using RNA FISH. Probes targeting four RNA species (28S rRNA, U1 snRNA, mitochondrial (mt) rRNA, and polyA tails) with different subcellular locations were assessed in SKBR3 breast cancer cell line using RNA FISH; 28S rRNA is 3-fold more abundant than U1, 10-fold more abundant than mt-RNA, and 4-fold more abundant than polyA tail RNA. Based on the relative abundance of these RNAs, 12, 7, 1, and 5 oligonucleotide probes (containing two fluorophores per probe) were generated to detect mt-rRNA, U1 snRNA, polyA tails, and rRNA respectively. With the exception of the rRNA probe, probes were designed to avoid rRNA complementarity. These probes were subsequently evaluated in FFPE cancer cell lines (SKBR3), using 5 μm tissue sections to mimic a typical surgical pathology specimen and all 5 available fluorescence channels on the scanning microscope. Following simultaneous hybridization of all probes, each RNA was detected in the expected subcellular location; mt-RNA in mitochondria (A), U1 snRNA in nuclear speckles (B), mRNA-polyA tails in nuclei (overlapping with U1 snRNA) and cytoplasm (C), and rRNA in nuclei and cytoplasm (D). Nuclei were also visualized using DAPI stain (E). Overlapping the top 3 channels (mt-rRNA, U1 snRNA, polyA) using artificial RGB coloring shows non-overlapping localization except for the purple appearing nuclear speckles. Probes were hybridized using 25% formamide and 1M NaCl at 50° C. Scale bar, 10 μm, (A-F).

Automated immunohistochemistry was performed using the Discovery XT System (Ventana Medical Systems) and sections were processed in parallel using the same protocol. Briefly, sections were subjected to standard deparaffinization and cell conditioning steps. Samples were blocked for 30 min in 10% normal goat serum, followed by incubation with either rabbit primary antibody of Glucose transporter 1 (Glut1, rabbit, Chemicon, catalog no. AB1340, 0.5 μg/ml), Human epidermal growth factor receptor 2 (HER2, rabbit, Enzo, catalog no. alx-8,0-227, 5 μg/ml), Phospho-Histone-H3 (Phh3, rabbit, Millipore, catalog no. 06-570, 1 μg/ml), or mouse primary antibody of pan Keratin (mouse, Abcam, catalog no. ab8068, 0.5 μg/ml), Smooth muscle actin (SMA, mouse, Sigma, catalog no. A5228, 1 μg/ml), or Vimentin (VIM, mouse, Ventana Medical Systems, catalog no. 790-2917, 2.5 μg/ml) for 4 h. After washing, samples were incubated in buffer containing biotinylated goat anti-rabbit IgG (1:200 dilution, ABC Vectastain kit, Vector labs, catalog no. PK-4001), biotinylated horse anti-mouse IgG (1:200 dilution, MOM Basic kit, Vector labs, catalog no. BMK-2202) at what temp for 1 h. For VIM IHC detection, universal secondary antibody (Ventana Medical Systems, catalog no. 760-4205, pre-diluted) was used. Antigen detection was completed using the DAB-MAP chromogenic detection kit (Ventana Medical Systems, catalog no. 760-124). Images in FIG. 33 were captured using the Olympus VS110 Virtual Microscopy System (Olympus) using the 20× objective (Olympus).

Quantitative Northern Blot Analyses.

To compare the effects of EDC fixation on miRNA diffusion and retention, we prepared FFPE tissue blocks from macaque brain, obtained 10 μm sections, performed miRNA FISH with and without EDC fixation, recovered total RNA from hybridization buffers and treated tissues, and performed quantitative Northern blot analyses for miR-124 as described.[16]

FFPE tissues were prepared by immersing blocks of macaque brain tissue in 40 ml of 4% PFA at 4° C. for 24 h prior to standard paraffin embedding. Three hundred milligrams of 10 μm sections of FFPE tissue was transferred into a SigmaPrep™ Spin Column (Sigma, catalog no. SC1000) to facilitate removal of liquid by centrifugation. Tissue sections were repeatedly incubated in 600 μl Histo-Clear II until the flow through was clear. Tissues were rehydrated by successive incubation in 100%, 95%, 70%, and 50% ethanol, each for 1 min, prior to 3 washes in water. Tissues were incubated in 600 μl of 4% PFA for 45 min at 25° C. and washed briefly in 600 μl of TBS. Tissues were subsequently incubated in either 600 μl of 1×TBS for 3 h at 25° C. or 600 μl of 1-methylimidazole solution for 3 min prior to fixation in 600 μl of EDC fixative solution for 3 h at 50° C., and consecutive washes, twice each, in 0.2% glycine in TBS for 3 min at 25° C., and TBS for 3 min at 25° C. EDC-fixed and unfixed tissues were subsequently incubated in modified hybridization buffer (50% formamide, 1.0 M NaCl, 75 mM Tris (pH 8.5), 2.5 mM CHAPS, and 0.5% (v/v) Tween 20, omitting Denhardt's solution, Baker's yeast tRNA, and salmon sperm DNA to facilitate miRNA recovery) for 16 h at 50° C. Hybridization solutions were collected (ca. 500 μl), diluted with 250 μl of 3 M NaCl, 1.8 ml of Millipore water and 5 μl of glycogen (20 μg/μl; Thermo Scientific, catalog no. R0551) and RNAs were precipitated upon addition of 7.5 ml 100% EtOH; RNA pellets were dissolved in 20 μl water. Residual tissues were incubated in 700 μl Proteinase K solution (100 μg/μl; 0.2 M Tris (pH 7.4), 0.3 M NaCl, 2% SDS (w/v), and 25 mM EDTA) for 5 h at 50° C. Total RNA was extracted from liquids containing protease-digested tissues using standard phenol-chloroform extraction and ethanol precipitation (adding 0.5 μl of glycogen (20 μg/μl) as carrier) protocols. Each pellet was resuspended in 20 μl $H_2O$ and total RNA concentration was measured using a BioRad SmartSpec™ Plus Spectrophotometer.

Statistical Analyses.

Statistical analyses were conducted using R language (www.R-project.org) and contributed packages. We tested normality assumptions using the Kolmogorov-Smirnov (KS) test. All p-values are two-tailed unless otherwise specified.

We assessed differences in total miRNA concentrations following different RNA extraction methods using Kruskal Wallis (KW) rank sum and ANOVA tests; due to the similarity of results only ANOVA test results are presented. Normality assumption was not rejected (KS p=0.168 and 0.285). When comparing data between BCC, MCC, and NS groups in sequencing run 1, pairwise differences were assessed using Tukey's 'Honest Significant Difference' method; adjusted p values are referred to as $p_{adj}$.

Differences in miR-205 and miR-375 concentrations and miR-375 real-time PCR values between MCC and non-MCC groups were assessed using ANOVA after $log_2$ transformation. In this scale, the normality assumption was not rejected (p=0.197, 0.219, and 0.318 respectively). Correlations between miR-205 and miR-375 concentrations were assessed with Pearson correlation for log-2 transformed values and Spearman correlation.

Discriminant analyses between MCC and non-MCC were performed using linear discriminant analysis (lda package from R). Sequencing run one was used as the training set to construct a classifier and sequencing run two was used as the testing set to evaluate the performance of the classifier within an independent sample set. Identical results were obtained using the nearest shrunken centroid (pamr package) and support vector machine (svm). The addition of other miRNAs did not improve the performance of the classifier.

Differences in miR-205 and miR-375 fluorescence intensities between BCC and MCC groups were assessed using ANOVA models after log 2 transformation. In this scale, the normality assumption was not rejected (p=0.145, 0.783, and 0.318 respectively).

By this invention, a quantitative multicolor RNA FISH method, independent of signal amplification (in contrast to IHC and DNA FISH), for use on formaldehyde-fixed paraffin-embedded (FFPE) cancer and sarcoma tissue sections is provided.

This method addresses the issues of (1) special fixation approaches to retain RNA using EDC (2) use of multiple short fluorescent oligonucleotide probes to bypass enzyme-based signal amplification and tissue permeabilization (3) probe design avoiding cross-hybridization to ribosomal RNA (rRNA) and other highly abundant RNAs including non-coding RNAs such as mt-rRNA, U1, U2 and U6 small nuclear RNAs, hy3, 7SL and 7SK small cytoplasmic RNAs and highly abundant mt-mRNAs (4) signal normalization through concomitant use of rRNA, polyA, U1 snRNA, U2 snRNA, U6 snRNA, 7SL scRNA, hy3 scRNA, 7SK scRNA and U3 snoRNA probes.

Monitoring ratios of non-coding RNAs (including rRNA, polyA, mt-rRNA, U1 snRNA, U2 snRNA, U6 snRNA, 7SL scRNA, hy3 scRNA, 7SK scRNA and U3 snoRNA or other highly abundant non-coding RNAs) is used to generate molecular signatures with several molecular diagnostic uses including (1) assessing and/or standardizing RNA quality and retention in cells and tissues prior to molecular testing (2) differentiating cell types within solid or liquid specimens and identifying RNAs associated with specific subcellular compartments (3) assessing sensitivity and specificity of mRNA probes (4) differentiating diseased and normal cells within solid or liquid specimens (5) determining prognosis or disease progression in clinical samples (6) predicting therapeutic response in clinical samples (7) monitoring therapy in clinical samples and (8) disease screening in clinical samples.

Because transcription is a marker of cellular activity, RNA signatures are expected to have widespread clinical utility, particularly for molecular diagnostic testing of cancer, metabolic, and degenerative disease samples; specific examples include rapid identification of pre-malignant and malignant cells in cytology specimens, tumor classification and/or subclassfication, identification of markers (altered RNA signatures, RNA mislocalization to ectopic subcellular compartments) with clinical significance within tumors that are not readily detectable using immunohistochemistry or other molecular diagnostic techniques, and loss of signal (e.g. mitochondrial RNA) in neurodegenerative diseases. RNA signature detection is expected to be used in conjunction with mRNA FISH.

Use of paraffin-embedded cell pellets over paraffin-embedded tissues in RNA FISH experiments have several advantages: 1. Homogenous cell lines can be easily RNA sequenced and then chosen for RNA FISH experiment based on expression data from RNA sequencing. 2. Sections of multiple different paraffin-embedded tumor cell line pellets (positive or negative for desired mRNA target) can be mounted on the same slide, processed and scanned in parallel. 3. Fluorescence intensities for desired target mRNAs can be quantified in positive and negative cell line and compared with RNA sequencing data, which enables specificity determination of the probes. Such specific probes can be subsequently used for accurate gene expression quantification in precious tissue samples. 4. Acquiring cell lines is less time consuming and more cost effective than acquiring tissues. More importantly, researchers don't depend on precious clinical samples, which in many cases are difficult to achieve.

The following examples are set forth to illustrate the present invention, and are not to be construed as limiting thereof.

Example 1

To assess miRNA expression differences between tumors, total RNA was extracted from 36 archived clinical materials and fresh cell lines from patients with Merkel cell carcinoma (MCC), basal cell carcinoma (BCC), and normal skin (NS) (FIG. 16).

Figure 3A:
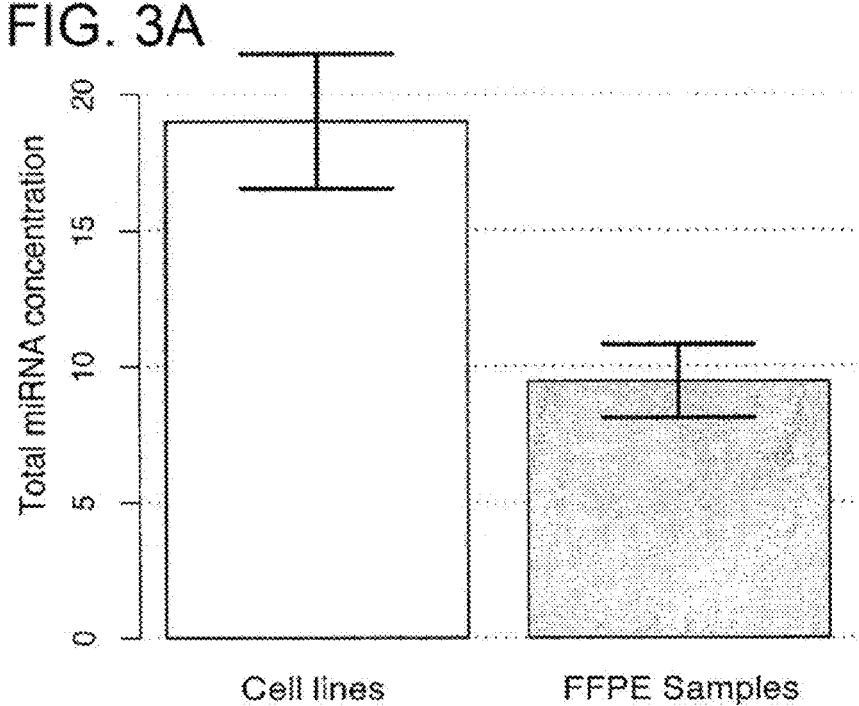
FIG. 3: Total miRNA concentrations in clinical samples. (a) Mean total miRNA concentrations (fmol/μm total RNA) were higher for Trizol-extracted cell lines than for Recover-All- or Masterpure-extracted FFPE materials (ANOVA p<0.001, $N_u$=8, $N_{FFPE}$=27). Higher total miRNA concentrations were seen when rRNA sequence reads, indicating rRNA recovery, were lower (Pearson correlation −0.89, p=<0.001). (b) Significant differences in mean total miRNA concentrations were seen between groups (ANOVA p<0.001, $N_{MCC}$=12, $N_{BCC}$=4, $N_{NS}$=4); mean total miRNA concentrations were respectively 4.43 ($P_{adj}$=0.004) and 5.35 ($p_{adj}$=0.005) fmol/μg total RNA higher in BCC than in MCC or NS whereas no significant difference was seen between MCC and NS ($p_{adj}$=0.72). Error bars indicate the standard error of the mean.
Figure 3B:
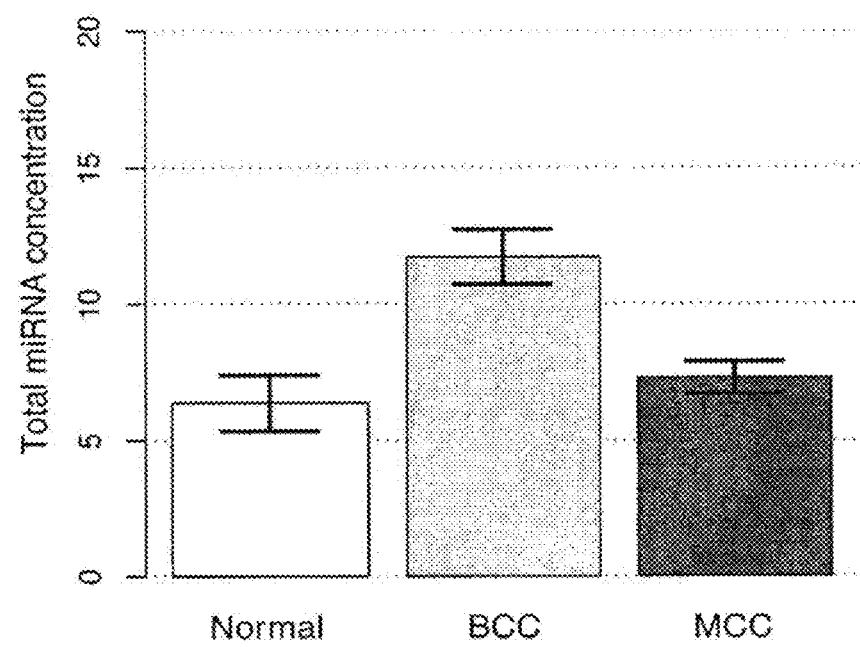
Figure 18:
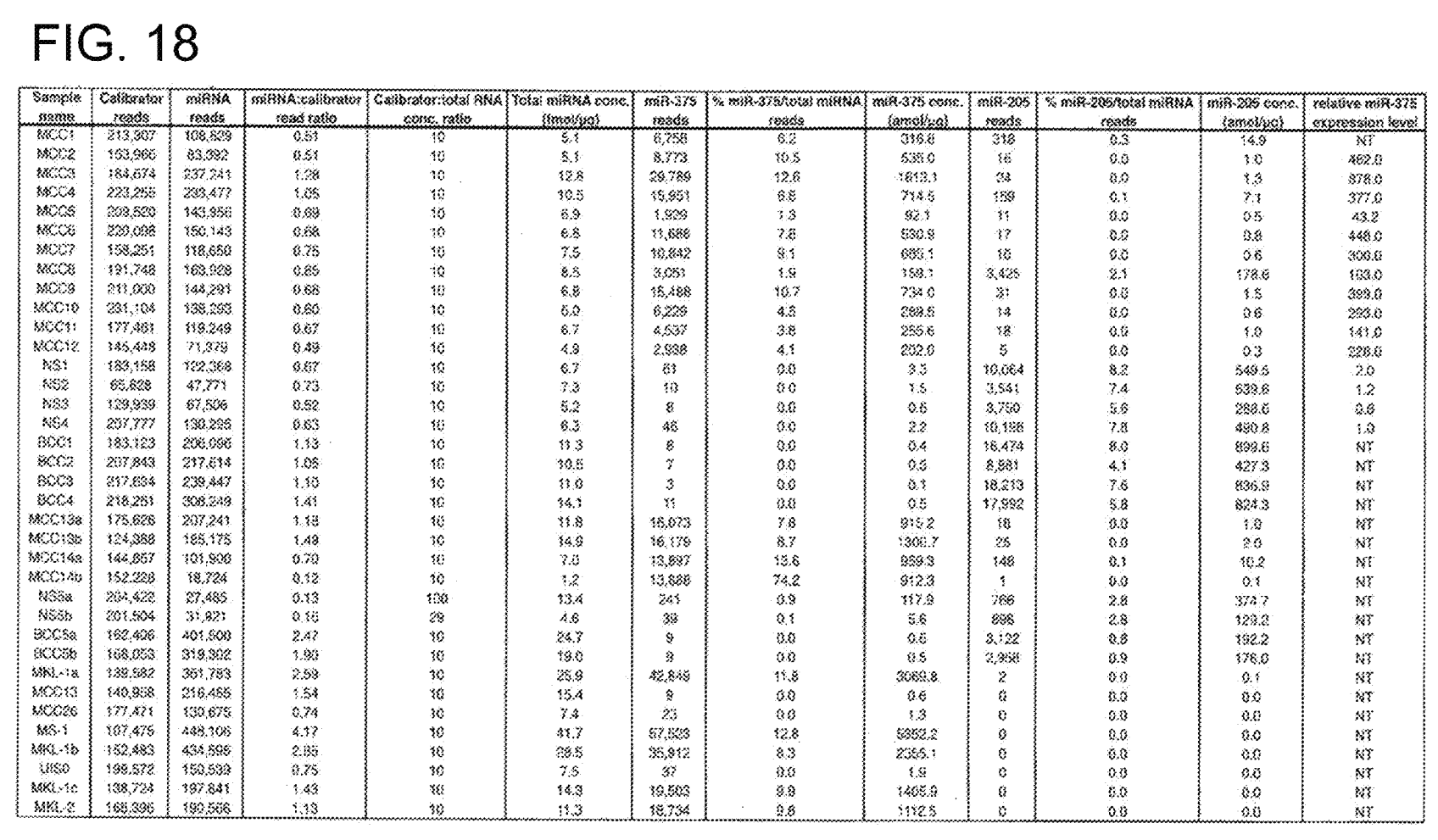

We subsequently profiled and quantitated miRNAs in all samples using barcoded small RNA sequencing. Sequence reads were annotated by RNA category (FIG. 17). Total miRNA concentrations were calculated for all samples using sequence read and RNA input ratios and averaged 11.6 (range: 4.6-41.7) fmol/μg (FIG. 18). Higher total miRNA concentrations were seen in Trizol-extracted fresh cell lines (CL) compared to Masterpure- or RecoverAll-extracted FFPE samples (FIG. 4), consistent with reported differences arising from sample processing and/or RNA extraction method. To minimize these differences, we compared concentrations in RecoverAll-extracted FFPE samples from sequencing run one (hereafter termed the training set). Total miRNA concentrations were significantly higher in BCC than in MCC or NS whereas no significant difference was seen between MCC and NS (FIG. 3). Increased total miRNA concentration in certain tumors, such as BCC, may reflect an increased rate of miRNA biogenesis and/or processing or decreased rate of degradation.

Hierarchical clustering of all miRNA expression profiles, using relative counts of miRNA sequence reads, indicated 2 major groups corresponding to MCC (comprising MCC tumors and MCV-infected cell lines) and non-MCC (comprising BCC, NS, and MCV-uninfected cell lines) groups. To minimize sample processing and extraction differences, we clustered training set samples and saw the same grouping. Interestingly, some MCC-derived cell lines (MKL, MSI) clustered in the MCC group whereas others (MCC13, MCC26, U1S0) clustered in the non-MCC group, mirroring their MCV status. When compared with miRNA profiles from approx. 1,000 clinical samples in our database, MKL and MSI clustered with MCC tissues whereas MCC13 clustered with liposarcoma cell lines and MCC26 and U1 S0 clustered with breast cancer cell lines. These data may accurately reflect the origin of these cell lines, however it is possible that non-MCC group cell lines are MCC variants with differing gene expression and oncogenic pathways.

Discriminant analysis identified tumor-specific miRNA biomarkers. MCC and non-MCC groups were accurately differentiated based on miR-375 and -205 expression, with no errors in the training set (sequence run one) and one error in the testing set (sequence run two). Significant differences in miR-375 and -205 concentrations were seen between MCC and non-MCC groups for all samples (ANOVA $N_{MCC\,group}=20$, $N_{non\text{-}MCC\,group}=15$); miR-375 concentrations were 592-fold higher in MCC than non-MCC ($p=1.5\times10^{-15}$) and miR-205 concentrations were 81-fold higher in non-MCC than MCC ($p=3.0\times10^{-4}$) (FIG. 4). Significant differences were again seen when examining testing set samples (ANOVA $p=7.0\times10^{-8}$, $N_{MCC}=12$, $N_{non\text{-}MCC}=8$); miR-375 concentrations were 577-fold higher in the MCC than the non-MCC group ($p=1.8\times10^{-11}$) whereas miR-205 concentrations were 308-fold higher in the non-MCC than the MCC group ($p=7.0\times10^{8}$)

We confirmed these grouping and expression differences in a subset of six MCC and two NS samples using miRNA microarray and real-time RT-PCR analyses. Principal component analysis similarly indicated MCC and non-MCC groups. Similar differences in miRNA expression between groups were seen as above; miR-375 was 310-fold higher in MCC than NS ($p=0.006$) and miR-205 was 505-fold higher in NS than MCC ($p=0.003$). miR-375 real-time PCR expression levels were also significantly higher in MCC tissues compared to NS (ANOVA $p=1.8\times10^{-8}$, $N_{MCC}=11$, $N_{NS}=4$, FCH=233.5); miR-205 expression was not assessed due to a paucity of clinical material. Where tested, sequencing-derived miR-375 concentrations and real-time PCR measurements were strongly correlated (Spearman correlation 0.94 ($p<2.2\times10^{-16}$); Pearson correlation of log 2-transformed variables 0.99 ($p=3.3\times10^{-13}$)).

After identifying a distinct, inverse relationship between miR-375 and -205 expression that differentiated MCC and BCC, we established a multicolor miRNA FISH protocol suitable for FFPE tissue sections. To achieve this goal, we optimized RNA fixation, probe design, and signal detection and amplification steps.

Figure 5A:
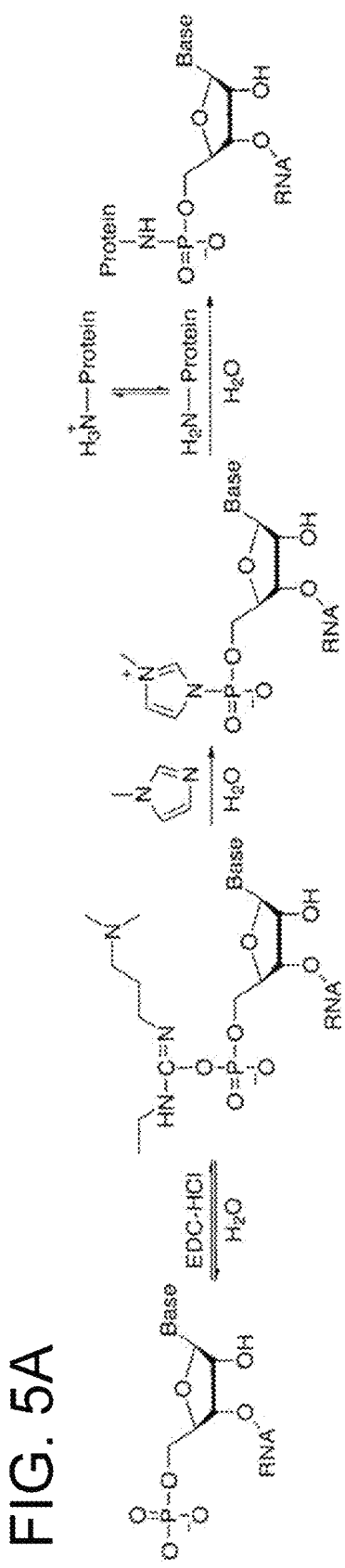
FIG. 5: EDC crosslinking of 5' p-RNA and protein in 1-methylimidazole. Mechanism of EDC crosslinking of 5' phosphorylated RNA and protein in 1-methylimidazole. (a) EDC activation of the 5'-phosphate group is the first step of the crosslinking reaction. Due to the short half-life of EDC-activated miRNA in water, 1-methylimidazole was used to form a more stable reaction intermediate, reacting with an amino group on the peptide to form a stable phosphoamide bond; the formation of EDC-activated miRNA and 1-methylimidazole-miRNA intermediates were confirmed by HPLC (data not shown). When 1-methylimidazole was replaced with triethylamine, MOPS, or HEPES buffers (lacking phosphate and primary amines), the crosslinking reaction time increased considerably (>30-fold) indicating the necessity of 1-methylimidazole for stabilizing EDC crosslinking. The EDC crosslinking reaction is affected by two equilibria. The first equilibrium is affected by hydrolysis that can be reduced by reacting with heterocyclic derivatives. The second equilibrium between protonated and unprotonated amines also affects the EDC crosslinking reaction; it would be preferable to carry out the reaction at basic pH, given the pKa of 10.5 for the Lys side chain, however hydroxide ions begin to compete for the nucleophilic attack of the EDC-5'-p-RNA intermediate under these conditions. Therefore, the reaction was performed at pH 8 to balance the effects of side reactions of both equilibria for optimal EDC crosslinking (b) Addition of 5-ETT decreased the reaction time for EDC crosslinking through competing intermediate formation.
Figure 5B:
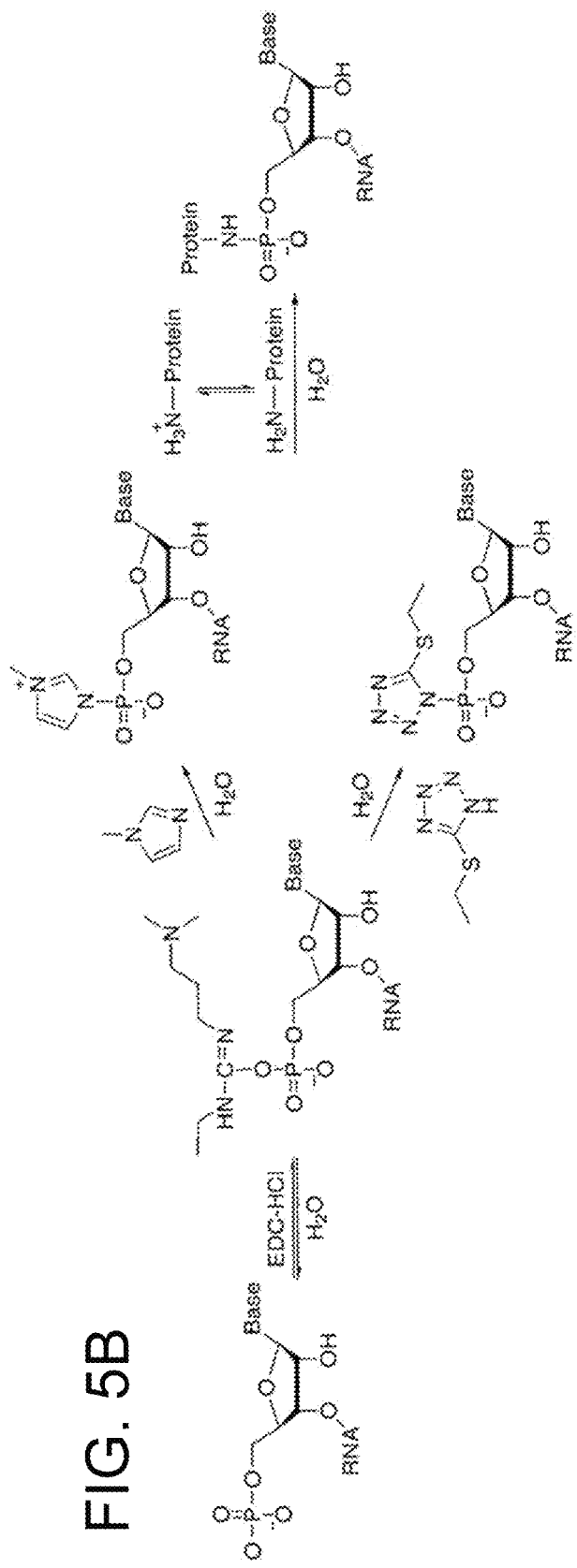
Figure 6A:
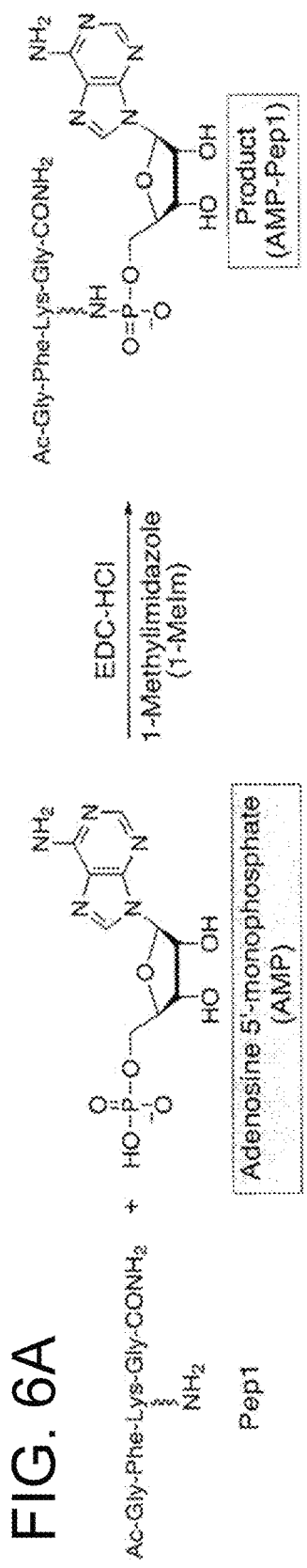
FIG. 6(a) discloses the core sequence of "Ac-Gly-Phe-Lys-Gly-CONH2" as SEQ ID NO: 1. (b) HPLC traces recording UV 260 nm absorbance of reaction products during a 10 h time course of a model condensation reaction at pH 8. Peaks corresponding to AMP (highlighted blue), Pep1, and crosslinking product Amp-Pep1 (highlighted red), 1-Methylimidazole (1-MeIm) are marked. Reaction times and product yields are indicated. (c) The highest product yield was achieved at pH 8. AMP was reacted with an excess of Acetyl-N-Gly-Phe-Lys-Gly-C—$NH_2$ (SEQ ID NO: 1), with only the Lys residue being crosslinked.
Figure 6B:
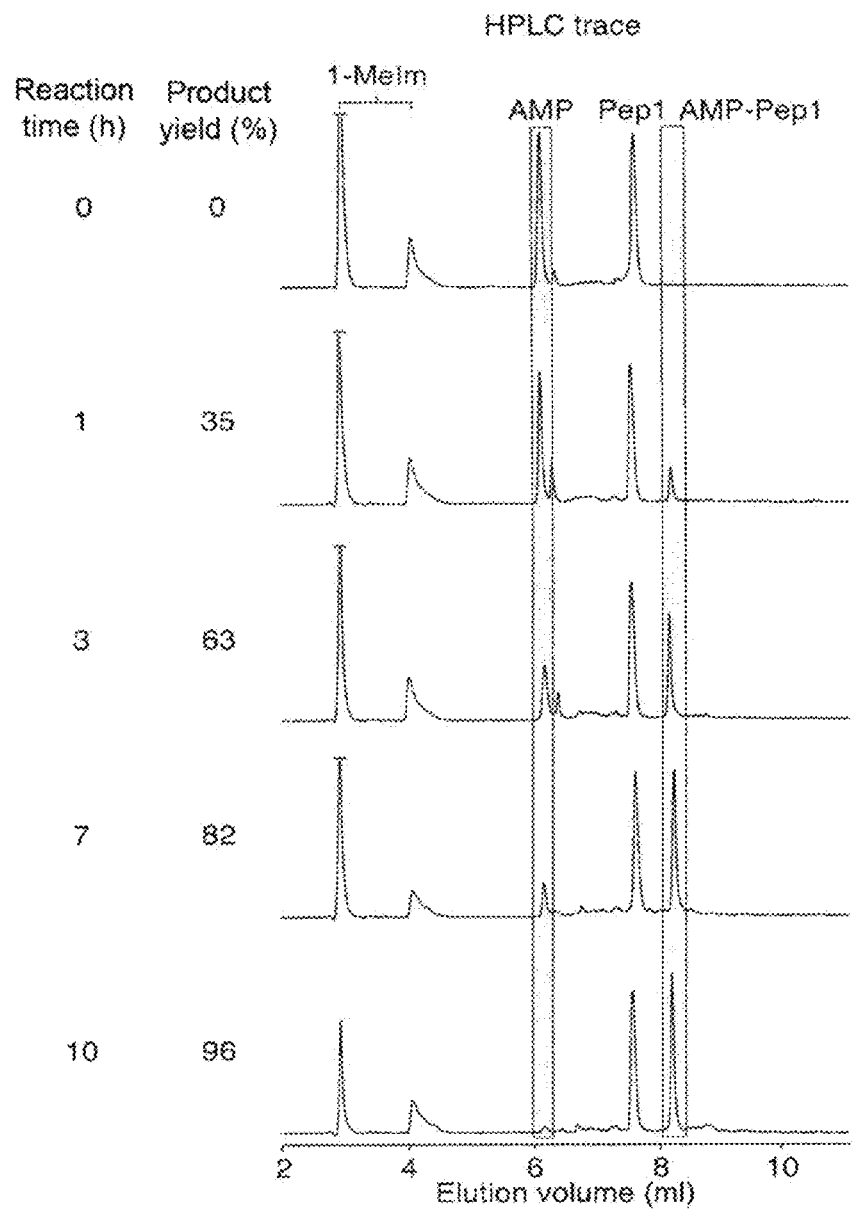
FIG. 6: EDC-mediated condensation using adenosine 5' monophosphate and a lysine-reactive peptide. (a) The reaction between AMP and peptide Pep1 (Phe was included in the peptide to allow for monitoring of the peptide by UV) at 50° C., yielded a stable phosphoramidate product AMP-Pep1.
Figure 6C:
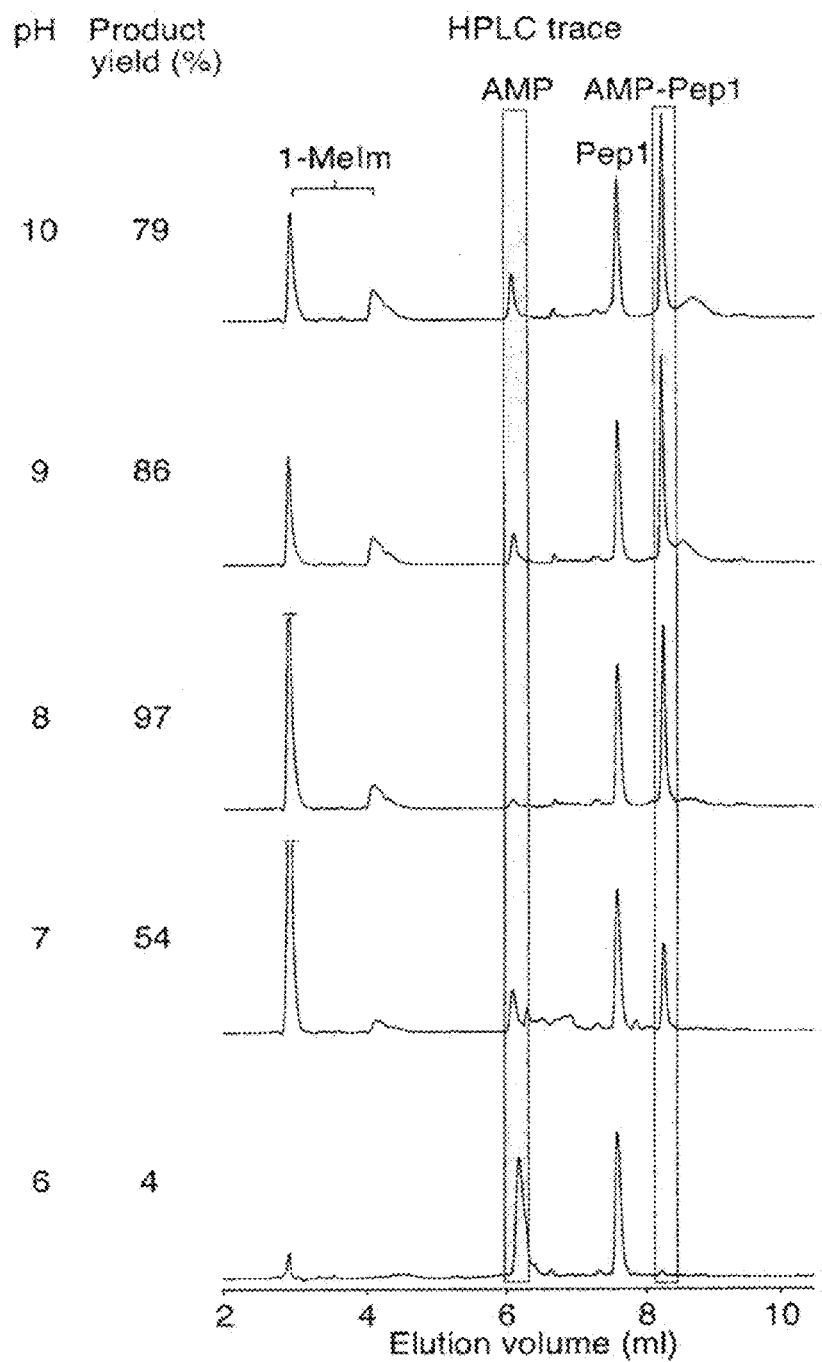
Figure 7:
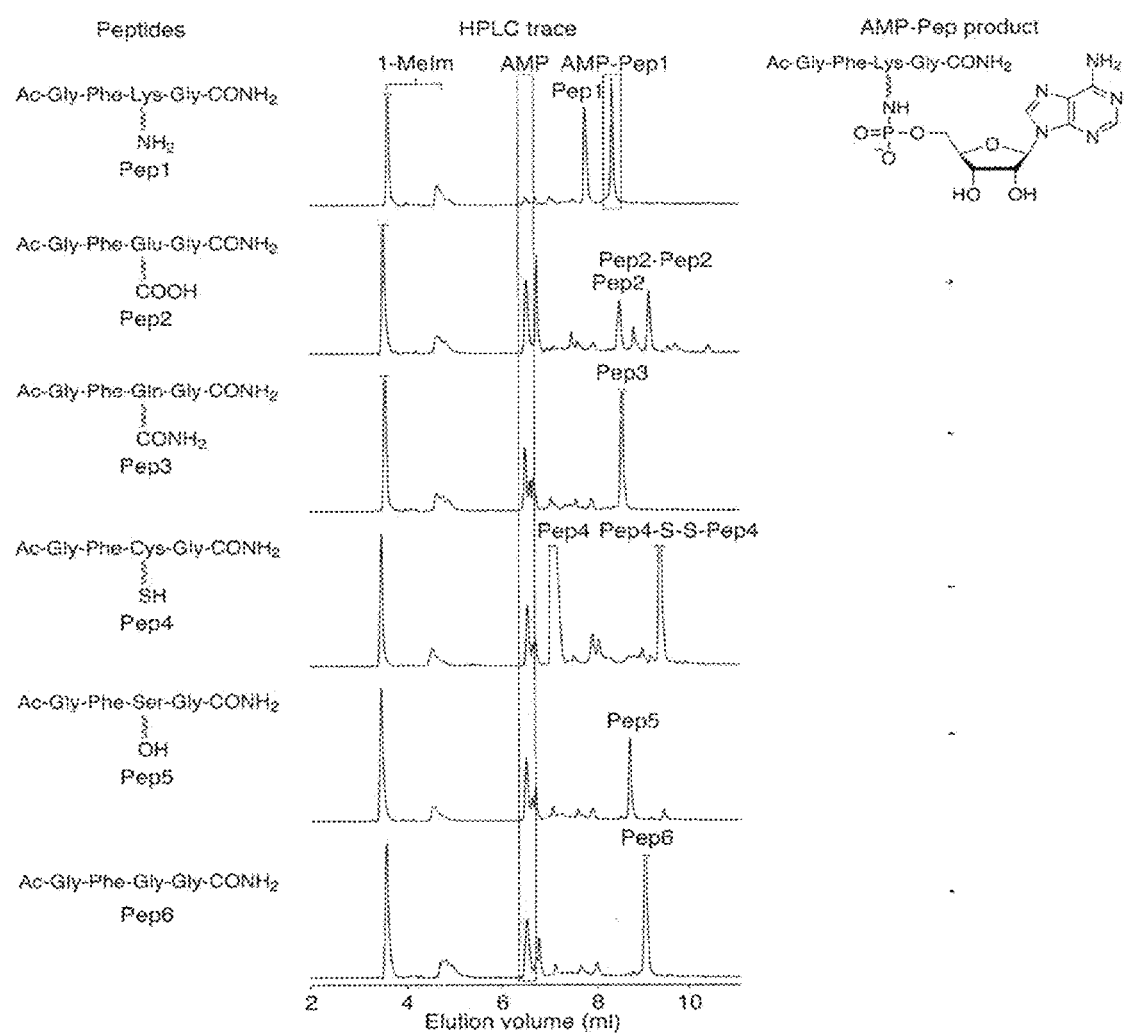
FIG. 7: Specificity of EDC-mediated condensation reaction. When six different peptides of similar sequence, Acetyl-N-Gly-Phe-X-Gly-C—$NH_2$ (X=Lys, Glu, Gln, Cys, Ser, or Gly) (SEQ ID NO: 2), were incubated with AMP and EDC-HCl for 10 h at 50° C., only peptide Pep1 with Lys residue was detected to form phosphoramidate product indicating that EDC crosslinking is primary amino-group-specific. Peaks corresponding to AMP (highlighted blue), Pep1, Pep2, Pep3, Pep4, Pep5, Pep6, crosslinking product Amp-Pep1 (highlighted red) product, 1-Methylimidazole (1-MeIm) and non-phosphoramidate product Pep2-Pep2 (an anhydride dimer, see also FIG. 11, below) and Pep4-S-S-Pep4 (a dimer formed by disulfide bridge) are marked.

Suboptimal RNA fixation leading to RNA loss by diffusion, rather than RNA degradation, is the primary problem in optimizing RNA ISH. To resolve this problem, we previously reported the use of EDC (1-ethyl-3-(3-dimethylaminopropyl) carbodiimide), a water-soluble condensation reagent which promotes phosphoramide bond formation between the miRNA 5' phosphate end and aliphatic amines from amino acid side chains of surrounding proteins (FIG. 5). We further investigated the EDC condensation reaction in vitro by reacting 5' adenosine monophosphate (5' AMP) and modified peptides and found that the phosphate moiety predominantly reacted with the primary amine of lysine (FIGS. 6 and 7). We also observed a pH-dependent hydrolysis side-reaction of EDC-miRNA intermediate that reduced the crosslinking between protein and miRNA (FIG. 6). To diminish this side-reaction, we prepared ABINA (FIG. 8), a highly soluble model compound with a pKa similar to the lysine side chain amine. We subsequently optimized EDC-mediated condensation reaction conditions by reacting ABINA with AMP (FIG. 9) using different EDC-derivatives (FIG. 19) and various heterocyclic compounds (FIG. 20) that form stable reaction intermediates and, therefore, decrease hydrolysis. The reaction time was reduced to 1 h at 50° C. using EDC-methiodide (MeI) and 5-ethylthio-1H-tetrazole (5-ETT) to decrease hydrolysis. In addition, the use of two heterocyclic derivatives (1-methylimidazole and 5-ETT) resulted in competing intermediate formation, enhancing nucleophilic attack of the aliphatic amine and faster crosslinking (FIG. 5b). Despite the short reaction time, these reaction conditions resulted in over crosslinking, hindering hapten-antibody-HRP binding and weakening signal amplification. Therefore, we selected EDC-HCl and 5-ETT in 1-methylimidazole buffer, reducing the reaction time to 3 h at 50° C.

Figure 10B:
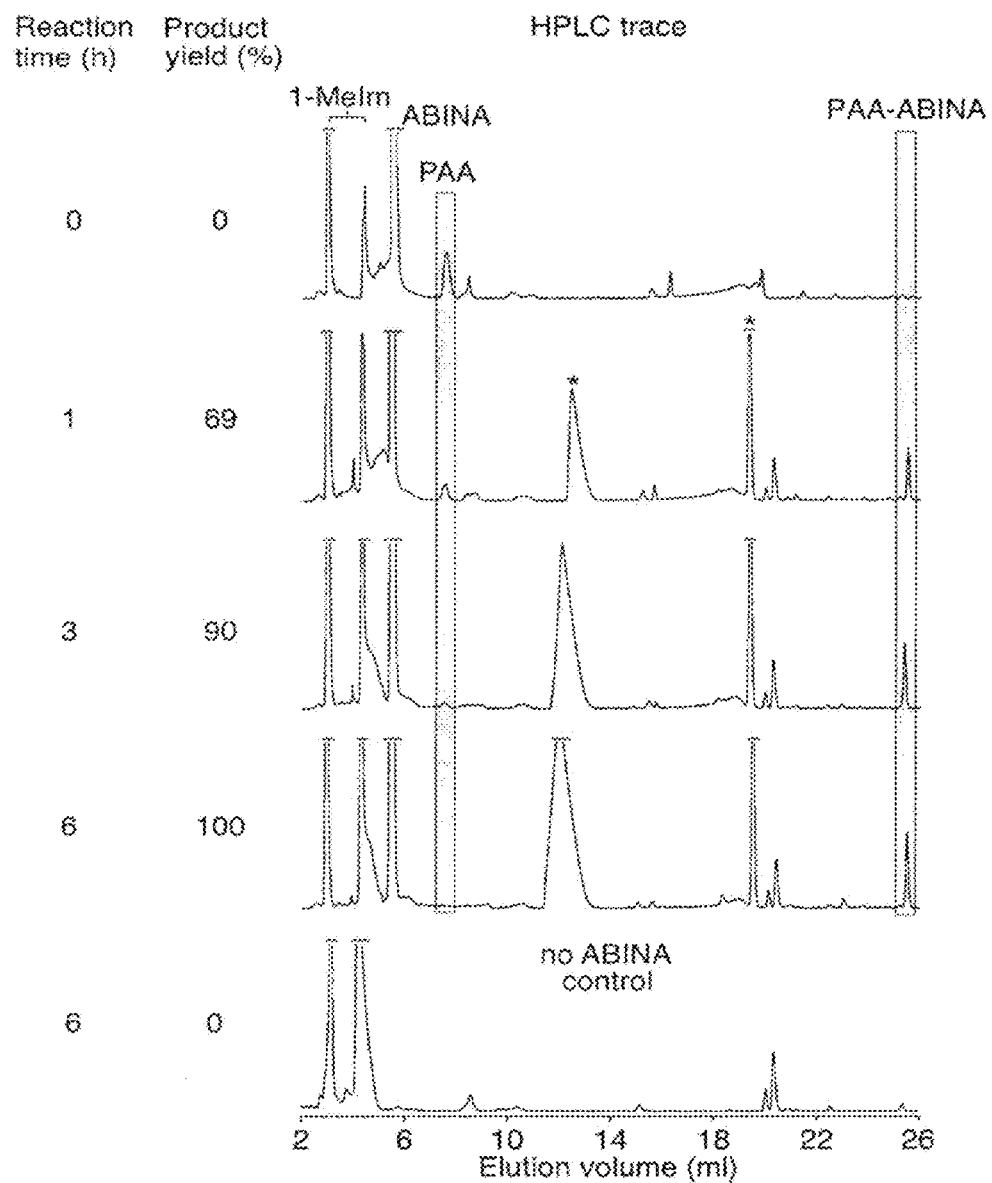
FIG. 10: EDC-based condensation of ABINA and 3-pyridylacetic acid indicating EDC-based crosslinking between proteins. (a) The reaction between 3-pyridylacetic acid (PAA) and ABINA at 50° C. yielded a stable amide product PAA-ABINA. (b) HPLC traces recording UV 260 nm absorbance of reaction products during a 6 h time course of a model condensation reaction at pH 8. EDC-MeI was used in place of EDC-HCl, resulting in a substantial decrease in reaction time. Peaks corresponding to synthesized amine ABINA, PAA (highlighted blue) and crosslinking product PAA-ABINA (highlighted red), 1-Methylimidazole (1-MeIm) and side products (*) are marked. Reaction times and product yields are indicated. When the condensation reaction proceeded without ABINA, anhydride product formation was observed.
Figure 11:
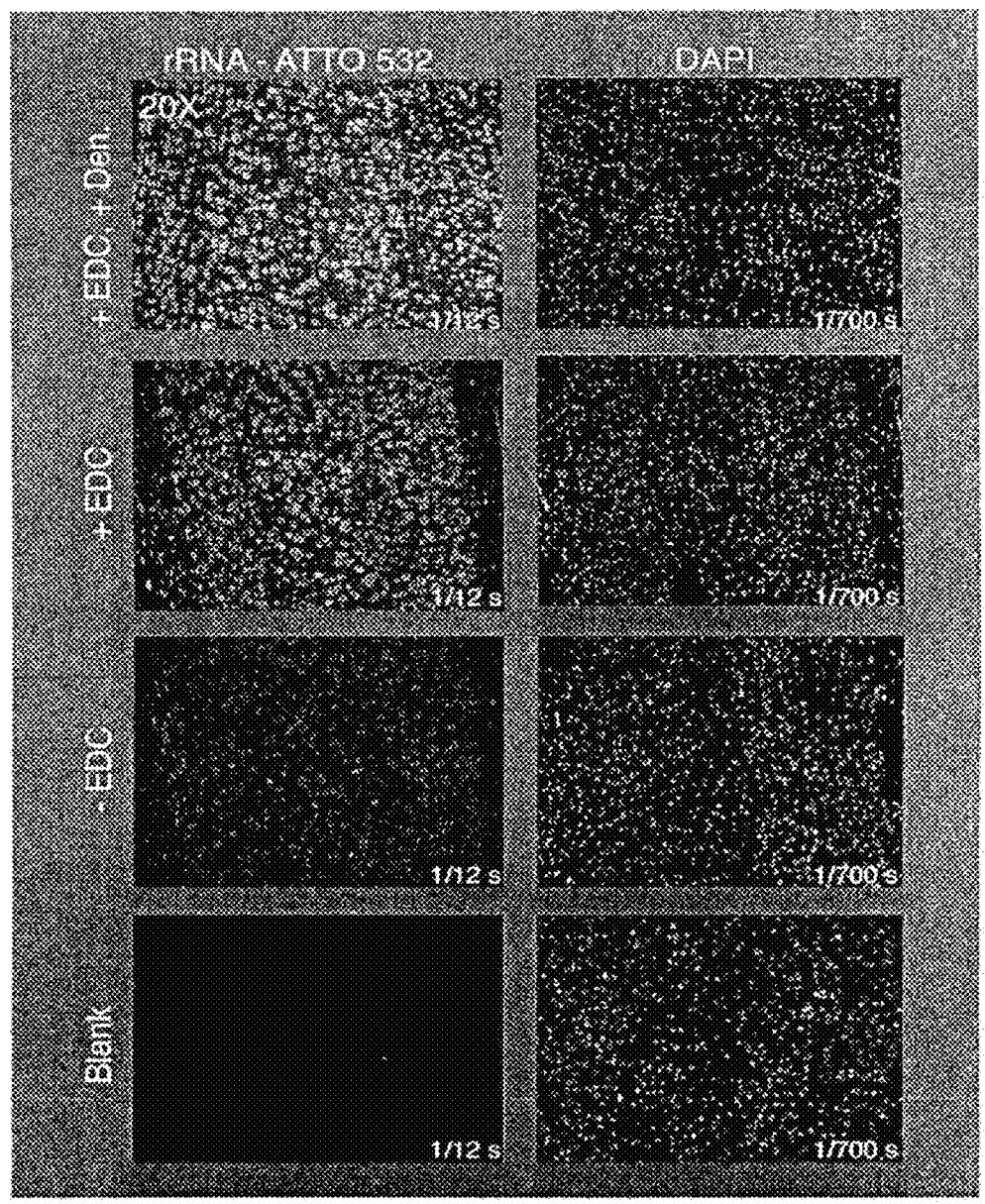
FIG. 11: Retention of rRNA through additive effects of EDC and Denhardt's solution. Following EDC fixation, long RNAs, such as rRNA, were retained due to protein networking by EDC crosslinking as evidenced by increased signal intensity (see corresponding panel +EDC/rRNA-ATTO532). Denhardt's solution during EDC fixation further augmented rRNA signal intensity due to increased EDC permeabilization. rRNA probes were directly conjugated with ATTO 532.

We also noted that EDC forms carboxylic acid amide bonds that network proteins (FIG. 10), potentially reducing RNA diffusion. We, therefore, monitored retention of RNAs lacking 5' phosphates but possessing 5' hydroxyl and 2',3' cyclic phosphate termini formed by partial hydrolysis during paraffin-embedding. Following EDC fixation, we observed increased retention of long RNAs, such as rRNA; the addition of Denhardt's solution during EDC fixation further augmented rRNA signal intensity, presumably due to increased membrane permeabilization for positively charged EDC molecules (FIG. 11).

Figure 12C:
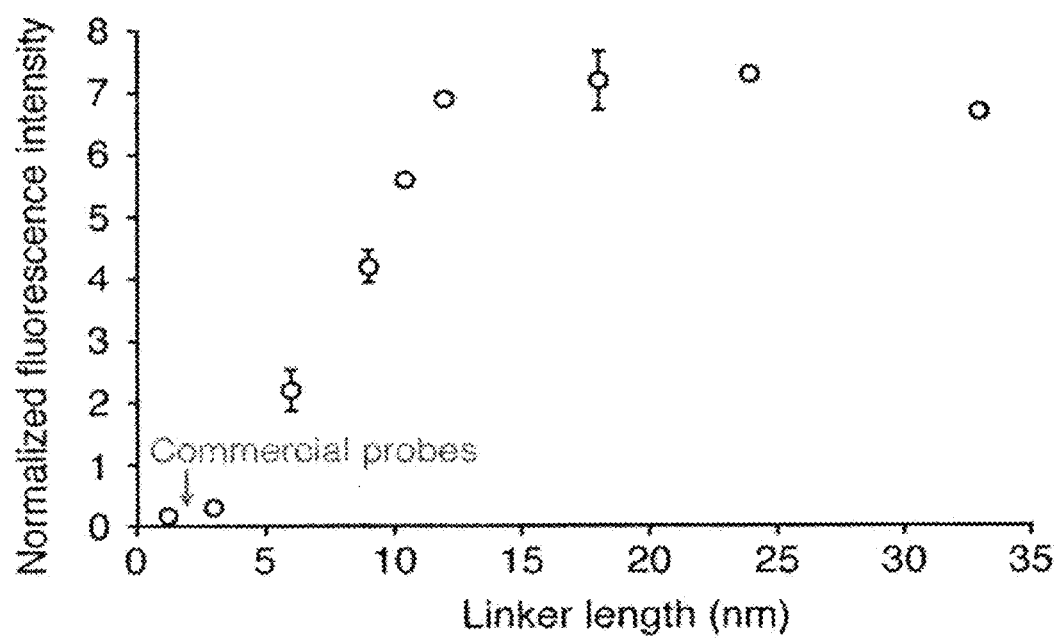
FIG. 12: Increased linker length between oligonucleotide and hapten enables the use of signal amplification systems without tissue permeabilization. To examine the relationship between linker length and signal intensity in non-permeabilized mouse brain tissue, we systematically varied the linker length between a nucleic acid probe targeting 28S rRNA (5' AGTtGTtACACAcTCcTtaG (SEQ ID NO: 3); LNA modifications are indicated in lower case) and its biotin hapten prior to tyramide signal amplification. (a) Linker sequences and lengths (nm) and (b) abbreviations of linkers used in this study are provided. (c) Signal intensities generated by probes with varying linker lengths were normalized against reference signal intensities obtained using four rRNA probes (FIG. 21b) directly labeled with ATTO-532. Linker lengths above 10 nm substantially enhanced signal-amplification-based fluorescence detection. The linker length in commercial probes is typically 1.5 nm (in red) (d) The signal intensity obtained using rRNA-biotin-ATTO-488 with a linker length of 1.2 nm (i) was compared to the same probe using a linker length of 24 nm (iv) at the same exposure time. Reference signals were generated using directly labeled rRNA-ATTO-647N probes (ii,v). Nuclei were visualized using DAPI staining (iii,vi). Images were recorded at 10× magnification. Exposure times are indicated in ms. Scale bar, 50 µm (i-vi).
Figure 12D:
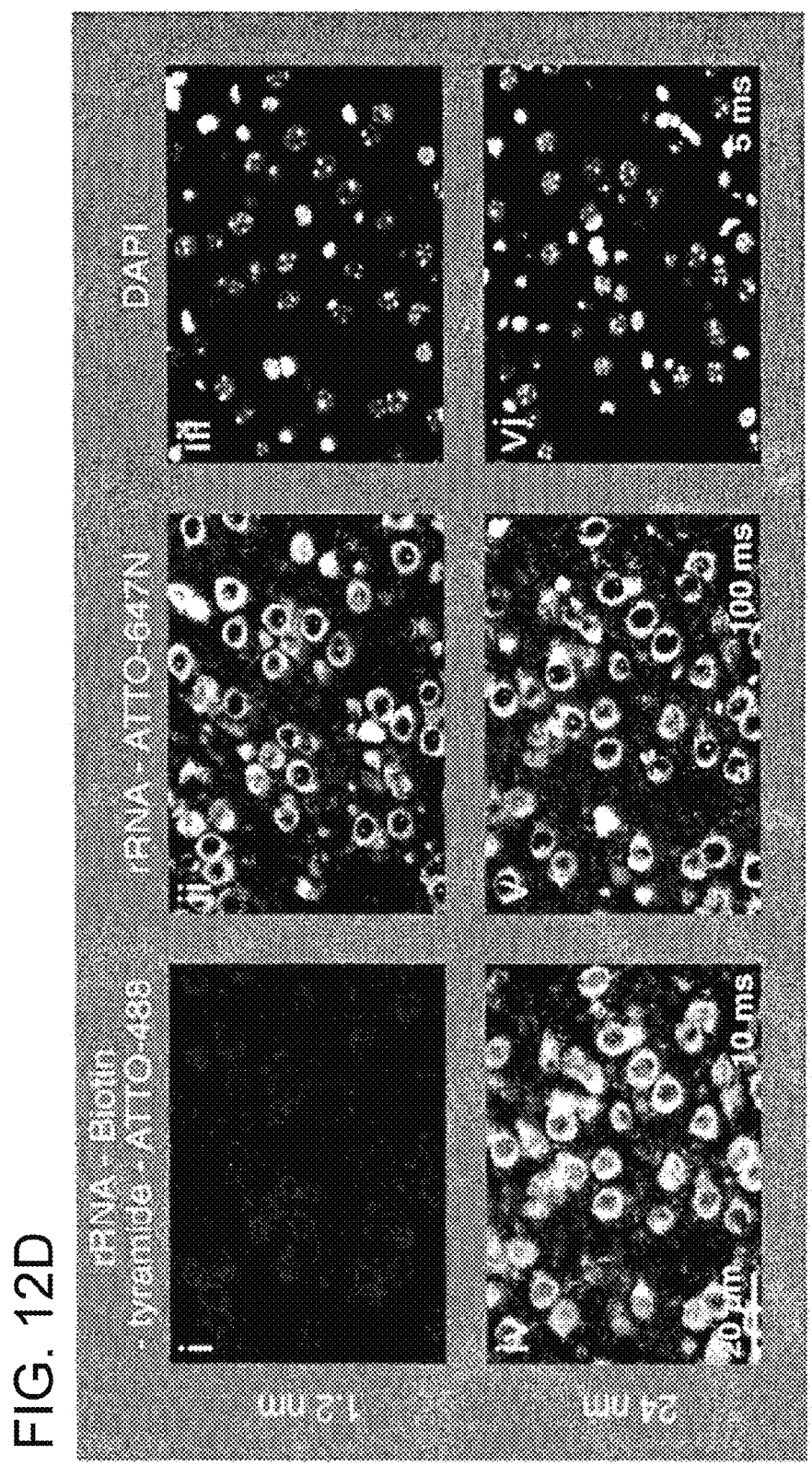

Increased fixation of the protein matrix following EDC treatment was anticipated to hinder access of antibody-based signal amplification reagents to the target-RNA-bound probe-conjugated hapten. Detection of miRNAs by directly labeled probes was not feasible given that these small RNAs are at least 100-fold less abundant than rRNAs and the rRNA signal obtained from directly labeled LNA-modified probes was only 100-fold above background. Despite the need for signal amplification, we were unable to detect miRNAs using commercially available probes and signal amplification reagents. After excluding RNA diffusion, probe-miRNA duplex instability, and insufficient signal amplification as contributing factors, we concluded that antibody-based signal amplification reagents were unable to access the target-RNA-bound probe-conjugated hapten. Since the linker length between probe and hapten is typically short (e.g. the length between an Exiqon LNA probe and digoxigenin is approx. 1.5 nm), we systematically varied the length between the nucleic acid probe and hapten using multiple spacers, finding that a linker length above 10 nm recovered signal-amplification-based fluorescence detection, presumably by displaying the hapten at the surface of the tissue section (FIG. 12).

Figure 22:
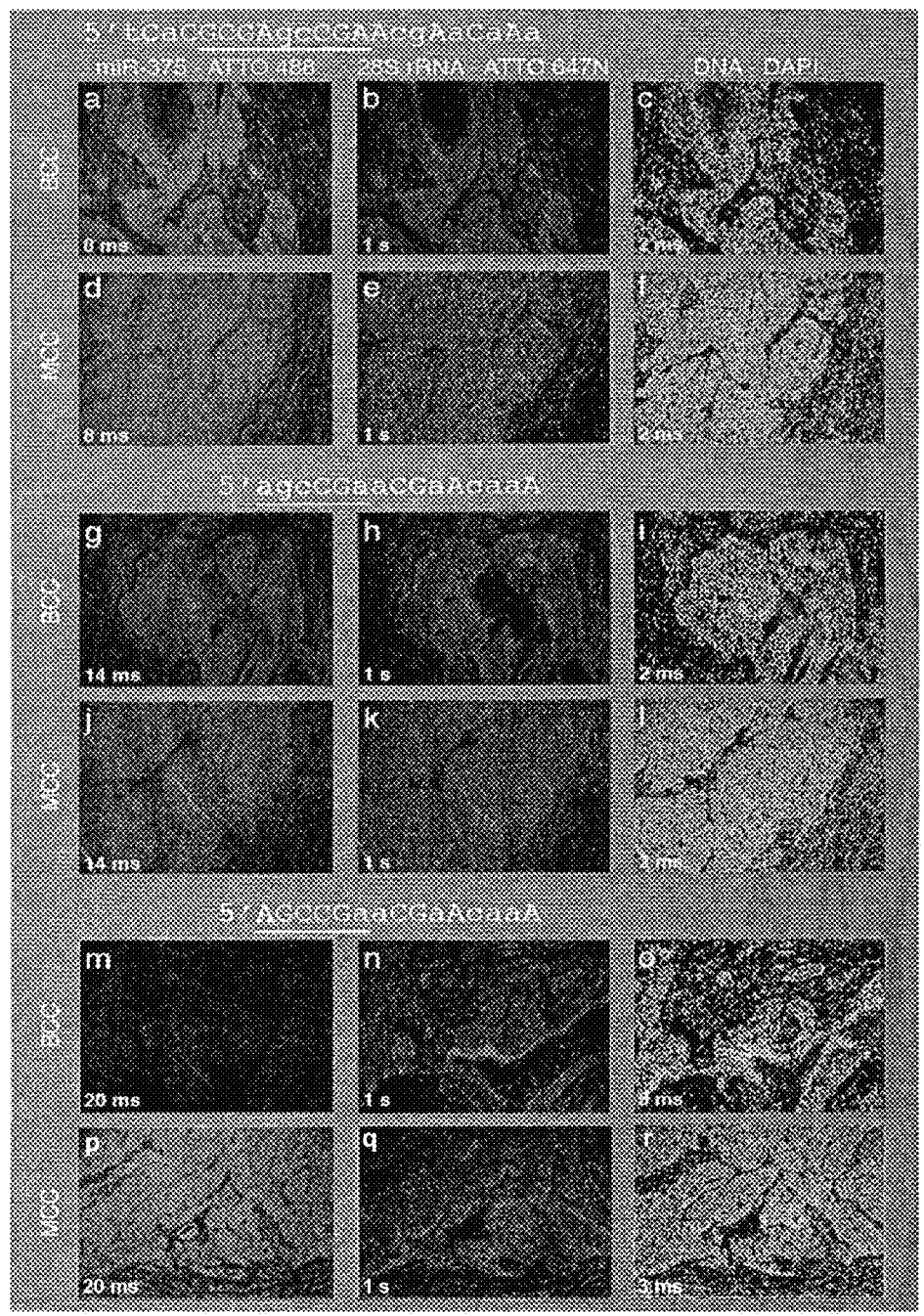
FIG. 22: miR-375 LNA-probe design. miR-375 (a,d,g,j,m, p) and 28S rRNA (b,e,h,k,n,q) hybridization patterns in BCC and MCC tissues were used to assess probe specificity. Probe sequence matches to 28S rRNA are underlined; LNA modifications are indicated in lower case. Antisense miR-375 LNA probe (22 nt, plus 25 nm linker) was detected in (a) BCC and (d) MCC, indicating rRNA mishybridization. Antisense miR-375 LNA probe (15 nt, plus 25 nm linker), with a short (6 nt) sequence match with rRNA, was detected in (g) BCC and (j) MCC, again indicating mishybridization. Removal of three LNA modifications from the region of sequence similarity (third probe sequence) resulted in a substantial decrease (11° C.) in melting temperature, and a specific miR-375 signal ((m) BCC and (p) MCC). Nuclei were visualized using DAPI staining (c,f,i,l,o,r). Images were recorded at 20× magnification. Exposure times are indicated in ms or s. Scale bar, 50 µm (a-r).
Figure 28:
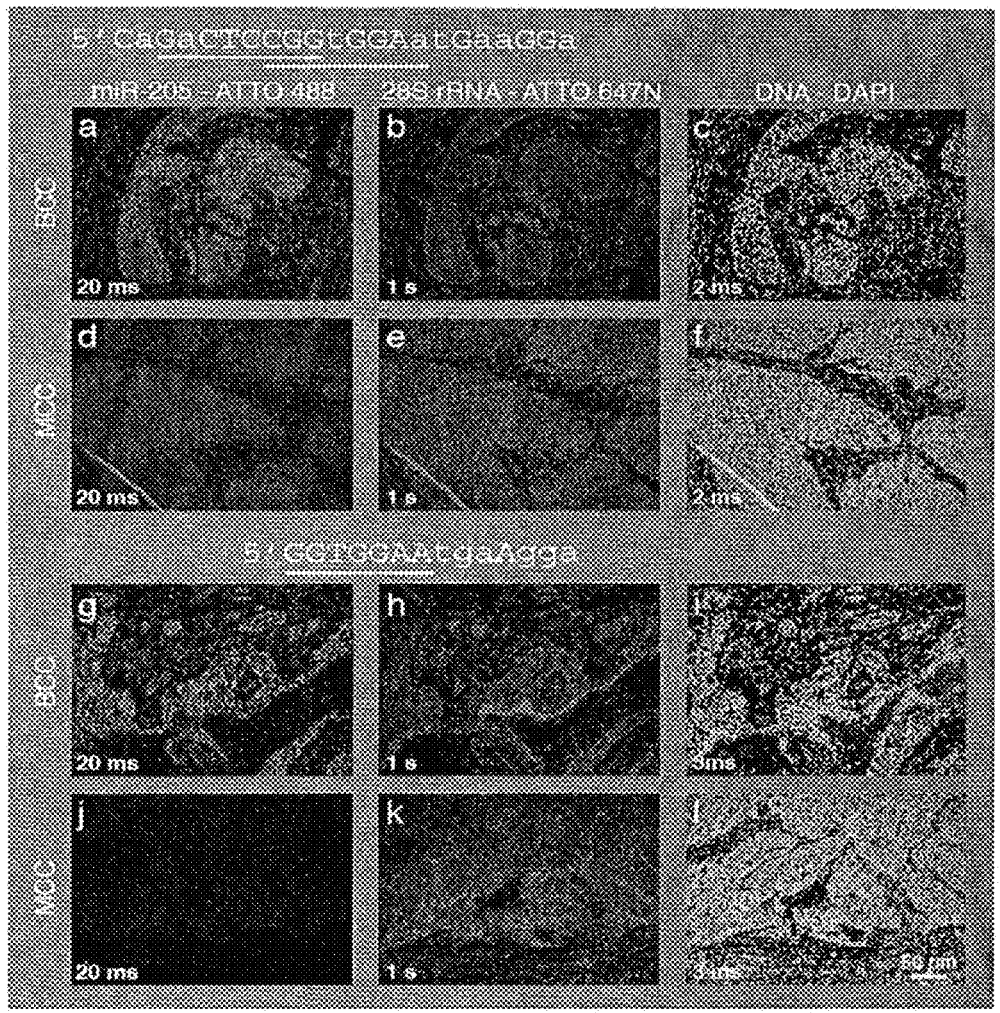
FIG. 28. miR-205 LNA-probe design. miR-205 (a,d,g,j) and 28S rRNA (b,e,h,k) hybridization patterns in BCC and MCC tissues were used to assess probe specificity. Probe sequence matches to 28S rRNA are underlined; LNA modifications are indicated in lower case. Antisense miR-205 LNA probe (22 nt, plus 25 nm linker) was detected in (a) BCC and (d) MCC indicating rRNA mishybridization. Shortening the probe sequence and removal of LNA modifications from the region of sequence similarity, resulted in a substantial decrease (9° C.) in melting temperature, and specific miR-205 signal in BCC (g % j). Nuclei were visualized using DAPI staining (c,f,i,l). Images were recorded at 20× magnification. Exposure times are indicated in ms or s. Scale bar, 50 µm (a-l).

Direct visualization of rRNA by fluorescently labeled probes enabled us to assess RNA fixation and confirm RNA retention and specificity for probe hybridization. As expected, the rRNA signal was predominantly cytoplasmic with the exception of nucleolar staining, indicating the sites of rRNA biogenesis. During our initial studies, we noticed that the probe for miR-375, but not miR-205, yielded an rRNA-like pattern, indicating cross-hybridization. Upon sequence analysis, we realized that short segments of complementarity to rRNA, especially when modified by LNA residues, were responsible for probe mishybridization, and that mishybridization could be corrected through probe shortening and placing LNAs outside segments (not longer than 6 nt) with rRNA sequence complementarity (FIG. 22 and FIG. 28).

Direct visualization of polyA tails by fluorescently labeled polyT probes could also be used to assess RNA retention, integrity, and specificity for probe hybridization. Interestingly, we were able to differentiate solitary cases of MCC and BCC based on polyA:rRNA signal ratios; these ratios were approximately three times in higher in BCC than MCC. PolyA and rRNA signals potentially serve as surrogate markers of transcriptional and translational activities respectively and may be useful normalization controls against which gene-specific expression can be assessed.

To enhance signal detection, we used the tyramide signal amplification system. The HRP-mediated tyramide coupling reaction was performed in the presence of 4-bromoboronic acid to enhance HRP-catalyzed oxidation. We confirmed optimal tyramide signal amplification for our reagent set by preparing Cy3-tyramide reagents and buffers for comparison with commercial Cy3-tyramide equivalents. Instead of using Cy-dyes, however, we used ATTO-dyes (http://www.atto-tec.com/) that are more stable and brighter. We synthesized ATTO-tyramides since they were not commercially available, selecting the most water-soluble derivatives, namely ATTO488, ATTO532 and ATTO655.

Figure 23:
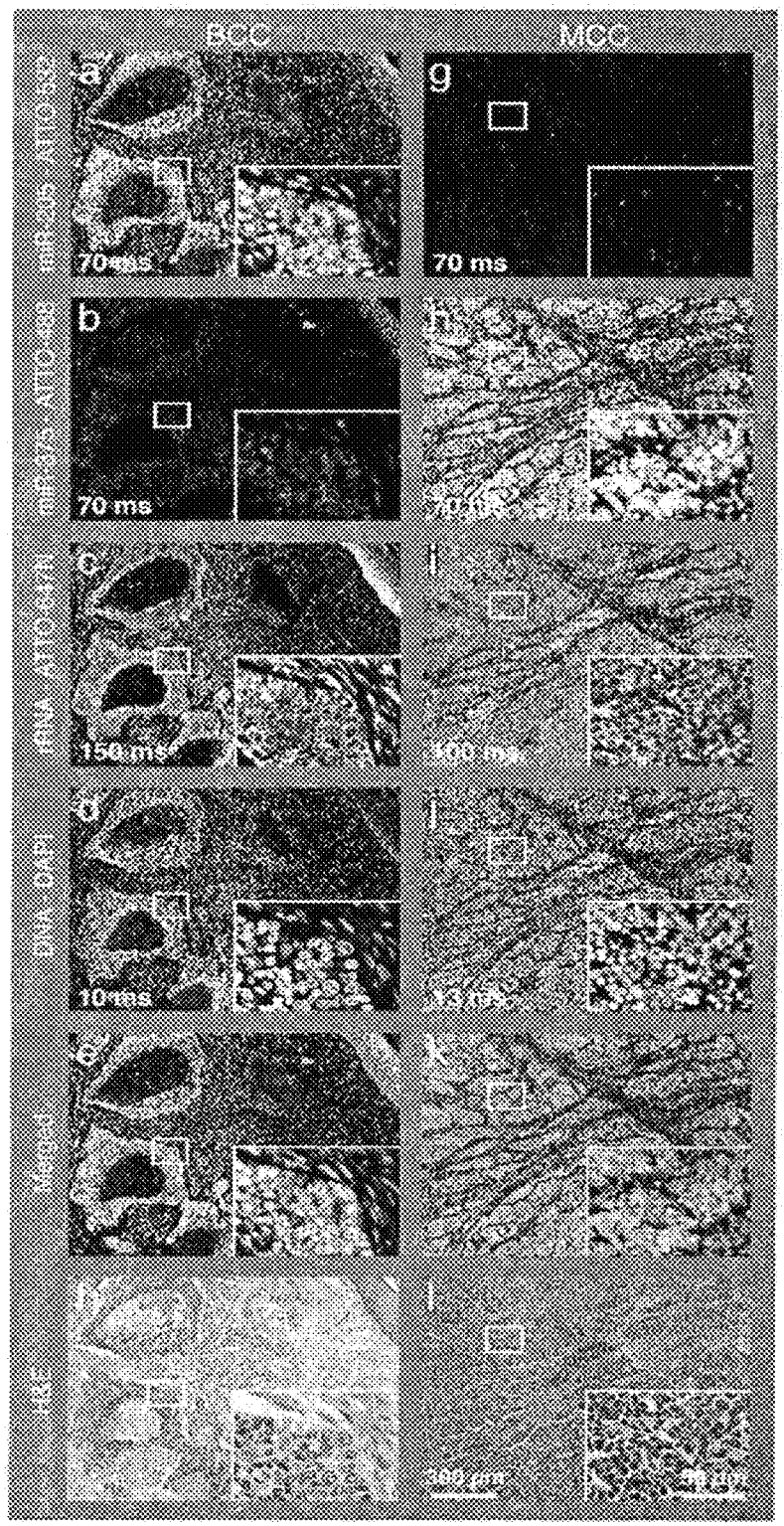
FIG. 23. Multicolor miRNA FISH for BCC and MCC differential diagnosis. Parallel detection of miR-205, miR-375, and 28S rRNA in FFPE BCC and MCC tissue sections (samples BCC1 and MCC1) by multicolor miRNA FISH. All probes (25 nM) were co-hybridized at 55° C. for 16 h in hybridization buffer containing 50% formamide and 1.0 M NaCl. miR-205 was detected using a 14-nt fluorescein-labeled (conjugated to 6 fluorescein moieties) LNA-modified probe and anti-fluorescein-HRP antibody with and tyramide: ATTO-532 signal amplification. miR-375 was detected using a 15-nt biotin-labeled (conjugated to 6 biotin moieties) LNA-modified probe with HRP-conjugated streptavidin and tyramide:ATTO-488 signal amplification. miR-205 signal intensities were higher in BCC (a) than MCC (g) whereas miR-375 signal intensities were conversely higher in MCC (h) than BCC (b), consistent with our small RNA sequencing results. 28S rRNA was detected without signal amplification by a cocktail of four fluorescent ATTO-647N-conjugated probes (c, i). 28S rRNA signals were similar for both BCC and MCC and used to normalize miR-205 and miR-375 signals. Nuclei were visualized using DAPI staining (d, j). Merged images (e, k) depict BCC in yellow and MCC in green, enabling rapid tumor identification. Hematoxylin-eosin (H&E) stained tissue sections (f, l) illustrate the potential for histologic similarity between BCC and MCC. Images were recorded at 20× magnification. Representative areas, indicated by white rectangles, are shown at 60× magnification to illustrate signal localization. Exposure times are indicated in ms. Scale bar, 300 µm, for insert, 50 µm (a-l).

Having identified distinct miRNA expression patterns in MCC and BCC and optimized the herein miRNA FISH protocol, we validated our approach on FFPE tissue sections from 12 MCC and 4 BCC cases. We performed multicolor FISH using a cocktail of ATTO-647N-conjugated probes complementary to 28S rRNA (directly labeled), fluorescein-labeled miR-375 probe (detected using anti-fluorescein-HRP antibody and tyramide:ATTO532), and biotin-labeled miR-205 probe (detected using HRP-conjugated streptavidin and tyramide:ATTO488). miR probe intensities were normalized against the rRNA intensity and fluorescence signal ratios of 375:205 and 205:375 probes were used to classify tumors as MCC or BCC (FIG. 23).

The herein miRNA FISH method has several advantages over existing methods. For example, (1) increased RNA retention in tissues using EDC crosslinking, omitting competing phosphate-containing buffers (2) established controls for assessing RNA retention and normalizing specific signals (such as miRNAs) using directly labeled fluorescent probes for rRNA and polyA (3) enhanced antibody-based fluorescence signal amplification and eliminated the need for tissue permeabilization through the use of long linkers between the hapten and oligonucleotide probe providing more specific and quantitative data and (4) optimized the method to use archived FFPE tissue sections.

The invention has lead to identification of several other interesting pathogenetic features of MCC and BCC. It has been shown that (1) MCC and BCC consistently express miR-375 and miR-205 despite variable underlying cytogenetic changes in these tumors, adding further weight to their respective roles as oncomirs and tumor suppressors (2) MCV miRNA expression in MCC is low, favoring tumor cell growth and survival (3) miRNA sequence variation representing polyadenylation or polyuridylation sequence modifications and RNA editing. It has also been shown that in MCC, the miR-375 signal changes from cytoplasmic to nuclear on the same tissue section and close to areas of hypoxia or metastasis.

Example 2 miRNAs are valuable disease biomarkers because of their cell-type specificity and abundance. We developed barcoded small RNA sequencing for simultaneous miRNA profiling and quantitation in multiple samples. Through profiling and discriminant analysis, we identified a distinct, inverse relationship between miR-205 and miR-375 expression that differentiated two skin tumors with shared histologic features, namely basal cell carcinoma (BCC) and Merkel cell carcinoma (MCC).

We designed probes targeting these tumor-specific biomarkers and rRNA to establish multicolor miRNA fluorescence in situ hybridization (FISH) on formalin-fixed paraffin-embedded (FFPE) tissue sections. Amplified miRNA signals were corrected and normalized against directly detectable reference rRNA signals and tumor-specific cut-off values were established. We subsequently validated our method on 16 BCC and MCC tumors, correctly identifying all tumors in a blinded analysis. Parallel visualization of differentially expressed miRNAs in FFPE tissues is a broadly-enabling advance in RNA molecular diagnostics.

Consistent detection of tumor-specific miRNA expression profiles indicates that some small RNAs are valuable disease biomarkers. To date, miRNA profiling has been used to classify cancers of known and unknown primary origin, determine prognosis and disease progression, predict chemoresistance, monitor therapy, and screen for disease. Given widespread clinical utility, there is a significant need for advanced miRNA detection, quantitation, and visualization assays for diagnostic or classificatory purposes.

To establish miRNA-based diagnostics, it is essential to (1) define a clinical need (2) reliably extract small RNAs from clinical materials (3) detect and quantitate miRNA expression differences between samples and (4) establish tractable tests for clinical laboratory use. Because miRNAs accurately identify cancer tissue origin, we sought to establish a multicolor FISH protocol to visualize differentially expressed miRNAs in FFPE tissues. While miRNA microarray and/or real-time PCR analyses of fresh or archived materials can be used for molecular diagnostics, these approaches obliterate valuable cytoarchitectural details.

To develop and optimize miRNA visualization methods, we focused on BCC and MCC, which we posited might contain distinct miRNA expression signatures due to their different cellular origins. These tumors can be diagnostically challenging, requiring differentiation from each other and from small cell carcinoma (metastatic from lung), squamous cell carcinoma, lymphoma, and amelanotic melanoma. Histologic evaluation is typically performed using immunohistochemical stains for cytokeratins (CK7, CK20), chromogranin, synaptophysin, and thyroid transcription factor 1, among others. Differentiating BCC and MCC based on miRNA expression presented an unparalleled opportunity for optimizing miRNA FISH and is clinically relevant because accurate histopathological diagnosis guides subsequent treatment.

In this study, we detected and quantitated miRNA expression differences between BCC, MCC, and normal skin (NS) samples using barcoded small RNA sequencing and developed a multicolor miRNA FISH protocol targeting tumor-specific miRNAs and rRNA. We addressed shortcomings in (1) RNA fixation (2) signal amplification and detection and (3) probe design that impede short (e.g. miRNA) and long (e.g. mRNA and rRNA) RNA visualization. We also tested our samples for Merkel cell polyomavirus (MCV) as this virus causes approx. 80% MCC cases and encodes a miRNA, potentially influencing cellular miRNA expression and sample clustering.

To assess miRNA expression differences between tumors, we first extracted total RNA from 36 archived clinical materials and cultured cell lines from patients with BCC, MCC, and NS (FIG. 16). We subsequently profiled and quantitated miRNAs in all samples using barcoded small RNA sequencing. Sequence reads were annotated by RNA category (FIG. 17). Total miRNA concentrations were calculated from sequence read frequencies of miRNAs relative to spike-in calibrator RNAs (FIG. 18). Higher total miRNA concentrations were seen in Trizol-extracted cell lines compared to Masterpure- or RecoverAll-extracted FFPE samples (FIG. 3). To minimize the effects of sample processing and/or RNA extraction method on RNA recovery, we compared concentrations in RecoverAll-extracted FFPE samples from sequencing run one (hereafter termed the training set). Total miRNA concentration was two-fold higher in BCC than in MCC or NS whereas no significant difference was seen between MCC and NS (FIG. 3). Tumor-specific differences in total miRNA concentration may reflect altered rates of miRNA biogenesis, processing, or degradation.

Figure 1:
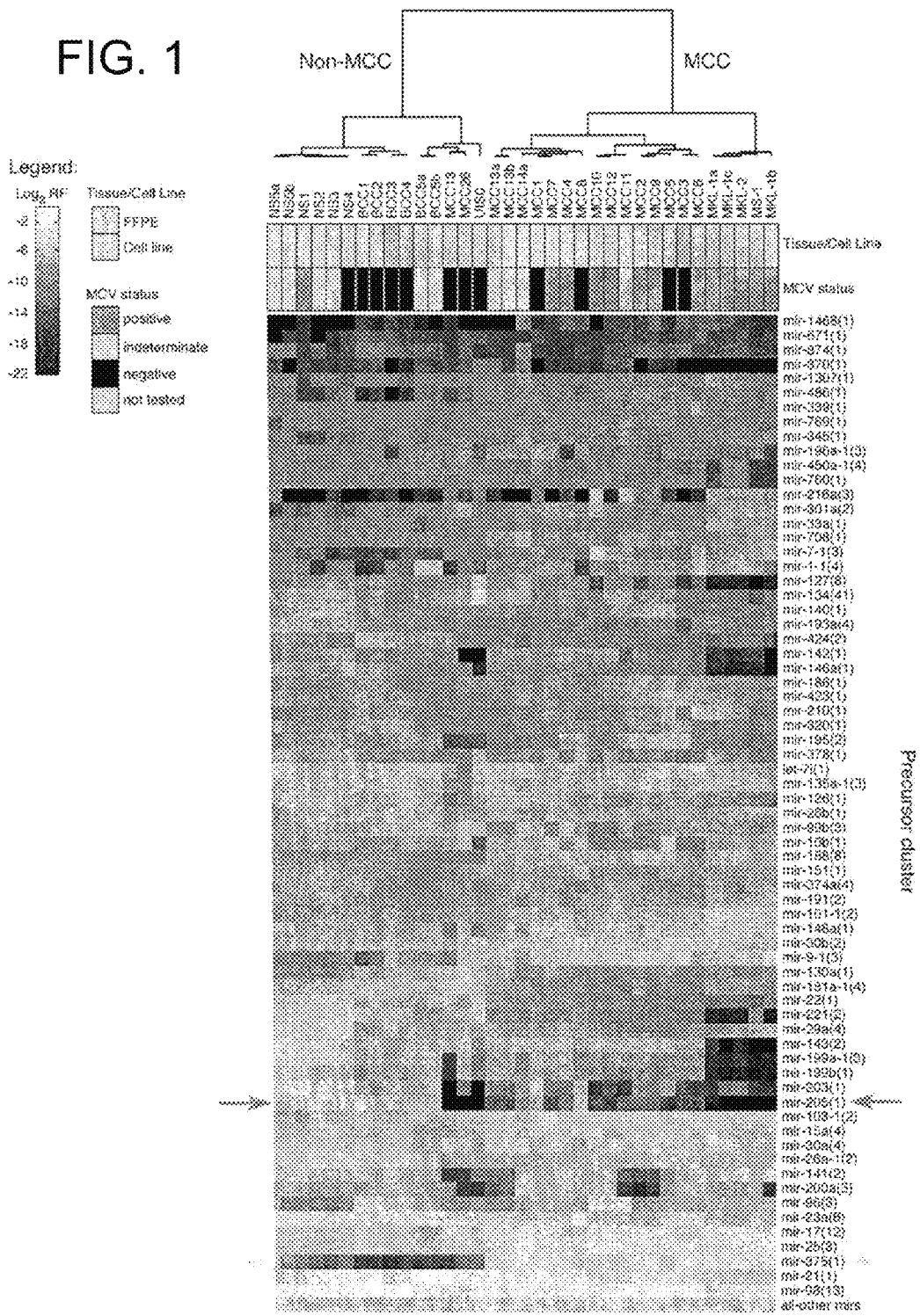
FIG. 1: Unsupervised hierarchical clustering of miRNA expression profiles. Unsupervised hierarchical clustering was performed using log 2 relative frequencies of miRNA precursor cluster sequence reads for the given cell line and formalin-fixed and paraffin-embedded (FFPE) tissue samples; MCV status is also indicated where available. miRNA precursor clusters were selected from the top 85% expressed miRNA precursor clusters across all samples. The number of members per precursor cluster is indicated in brackets following the miRNA gene name; precursor clusters are named according to Farazi et al. miR-205 and miR-375 expression values for all samples are respectively indicated by red and green arrows.
Figure 2:
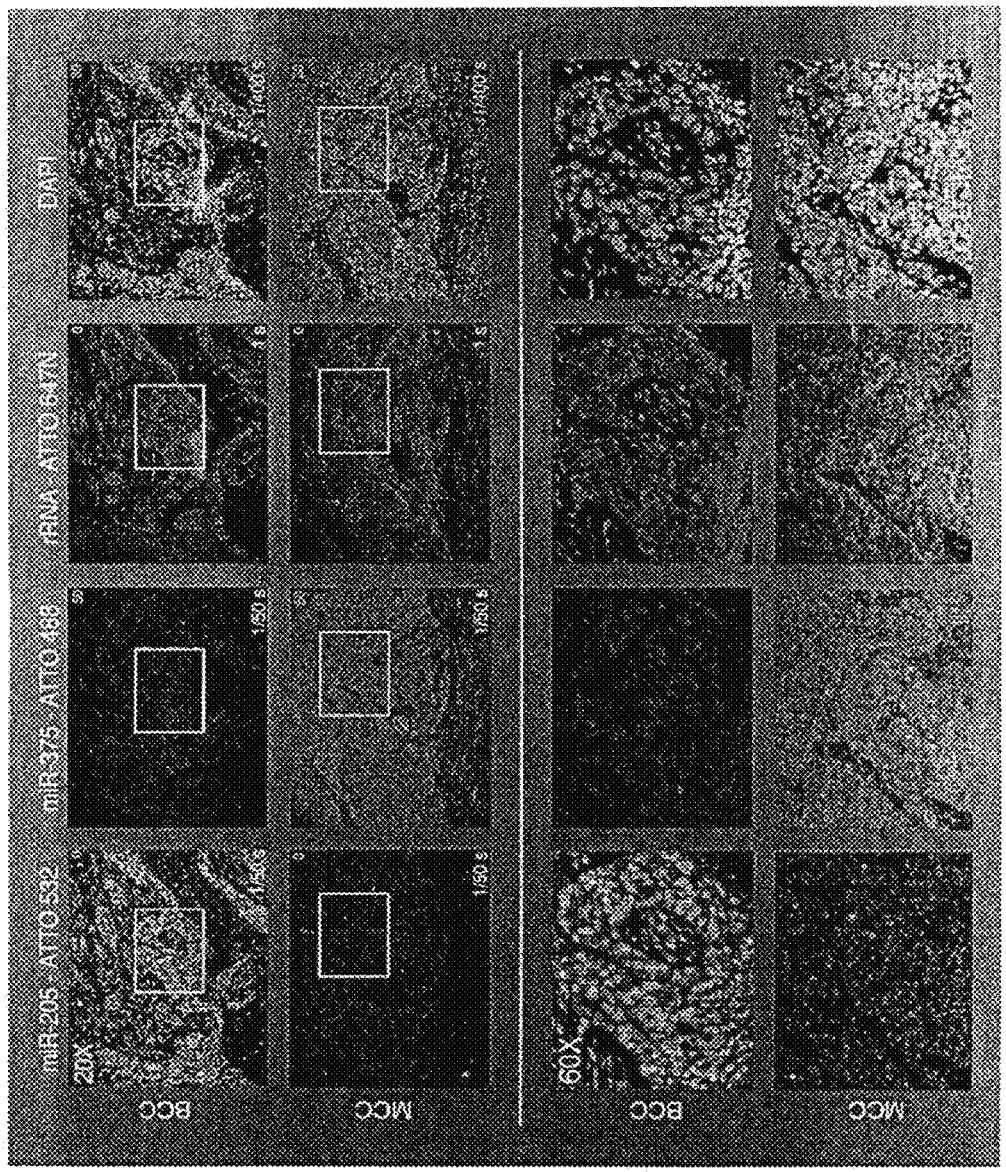
FIG. 2: Multicolor miRNA FISH enabled differentiation of MCC and BCC; two histologically similar skin tumors. Co-detection of miR-205, miR-375, and 28S rRNA in FFPE MCC and BCC tissue sections using multicolor miRNA FISH. All probes (0.1 µM) were hybridized at 55° C. for 16 h in hybridization buffer containing 50% formamide and 1.0 M NaCl. Biotin-labeled miR-205 probe was detected using HRP-conjugated streptavidin and tyramide:ATTO488. Fluorescein-labeled miR-375 probe was detected using anti-fluorescein-HRP antibody and tyramide:ATTO532. Directly labeled ATTO647N-conjugated probes were used to detect 28S rRNA. Nuclei were visualized using DAPI staining miR-375 signal intensities were higher in MCC than BCC whereas miR-205 signal intensities were conversely higher in BCC than MCC (see panels), which was also confirmed by RNA sequencing analysis. 28S rRNA signals were similar for both MCC and BCC and were used to normalize miR-375 and miR-205 signals. Images were acquired using an Olympus microscope and recorded with a CCD digital camera at 20× magnification. Representative areas, indicated by white rectangles, are shown at 60× magnification to illustrate signal localization. Exposure times are indicated in s.

Hierarchical clustering of miRNA cluster sequence read frequencies indicated two major groups corresponding to MCC and non-MCC (BCC and NS) tumors and cell lines (FIG. 1). To minimize sample processing and extraction differences, we clustered training set samples only and saw the same grouping (data not shown). Interestingly, MCV-positive MCC-derived cell lines (MKL-1, MKL-2, MS-1) clustered in the MCC group whereas MCV-negative MCC-derived cell lines (MCC13, MCC26, UISO) clustered in the non-MCC group. When compared with miRNA profiles from approx. 1,000 clinical samples in our database, MKL-1, MKL-2, and MS-1 clustered with MCC tumors whereas MCC13 clustered with liposarcoma cell lines and MCC26 and UISO clustered with breast cancer cell lines suggesting that some cell lines are either MCV-negative MCC variants or misclassified. Sample clustering was not influenced by the low number of MCV miRNA sequence reads (<30 per sample) in MCC tissues.

We compared miRNA expression profiles between MCC and non-MCC groups and identified tumor-specific miRNAs through discriminant analysis. These groups were accurately differentiated based on miR-205 and miR-375 expression, with no errors in the training set (sequencing run one) and one misassignment (sample NS5a) in the testing set (sequencing run two). Significant differences in miR-205 and miR-375 concentrations were seen between MCC and non-MCC groups (ANOVA NMCC group=20, Nnon-MCC group=15); miR-205 concentrations were 4.5-fold higher in non-MCC than MCC (padj=0.26) and miR-375 concentrations were 60-fold higher in MCC than non-MCC (padj<0.001) groups (FIG. 4). Significant differences were again seen when analyzing training set samples only (ANOVA padj<0.001, NMCC=12, Nnon-MCC=8); miR-205 concentrations were 308-fold higher in non-MCC than MCC (padj<0.001) whereas miR-375 concentrations were 577-fold higher in MCC than non-MCC (padj<0.001) groups (FIG. 4). We confirmed grouping and expression differences in a subset of MCC and NS samples using miRNA microarray and real-time RT-PCR analyses (FIG. 4).

After identifying tumor-specific biomarkers for BCC (miR-205) and MCC (miR-375), we established a multicolor miRNA FISH protocol suitable for use on FFPE tissue sections. To achieve this goal, we revisited RNA fixation, signal detection and amplification, and oligonucleotide probe design steps. Suboptimal RNA fixation leading to short and long RNA loss by diffusion, rather than RNA degradation, is the primary problem in optimizing RNA ISH. To resolve this problem, we previously reported the use of EDC (1-ethyl-3-(3-dimethylaminopropyl)carbodiimide), a water-soluble condensation reagent which promotes phosphoamide bond formation between the miRNA 5' phosphate end and aliphatic amines from amino acid side chains of surrounding proteins (FIG. 5).

Figure 8:
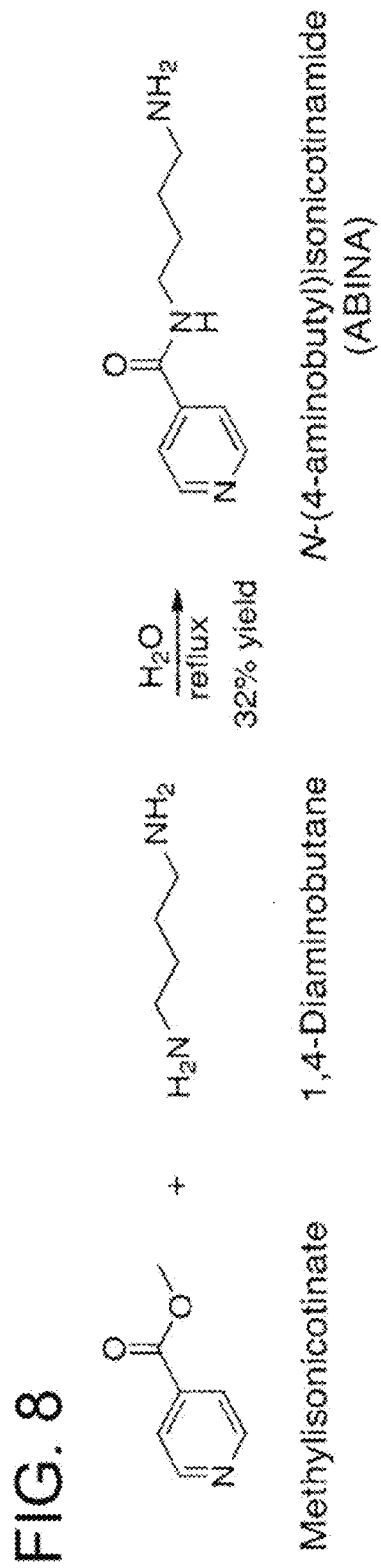
FIG. 8: Schematic diagram of ABINA synthesis. ABINA is a highly soluble UV-absorbing compound that was prepared by refluxing methylisonicotinate and 1,4-Diaminobutane in water (see Methods).
Figure 9A:
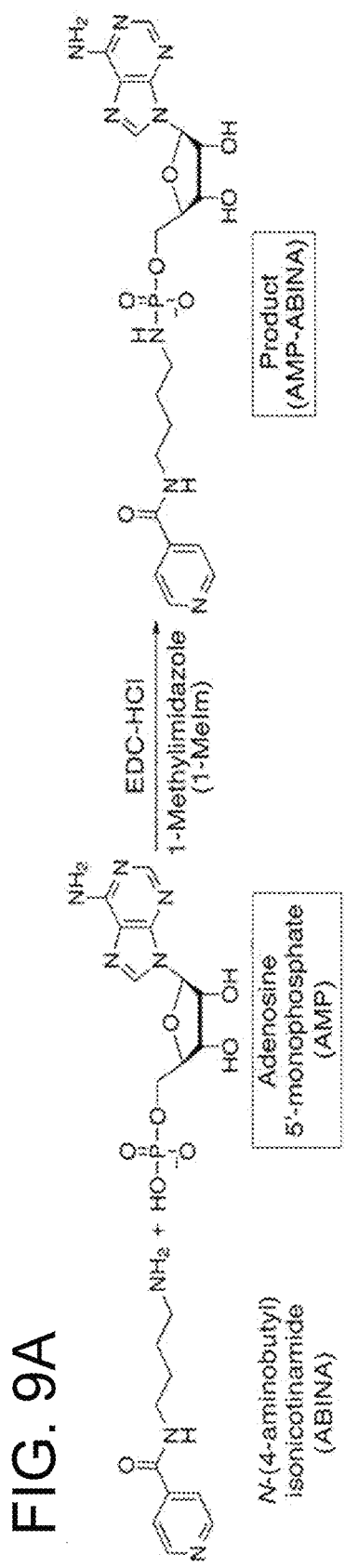
FIG. 9: Carbodiimide-mediated condensation using UV-absorbing model compounds. (a) The reaction between AMP and ABINA at 50° C. yielded a stable phosphoramidate product AMP-ABINA. (b) HPLC traces recording UV 260 nm absorbance of reaction products during a 7 h time course of a model condensation reaction at pH 8. Peaks corresponding to AMP (highlighted blue), synthesized amine ABINA, and crosslinking product Amp-ABINA (highlighted red), 1-Methylimidazole (1-MeIm) and side products (*) are marked. Reaction times and product yields are indicated. The XL-product reverted to AMP and ABINA upon incubation in 80% acetic acid, as expected for a phosphoramidate. (c) The highest yield (95%) of ABINA occurred at pH 8.
Figure 9B:
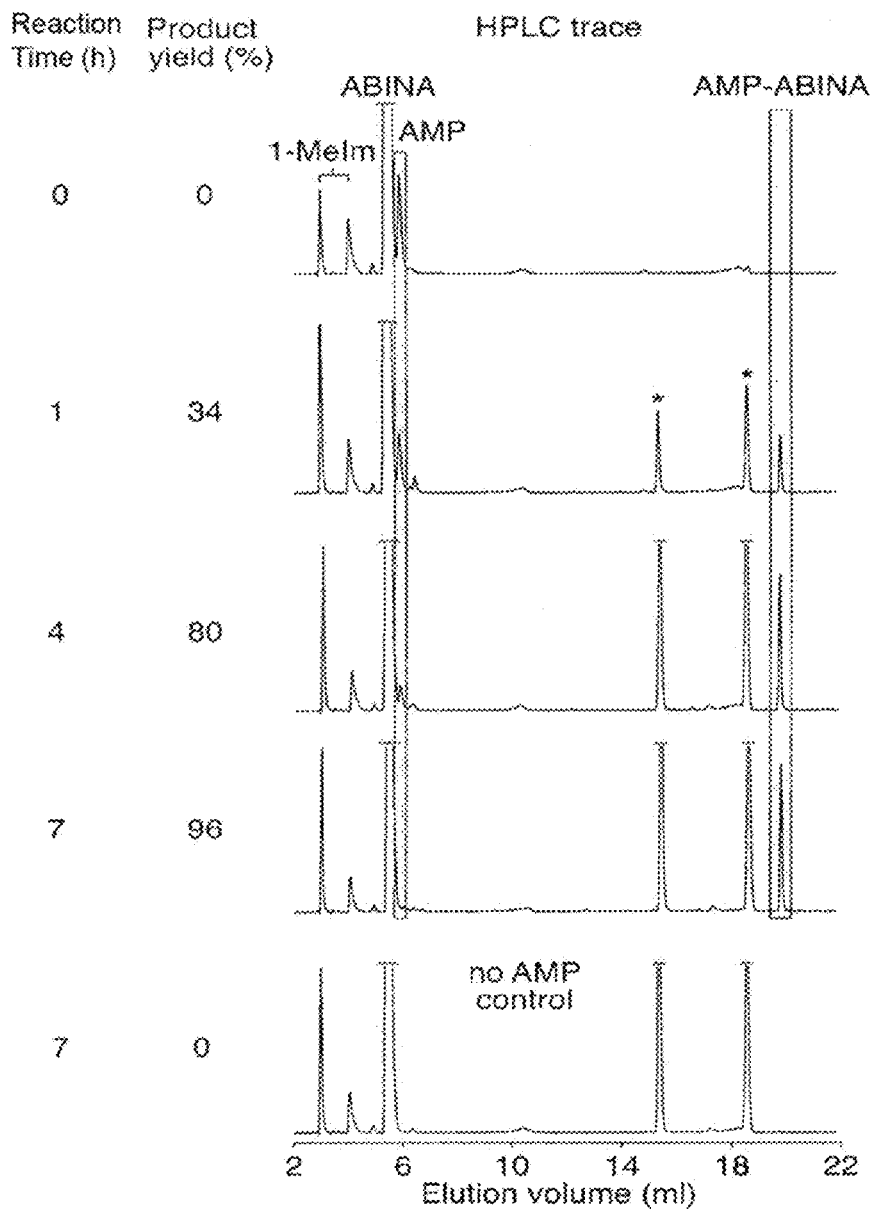
Figure 9C:
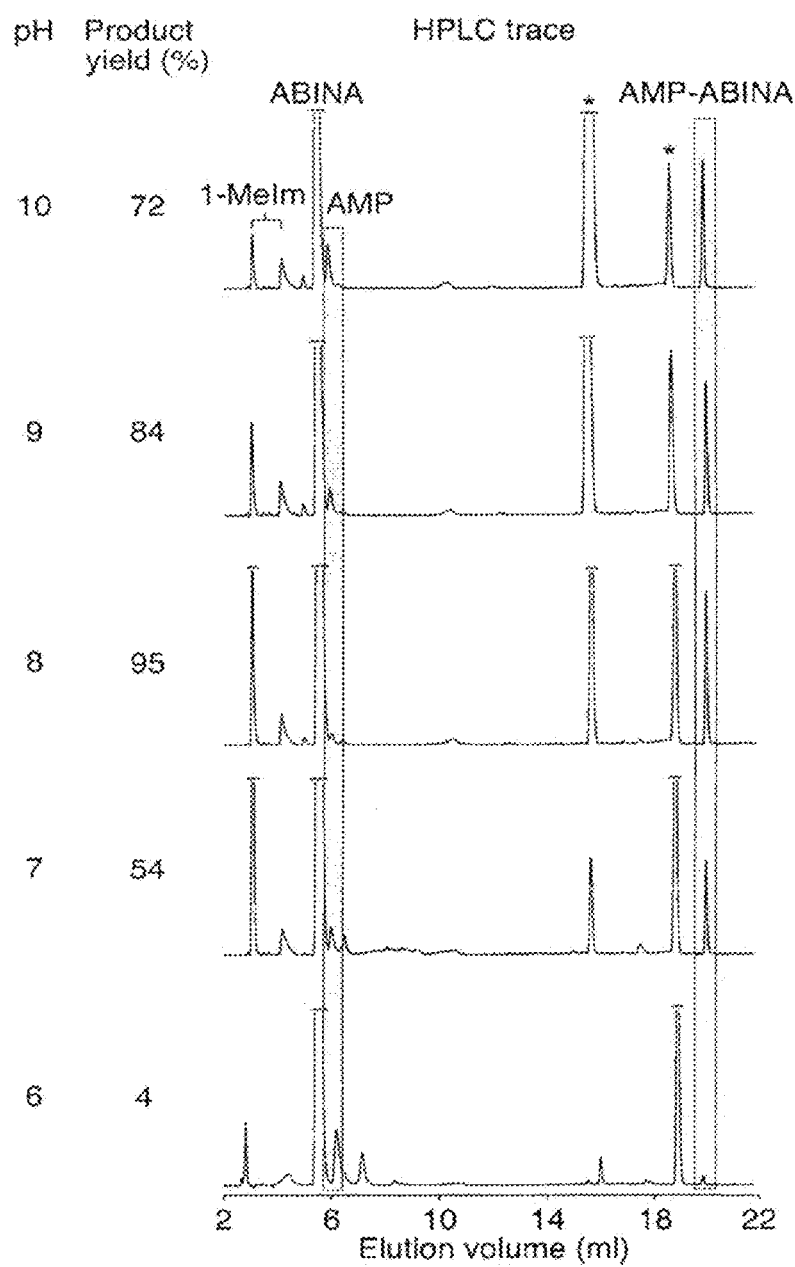

We further studied the EDC condensation reaction in vitro by reacting 5' adenosine monophosphate (5' AMP) and modified peptides; near complete phosphoamide bond formation was seen following incubation at pH 8 for 10 h at 50° C. (FIG. 6). We found that the phosphate moiety predominantly reacted with the primary amine of lysine (FIG. 7). We also observed a pH-dependent hydrolysis side-reaction of the EDC-miRNA intermediate that reduced crosslinking between protein and miRNA. To further investigate the condensation and side reactions, we prepared N-(4-aminobutyl) isonicotinamide (ABINA), a highly soluble UV-absorbing model compound with a pKa similar to the lysine side chain amine (FIG. 8). We subsequently optimized condensation reaction conditions by reacting ABINA with AMP (FIG. 9) in the presence of various EDC derivatives (FIG. 19) and heterocyclic compounds (FIG. 20) that form stable reaction intermediates and reduce hydrolysis. The reaction time was reduced to 1 h using EDC-methiodide (MeI) and 5-ethylthio-1H-tetrazole (5-ETT). The use of two heterocyclic derivatives (1-methylimidazole and 5-ETT) also resulted in competing intermediate formation, enhancing nucleophilic attack of the aliphatic amine and rapid crosslinking (FIG. 5b). We ultimately selected EDC hydrochloride (EDC-HCl) and 5-ETT in 1-methylimidazole buffer for miRNA crosslinking because the short reaction time (3 h) minimizes miRNA diffusion during EDC fixation. Furthermore, northern blot analysis showed that miRNA retention substantially increased upon EDC fixation (FIG. 46).

Figure 27:
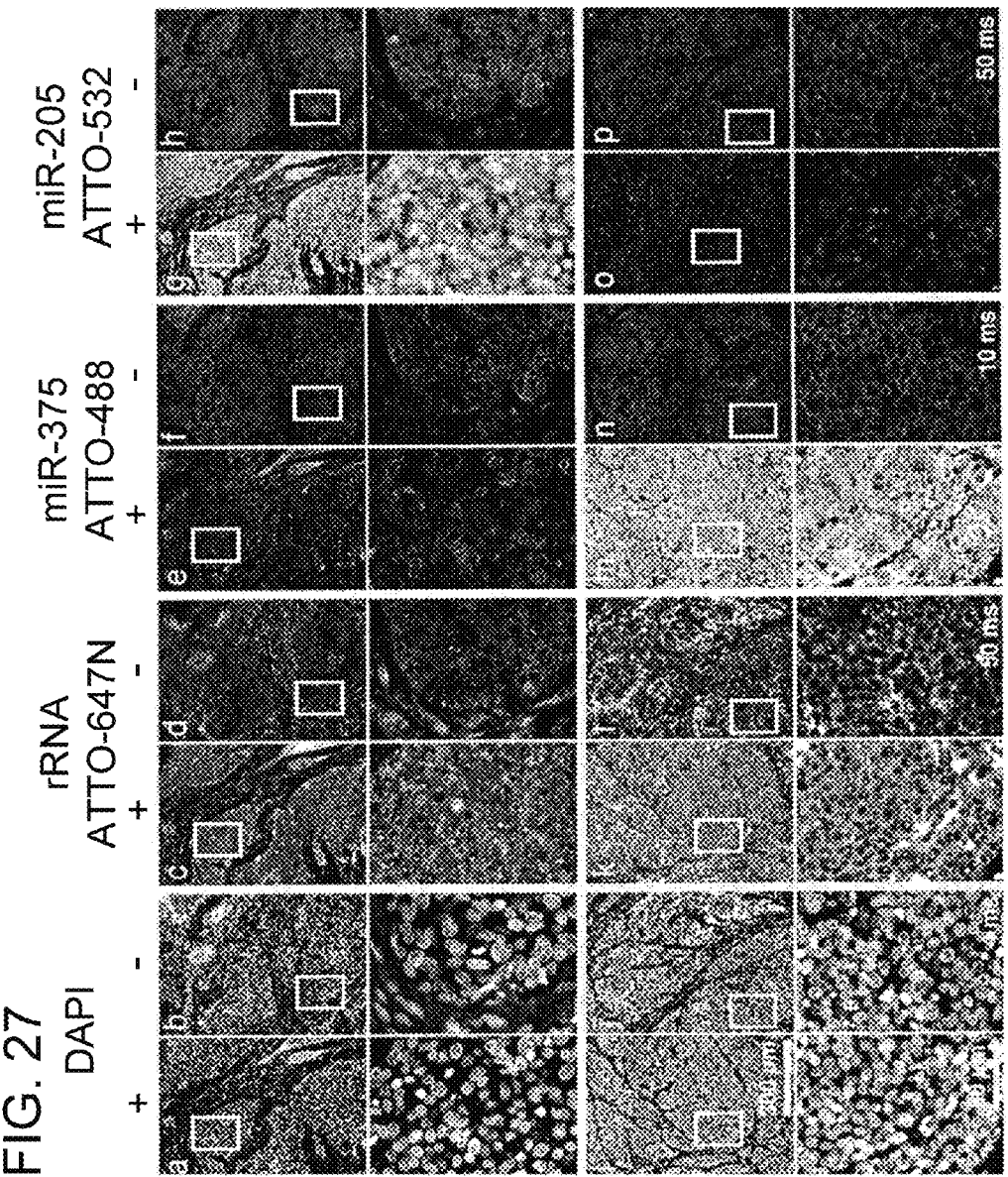
FIG. 27. EDC-based retention of long (rRNA) and short (miRNA) RNAs in FFPE tissues. Multicolor miRNA FISH was performed on BCC and MCC tissues with (+) and without (−) EDC fixation. rRNA signals were brighter in EDC-fixed (c, k) than unfixed (d, l) tissues, indicating retention. miR-205 and miR-375 signals were identified as expected in EDC-fixed (e, g, m, o) but not unfixed (f, h, n, p) tissues. Images were recorded at 60× magnification. Exposure times are indicated in ms. Scale bar, 300 µm, for insert 50 µm (a-p).

In addition to miRNA crosslinking, EDC promoted protein crosslinking through the formation of carboxylic acid amide bonds. We modeled this reaction using ABINA and 3-pyridylacetic acid (FIG. 10) and observed complete amide bond formation after 6 h, twice the completion time for phosphoamide bond formation under the same reaction conditions. To assess the effects of protein crosslinking on tissue sections, we monitored the retention of abundant long RNAs. Paraffin-embedding of formalin-fixed tissues is accompanied by mild RNA hydrolysis and fragmentation of RNAs in to smaller pieces. Hydrolysis products carrying 2',3' cyclic and 2' or 3' phosphate termini do not yield stable phosphoamide bonds. We detected 28S ribosomal RNA (rRNA) using directly labeled fluorescent LNA-modified oligodeoxynucleotide probes complementary to rRNA sequences. As expected, the rRNA signal was predominantly cytoplasmic with the exception of nucleolar staining, indicating the sites of rRNA biogenesis. EDC fixation increased the retention of partially hydrolyzed rRNAs (FIG. 27). Monitoring rRNA enabled us to assess RNA fixation, confirm RNA retention, integrity, and specificity for probe hybridization, and normalize miRNA signals.

Following EDC treatment, increased fixation of the protein matrix was anticipated to hinder access of antibody-based signal amplification reagents to the target-RNA-bound probe-conjugated haptens. miRNA detection by directly labeled probes was not possible because these small RNAs are at least 100-fold less abundant than rRNAs and the rRNA signal obtained from one directly labeled LNA-modified probe was only 100-fold above background (data not shown). To enable access of the target-RNA-bound probe-conjugated hapten to detection antibodies, we systematically varied the linker length between the nucleic acid probe and hapten. Using rRNA as a target, we compared a biotin-labeled oligonucleotide probe with varying linker lengths to a set of directly labeled fluorescent probes hybridizing at distinct sites; linker lengths above 10 nm substantially improved signal-amplification-based fluorescence detection, presumably by displaying the hapten at the surface of the tissue section (FIG. 12).

To amplify the hybridization signal of hapten-conjugated probes, we used tyramide signal amplification and enhanced the horseradish peroxidase (HRP)-mediated oxidative tyramide coupling reaction by adding 4-bromophenylboronic acid. We confirmed optimal tyramide signal amplification for our reagent set by preparing Cy3-tyramide reagents and buffers for comparison with commercial Cy3-tyramide equivalents. After optimizing the reaction, we switched to ATTO-dyes that are brighter, more stable, and water-soluble.

Direct visualization of rRNA by fluorescently labeled probes enabled us to assess probe specificity. Mishybridization of LNA-modified miRNA probes to rRNA was detected through co-localization of signals to nucleoli. During our initial studies, we noticed that the probe for miR-375, and miR-205 to a lesser degree, yielded an rRNA-like pattern, indicating cross-hybridization (FIGS. 22 and 28, respectively). Upon sequence analysis, we realized that short segments of complementarity to rRNA, especially when modified by LNA residues, were responsible for probe mishybridization to rRNA, and could be corrected through probe shortening and placing LNAs outside segments (not longer than 6-7 nt) with rRNA sequence complementarity (FIGS. 21, 22 and 28).

Figure 24:
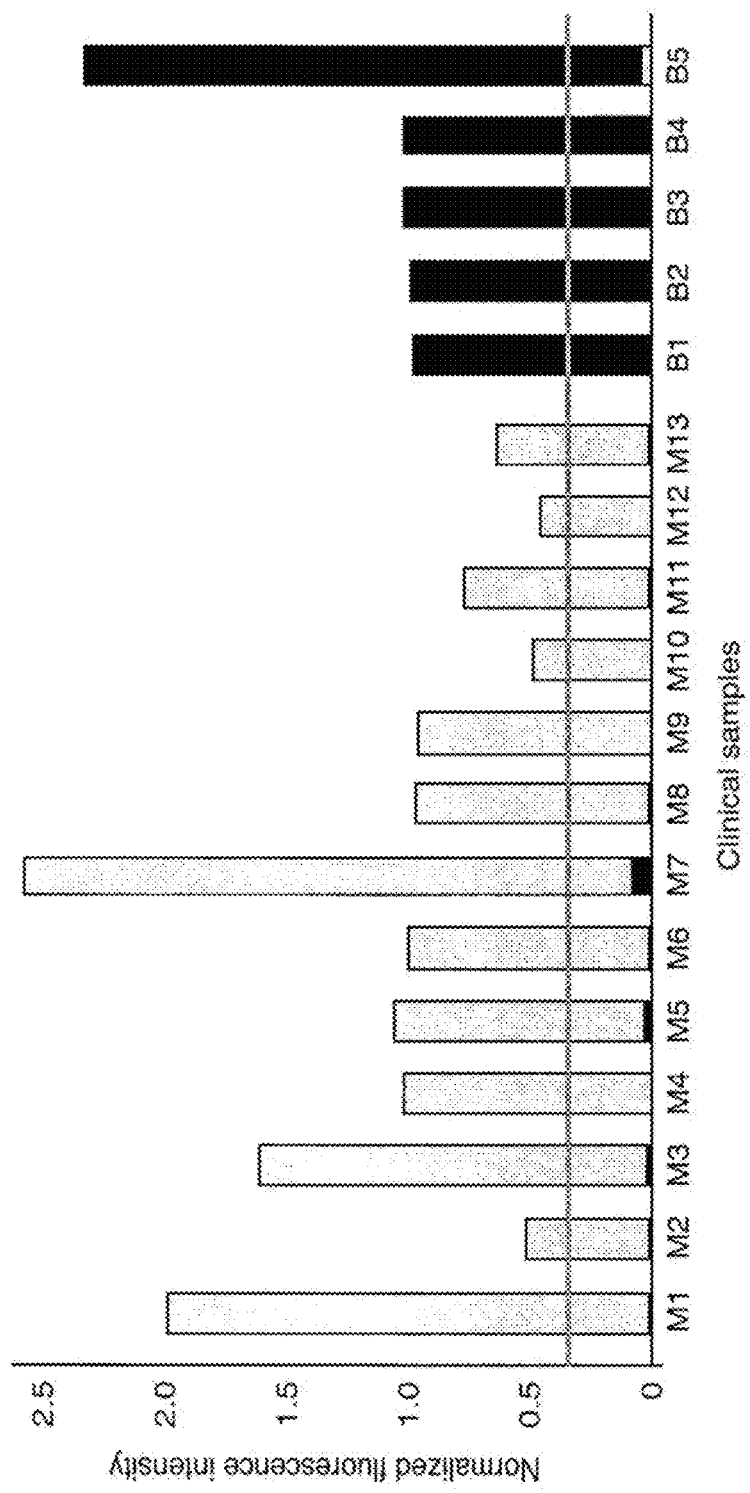
FIG. 24. Differentiating BCC and MCC using normalized miRNA signal intensity ratios. Following signal collection and correction (see FIG. 30 and FIG. 25, respectively), miR-205 (black) and miR-375 (grey) signal intensities were normalized against rRNA signal intensities for each tumor. A cut-off value (0.4) to differentiate BCC and MCC was first established on a test set (BCC1 and MCC1) of tumors. This cut-off value was subsequently used in blinded analysis to correctly identify four BCC (BCC2-5) and twelve MCC (MCC2-13) tumors.
Figure 29:
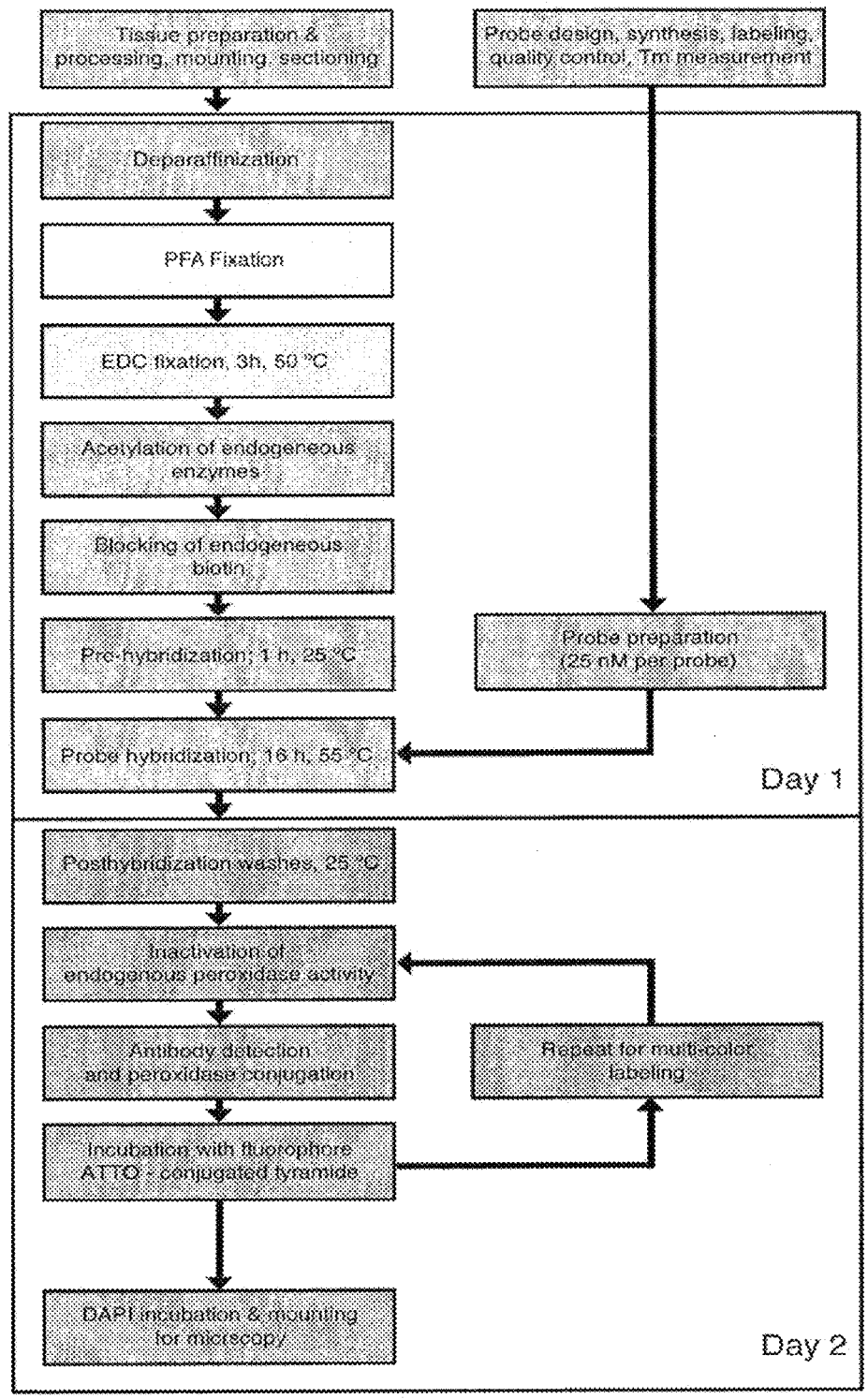
FIG. 29. Workflow diagram of optimized miRNA FISH protocol.
Figure 31:
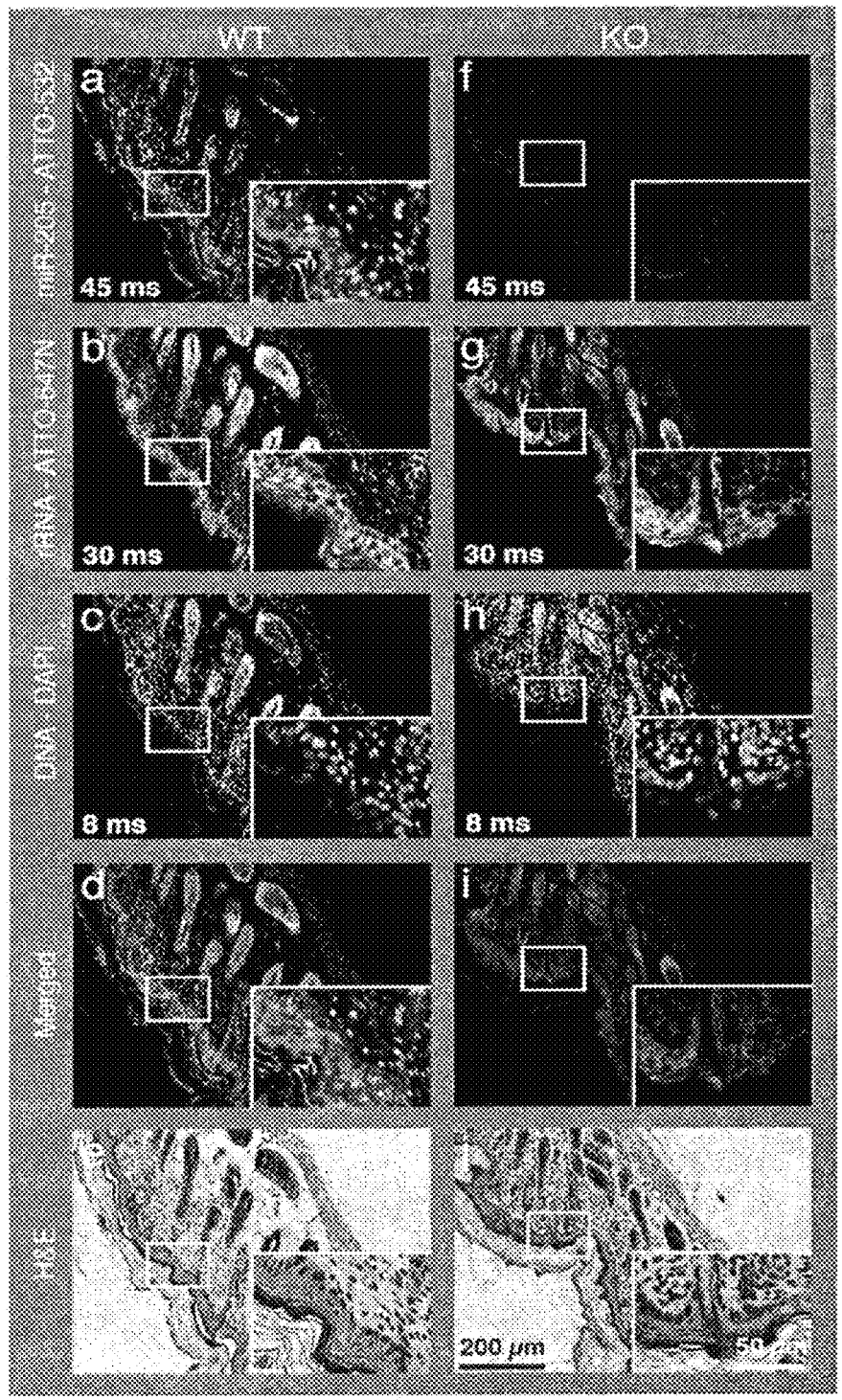
FIG. 31. Confirmation of miR-205 probe specificity in mouse skin tissues. Parallel detection of miR-205 and 28S rRNA in FFPE skin tissue sections from wild-type (WT) and miR-205 knockout (KO) mice using multicolor miRNA FISH. Probes and reaction conditions were identical to those used in FIG. 33. miR-205 signal was present in WT (a) but not KO (f) skin tissues. 28S rRNA signals were similar for WT and KO tissues (b, g). Nuclei were visualized using DAPI staining (c, h). Merged images (d, i) show miR-205 signals in epidermis, hair follicles, and a dermal cell subpopulation (in green), rRNA signals (in red), and nuclei (in blue). H&E stained WT and KO skin tissues (e, j) are histologically indistinguishable. Images were recorded at 20× magnification. Representative areas, indicated by white rectangles, are shown at 60× magnification to illustrate signal localization. Exposure times are indicated in ms. Scale bar, 200 µm, for insert, 50 µm (a-j).
Figure 32:
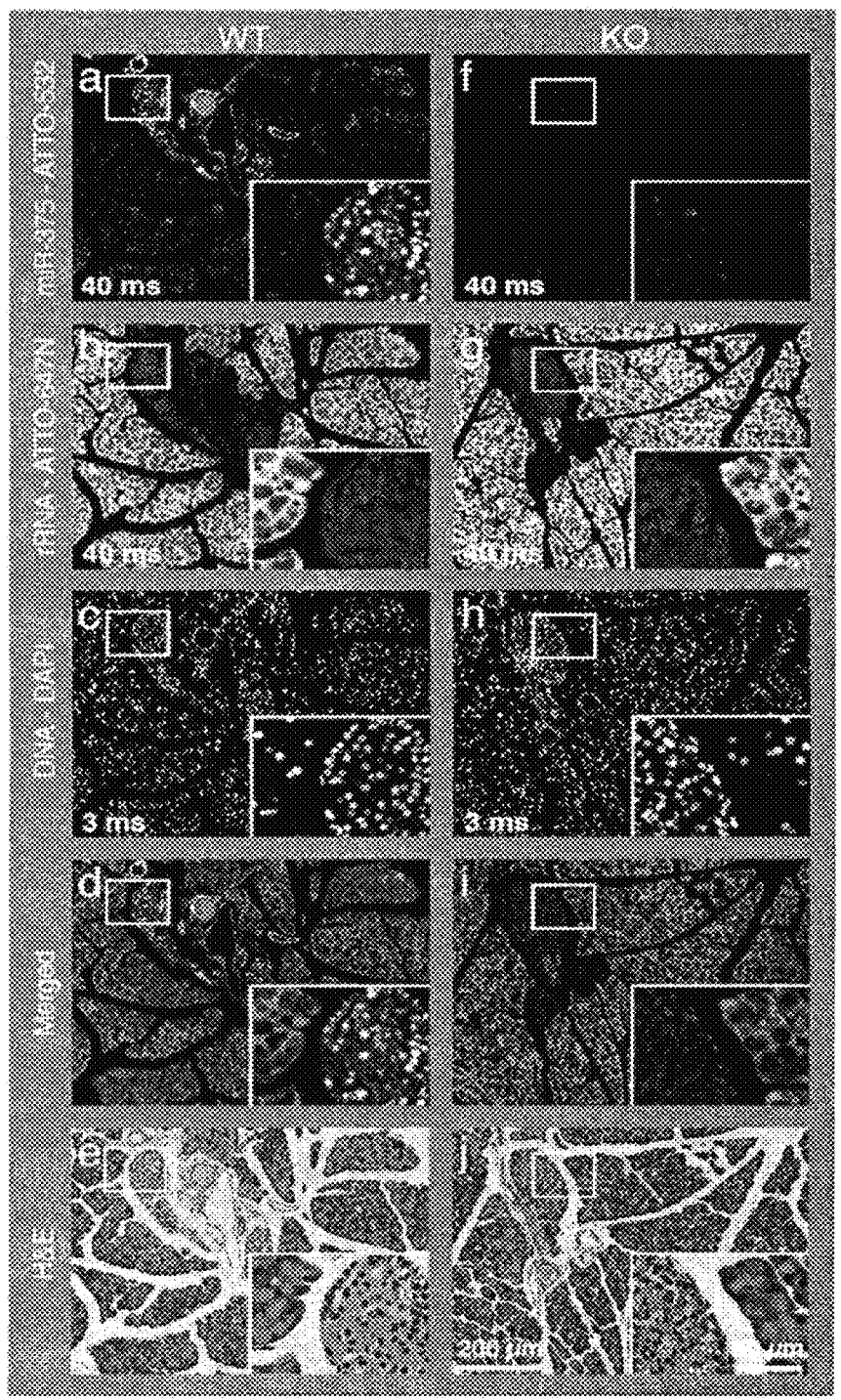
FIG. 32. Confirmation of miR-375 probe specificity in mouse pancreas tissues. Parallel detection of miR-375 and 28S rRNA in FFPE pancreas tissue sections from wild-type (WT) and miR-375 knockout (KO) mice using multicolor miRNA FISH. Probes and reaction conditions were identical to those used in FIG. 33. miR-375 signal was present in WT (a) but not KO (f) pancreatic islets and ductal epithelium. 28S rRNA signals were similar for WT and KO tissues (b, g). Nuclei were visualized using DAPI staining (c, h). Merged images (d, i) show miR-375 signals in pancreatic islets and ductal epithelium (in green), rRNA signals (in red), and nuclei (in blue). H&E stained WT and KO pancreas tissues (e, j) are histologically indistinguishable. Images were recorded at 20× magnification. Representative areas, indicated by white rectangles, are shown at 60× magnification to illustrate signal localization. Exposure times are indicated in ms. Scale bar, 200 µm, for insert, 50 µm (a-j).

Having identified tumor-specific miRNA biomarkers and optimized our miRNA FISH protocol, we validated our approach on FFPE tissue sections from four BCC and 12 MCC cases. We performed multicolor miRNA FISH (FIG. 29) using a cocktail of four ATTO-647N-conjugated probes complementary to 28S rRNA (directly labeled), fluorescein-hexylabeled miR-205 probe (detected using anti-fluorescein-HRP antibody and ATTO-532-tyramide), and biotin-hexylabeled miR-375 probe (detected using HRP-conjugated streptavidin and ATTO-488-tyramide). Specific miR-205 and miR-375 FISH signals were detected, corresponding to our small RNA sequencing results (FIG. 23). miR-205 signals were present in the cytoplasm and nuclei of BCC but absent from MCC tumor cells whereas miR-375 signals were present in the cytoplasm and nuclei of MCC but absent from BCC tumor cells; cytoplasmic and nuclear signals were attributed to targeting of mature and precursor miRNAs and/or variable tyramide coupling to cellular matrix reflecting distinct nuclear and cytoplasmic as well as cell-type dependent protein composition. miRNA and rRNA signals show partially overlapping cytoplasmic localization but were not co-localized to nucleoli. miRNA signal intensities were obtained, corrected (FIGS. 25 and 30), and subsequently normalized against rRNA intensities; a cut-off value was previously established to differentiate BCC or MCC tumors (FIGS. 24 and 25). miR-205 and miR-375 probe specificities were confirmed in wild-type and knockout mouse tissues (FIGS. 31 and 32). Substantially lower signals were seen for both probes when EDC fixation was omitted yielding near background signals that did no longer differentiate between MCC- and BCC-specific miRNA expression (FIG. 27).

Our multicolor miRNA FISH method has several advantages over existing methods, including our previous report on miRNA detection in non-embedded formaldehyde and EDC-fixed tissues. We (1) improved RNA fixation, increasing RNA retention through EDC crosslinking and omitting competing phosphate-containing buffers (2) assessed RNA retention and normalized miRNA signals against reference rRNA signals (3) enhanced antibody-based fluorescence signal amplification and eliminated tissue permeabilization using long linkers between the hapten and oligonucleotide probe and (4) developed the method for use with archived FFPE tissue sections.

Multicolor miRNA FISH for histologic differentiation offers advantages in rapid design and high-throughput synthetic generation of nucleic acid probes, quantitative detection of both coding and non-coding transcripts, discrimination between mRNA isoforms, and multiplexing capacity. In contrast, immunohistochemical methods for histologic differentiation rely on costly diagnostic-grade antibodies and require many months for antibody generation, validation, and adaptation for antigen-retrieval in fixed tissues. It is important to note that our miRNA FISH and conventional IHC methods are incompatible, likely due to EDC-based protein crosslinking (FIG. 33), however, conventional H&E staining can be readily performed upon acquisition of fluorescent images.

The described invention demonstrates that (1) MCC and BCC consistently express miR-375 and miR-205 despite variable underlying cytogenetic changes in these tumors, adding further weight to their respective roles as oncomirs and tumor suppressors; (2) MCV miRNA expression in MCC is low, favoring tumor cell growth and survival; and (3) miRNA sequence variation representing polyadenylation or polyuridylation sequence modifications and RNA editing. Additionally, it has been shown that in MCC, the miR-375 signal changes from cytoplasmic to nuclear on the same tissue section and close to areas of hypoxia or metastasis.

Example 3

We demonstrate the use of specifically designed LNA-modified DNA (LNA/DNA) probes. FIG. 45 shows comparison of LNA/DNA probes to DNA probes of various length. Here, we show how important it is to have short LNA/DNA probes to get desired specificity. For example, to target HER2/ERBB2, we synthesized 45 DNA probes (24-30 nt long), which were designed with GC content between 50 and 64% and TC content between 45 and 66%. No special care was taken regarding probes mishybridization to rRNA. Melting temperatures of these DNA probes varied from 48.1 to 56.9° C. rRNA mishybridization of DNA probes dominated the signal indicating that these DNA probes are not specific (FIG. 45a). Subsequently, DNA probes (24-30 nt long) were shorten either from 5'-end or 3'-end to avoid rRNA mishybridization (no segment longer than 8 nt with rRNA sequence complementarity) to yield 39 shorter DNA probes (14-21 nt long). Melting temperatures of these DNA probes varied from 38.8 to 47.1° C. (approximately 10° C. lower than longer DNA probes (24-30 nt long). However, rRNA mishybridization was still observed, especially at elevated temperatures (FIG. 45b). Only hybridization at 40° C. allowed small discrimination between HCC-1954 (HER2+) and MDA-MB231 (HER2–) breast cancer cell lines. At higher temperatures, rRNA mishybridization dominates the signal indicating that further denaturation of rRNA secondary structure increases rRNA mishybridization. To avoid mishybridization and increase probe specificity, we synthesize 53 short (11-15 nt long) directly labeled LNA-modified DNA (LNA/DNA) oligonucleotide probes for HER2/ERBB2. Melting temperatures of these LNA/DNA probes vary from 44.2 to 52.1° C. (approximately 5° C. lower than longer DNA probes (24-30 nt long), but 5° C. higher than shorter DNA probes (14-21 nt long). These LNA/DNA probes were shown to be specific and distinguished HCC-1954 (HER2+) from MDA-MB231 (HER2–) breast cancer cell lines (FIG. 45c).

FIG. 34 shows 8 LNA/DNA probes targeting 28S RNA demonstrating that pooling all 8 probes yield a signal intensity that is 8 times higher that that for an individual probe (FIG. 35), indicating that RNA FISH can be used for accurate target quantitation.

We utilize 1-ethyl-3-[3-dimethylaminopropyl]carbodiimide (EDC) as a fixation reagent forming irreversible phosphoamide bonds and amide bonds and thereby increasing retention of long and short (partially degraded) RNAs, followed by hybridization with short fluorescently labeled LNA/DNA probes in order to eliminate the conventional signal amplification steps. This probe design excludes even short homology to other RNA sequences and the length of each probe member within the probe pool is adjusted based on melting temperature.

Figure 40:
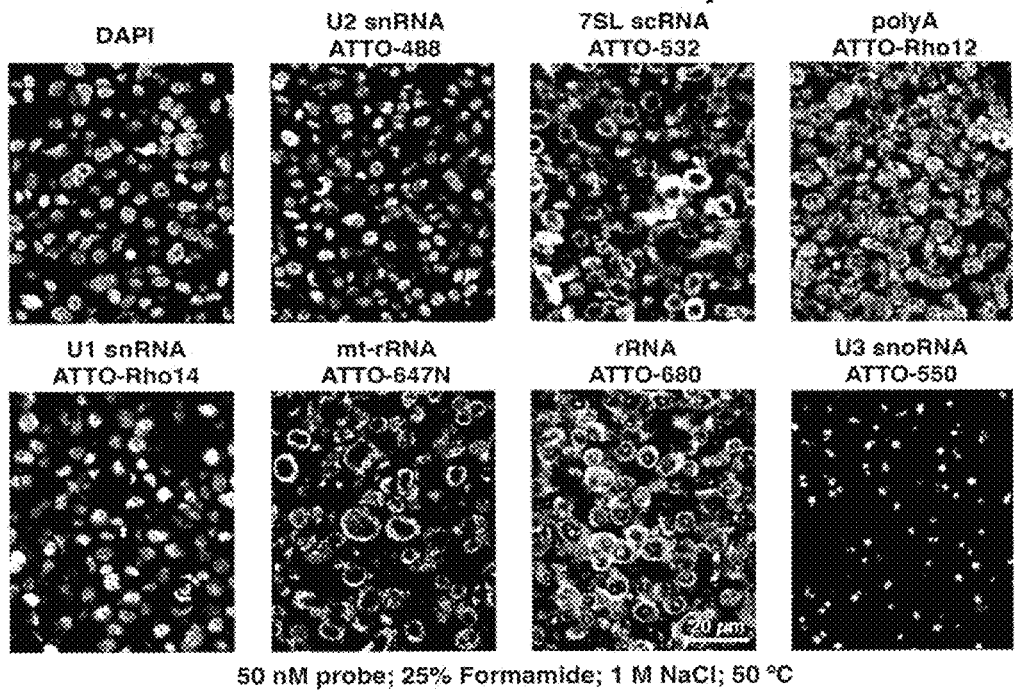
FIG. 40. Eight (8) Color RNA FISH using 7 non-coding RNAs and DAPI. RNA FISH was performed using HCC-1954 breast cancer cell line. The probes targeting U2 snRNA, 7SL scRNA, U1 snRNA, mt-rRNA, rRNA and U3 snoRNA are listed in FIG. 43. The sequence of polyT probe targeting polyA is shown in FIG. 37 and is named polyT4. U2 snRNA, 7SL scRNA, polyA, U1 snRNA, mt-rRNA, rRNA and U3 snoRNA probes were conjugated to ATTO-488, ATTO-532, ATTO-Rho12, ATTO-Rho14, ATTO-647N, ATTO-680 and ATTO-550, respectively. Probes were hybridized using 25% formamide and 1M NaCl at 50° C.
Figure 41:
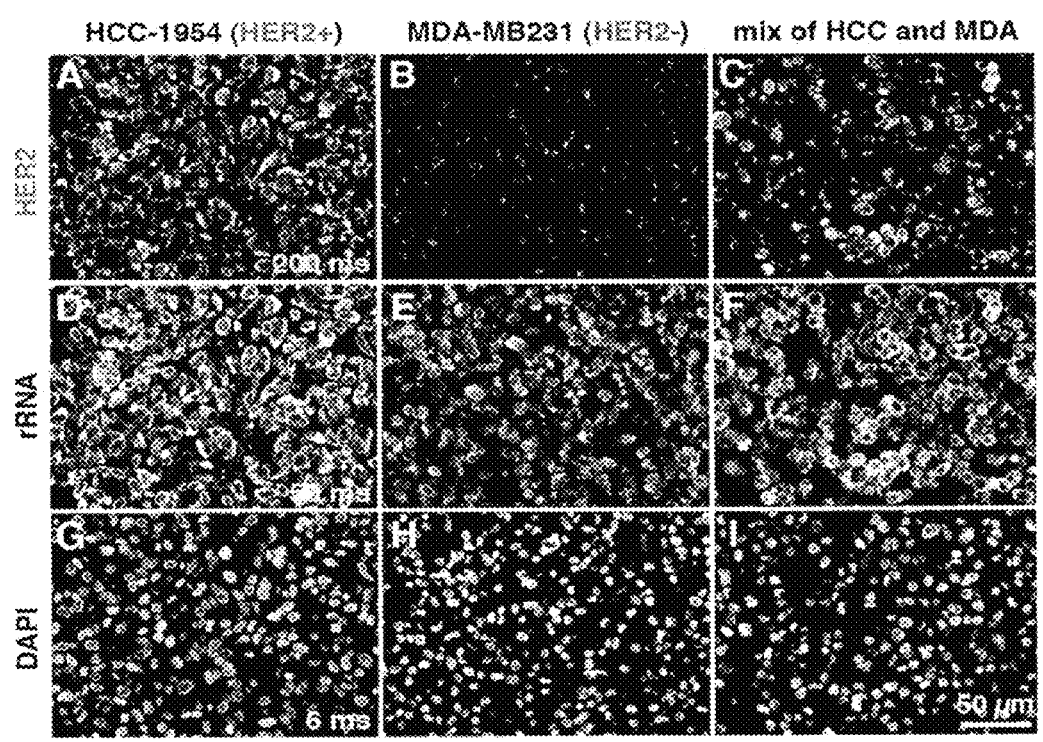
FIG. 41. Differentiating FFPE breast cancer cell lines using RNA FISH. 53 double-labeled fluorescence oligonucleotide probes targeting HER2 mRNA were assessed in FFPE HER2 positive (HCC-1954) and HER2 negative (MDA-MB321) cell lines. HER2 signals were 15-fold higher in HER2 positive (A) than HER2 (B) negative cells. When mixed (C), these cells can be differentiated visually. Reference rRNA (targeted by 5 fluorescent probes, D-F) and DAPI (G-I) signals were similar for both cell lines. Probes were hybridized using 25% formamide and 1M NaCl at 45° C. Exposure times are indicated in ms. Scale bar, 50 μm, (A-I).

This approach requires the synthesis of 20-100 short probes per target mRNA, each carrying two fluorophores (ATTO, Alexa, Cy, BODIPY, DyLight, Cyto, Seta, RadiantDy, CF or other dye, choosing the brightest, the most photo-stable and water-soluble, avoiding those which produce unspecific binding to protein scaffold). Subsequently, RNA FISH signals are scanned and normalized using control probes targeting polyA, mitochondrial and nuclear-encoded rRNA, U1, U2 or U6 small nuclear (sn) RNA, 7SL, 7SK or hy3 small cytoplasmic (sc) RNA and U3 small nucleolar (sno) RNA as shown in FIG. 40. We have established a robust, sensitive and specific method, and include necessary controls to monitor RNA retention and integrity.

In one aspect of the invention, we prepare and validate probes relevant or novel in cancer diagnostic and to quantify levels of including HER2/ERBB2, ER/ESR1, PR/PGR1 and vimentin (VIM) mRNAs or other mRNAs, which will be used in simultaneous multiple detection with different fluorophores to subclassify breast cancer, and in similar diagnostic applications. Sections of multiple different paraffin-embedded tumor cell line pellets are mounted on the same slide and processed and scanned in parallel. Cell lines are chosen based on expression data from RNA sequencing. Fluorescence intensities for target mRNAs as well as polyA, rRNAs, and mitochondrial rRNA, U1, U2 or U6 snRNA, U3 snoRNA, 7SL, 7SK scRNA or hy3 scRNA will be acquired and signal normalization procedures will be developed to be most suitable for comparison of clinical samples later. Our instrumentation (Olympus VS110 Digital Microscope) allows capture of up to 5 distinct fluorophores per experiment, but using Vectra Intelligent Slide Analysis System, we can simultaneously detect 8 or more distinct fluorophores with partially overlapping spectra, which then would allow us to simultaneously monitor many different transcripts leading to better diagnostic and prognostic utility. Finally we will apply the method to archived clinical materials.

Example 4

An illustrative example of the use of RNA FISH to provide for identification of translocations. Multiple different FFPE sarcoma tissue sections (2 Ewing sarcomas; 5 gastrointestinal clear cell sarcomas, 1 low grade fibromyxoid sarcoma, 1 myxoid liposarcoma, pleom liposarcoma) were analyzed for RNA retention. Fluorescent rRNA, poly(A) and protein (eosin B) stains were used to measure rRNA signals. RNA retention in all samples was observed. The poly(A) signal also was present in all samples, except for Ewing sarcoma. These data indicate that there is a sufficient amount of RNA in most tumor samples to allow for mRNA FISH diagnostics.

We first prepare and evaluate LNA/DNA probe sets monitoring the expression pattern and transcript levels of established IHC. We develop triple-fluorescence analysis, selecting the combination of targets so that at least one of the three scores positive in one of the possible tumor subtypes. If such a combination cannot be identified, we include a housekeeping gene, encoding a ribosomal protein or rRNA itself, paired with two markers.

About 10% of mostly soft tissue sarcomas are characterized by translocations involving members of the TET protein family. To diagnose translocations, we generate probe sets directed against the N-terminus of FUS, EWSR1, or TAF15 and the C-terminal fusion partners, a series of DNA binding proteins of the erythroblastosis virus-transforming sequence (avian ETS). FUS and EWSR1 are strongly expressed transcripts and their translocations are diagnostic for several sarcomas including multiple SBRCTs and SCTs. Among the most frequent translocation partners are ATFL, CREB1, WT1, ERG, MYC, NR4A3, FLI1, NFATC2, FEV, ETV1, E1AF, SP3, ZNF278, POU5FI, and DDIT3 or others. We initiate experiments using archived tumor specimens that have been tested for common translocations and measure the signal ratios between N-terminally directed FUS, EWSR1 or TAF15 probes with one fluorophore and those monitoring the C-terminal translocation partner with different fluorophore, anticipating a dramatic increase in relative expression of the C-terminal partner upon translocation.

This allows, for example, detection of translocation transcripts such as those from EWSR1 with FLI1 or ESWR1 with ERG and alike, many of which constitute fusion a transcription factor protein (like FLI, ERG, MYC) to a strong promoter containing protein, like (EWSR1, FUS). Probe sets with one fluorophore target the 5'-terminus upstream of the translocation point while probe sets with a different fluorophore target the 3'-terminus of the downstream translocation partner. The readout indicates an increase in fluorescence intensity of the downstream translocation partner similar in intensity to the upstream probe set. Simultaneous detection of multiple fluorophores allows detection of the translocation of several possible downstream sequences such as, for example, but not limited to, FLI1 or ERG translocated to upstream EWSR1. Fluorescence signals of similar strength involving EWSR1 and the fusion partners ERG but not FLI1 can be diagnostic for one type of translocation causing ewing sarcoma.

Iterative approaches to detect translocations, such as, for example, in a 3-color approach where probe sets specific to FUS and EWSR1 are used in combination with a pool of probes directed against the C-terminal domains of all known translocation partners, can be used. The TET proteins are extremely abundant; for example, in liposarcomas we have measured 500,000 and 5,000,000 copies of FUS and EWSR1 protein, respectively, whereas it is anticipated that the DNA-binding translocation factors are much less abundant. Monitoring the relative ratios of the fluorescence signals allows for recognition of fusion events and for definition of FUS or EWSR1 as the driver. The specific fusion then is identified in a using probe sets specific to the recognized N-terminal factor in combination with at least two or more probes now labeled such that a specific C-terminal translocation partner is recognized.

In summary, direct multicolor RNA FISH according to the invention facilitates the capture of gene expression information at cellular resolution, allowing the use of heterogeneous tissue samples and yield quantification of transcript levels through fluorescence measurements. The methodology can be used to identify known cancer markers, as well as novel RNA-based diagnostic markers, including microRNAs and other non-coding RNAs.

The foregoing description of some specific embodiments provides sufficient information that others can, by applying current knowledge, readily modify or adapt for various applications such specific embodiments without departing from the generic concept, and, therefore, such adaptations and modifications are intended to be understood within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

INCORPORATION OF SEQUENCE LISTING

Incorporated herein by reference in its entirety is the Sequence Listing for the application. The Sequence Listing is disclosed on a computer-readable ASCII text file titled, "sequence listing.txt", created on Mar. 27, 2014. The sequence listing.txt file is 78 kb in size.

What is claimed is:

1. A method for fixing an RNA molecule in a biological sample, said method comprising contacting the biological sample with an aldehyde-containing fixative, and subsequently contacting the sample with an aqueous solution comprising a carbodiimide and a heterocyclic derivative selected from the group consisting of an pyrazole, triazole or tetrazole or a combination thereof.

2. The method of claim 1, wherein said heterocyclic derivative has at least one of the following structures:

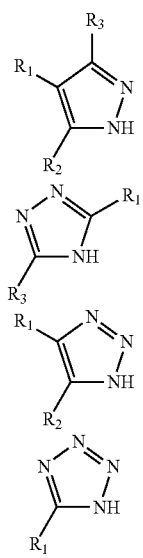

wherein $R_1$, $R_2$, and $R_3$ independently are H, alkyl, aryl, F, Cl, Br, I, CN, $NO_2$, $NH_2$, OH, SH, ethylthio-, alkyloxy-, or carbonyl.

3. The method of claim 1, wherein the aldehyde-containing fixative is formaldehyde, a derivative of formaldehyde, paraformaldehyde, glyoxal, glutaraldehyde, or combination thereof.

4. The method of claim 1, wherein the heterocyclic derivative is selected from the group consisting of 1-hydroxyl-benzotriazole and 5-ethylthiotetrazole.

5. The method of claim 4, wherein the heterocyclic derivative is 5-ethylthiotetrazole.

6. The method of claim 1, wherein the carbodiimide is selected from the group consisting of 1-ethyl-3-(3-dimethylaminopropyl)carbodiimide (EDC), 1-ethyl-3-(3-dimethylaminopropyl)carbodiimide hydrochloride (EDC-HCl), 1-cyclohexyl-3-(2-morpholinyl-(4)-ethyl)carbodiimide metho-p-toluenesulfonate (CMC), N,N'-dicyclohexylcarbodiimide (DCC), N,N'-diisopropylcarbodiimide (DIC), and 1-ethyl-3-(3-dimethylaminopropyl)carbodiimide methiodide (EDC-MeI).

7. The method of claim 6, wherein the carbodiimide is 1-ethyl-3-(3-dimethylaminopropyl)carbodiimide hydrochloride (EDC-HCl) or 1-ethyl-3-(3-dimethylaminopropyl)carbodiimide methiodide (EDC-MeI).

8. The method of claim 1, wherein the carbodiimide is 1-ethyl-3-(3-dimethylaminopropyl)carbodiimide hydrochloride (EDC-HCl) or 1-ethyl-3-(3-dimethylaminopropyl)carbodiimide methiodide (EDC-MeI) and the heterocyclic derivative is 5-ethylthiotetrazole.

9. The method of claim 8, wherein the 1-ethyl-3-(3-dimethylaminopropyl)carbodiimide hydrochloride (EDC-HCl) or 1-ethyl-3-(3-dimethylaminopropyl)carbodiimide methiodide (EDC-MeI) has a concentration of about 20 mM to about 300 mM.

10. The method of claim 9, wherein the solution comprising 1-ethyl-3-(3-dimethylaminopropyl)carbodiimide hydrochloride (EDC-HCl) or 1-ethyl-3-(3-dimethylaminopropyl)carbodiimide methiodide (EDC-MeI) contacts the sample at a temperature of about 20° C. to about 70° C.

11. The method of claim 1, wherein the solution comprising a carbodiimide and a heterocyclic derivative and has a pH of about 6.0 to about 10.0.

12. The method of claim 1, wherein the solution comprising a carbodiimide and a heterocyclic derivative has a pH of about 7.0 to about 8.0.

13. The method of claim 1, wherein the RNA molecule is a short RNA.

14. The method of claim 1, wherein the RNA molecule is a miRNA.

15. The method of claim 1, wherein the solution comprising a carbodiimide and a heterocyclic derivative further comprises a detergent.

16. The method of claim 15, wherein the detergent is selected from the group consisting TWEEN20 (Polysorbate20), TWEEN80 (Polysorbate80), TRITON A-100 (Octylphenol ethoxylate), TRITON-114 (ter-octylphenoxypoly(ethoxyethanol)), Digitonin, Saponin, CHAPS (3-[(3-Cholamidopropyl)dimethylammonio]-1-propanesulfonate), Denhardt's solution, Heparin, BRIJ35 (Polyethylene glycol hexadecylether), Sodium dodecyl sulfate (SDS), and urea.

17. The method of claim 1, further comprising contacting the solution comprising a carbodiimide and a heterocyclic derivative with a cyanogen halide.

18. The method of claim 17, wherein the cyanogen halide is selected from the group consisting of cyanogen bromide, cyanogen iodide, cyanogen chloride and cyanogen fluoride.

19. The method of claim 17, wherein the cyanogen halide is cyanogen bromide or cyanogen iodide.

20. A method for detecting a target RNA molecule in a biological sample, said method comprising
    a. contacting the biological sample with an aldehyde-containing fixative;
    b. subsequently contacting the sample with a solution comprising a carbodiimide and a heterocyclic derivative to produce crosslinked RNA in the sample, said heterocyclic derivative selected from the group consisting of an pyrazole, triazole or tetrazole or a combination thereof;
    c. contacting the sample with a probe, said probe being complementary to all or a part of a region of interest of the RNA in the sample, thereby producing hybridized RNA; and
    d. detecting the hybridized RNA as the target RNA.

21. The method according to claim 1, wherein the heterocyclic derivative is a tetrazol.

22. The method according to claim 20, wherein the heterocyclic derivative is a tetrazol.

* * * * *